United States Patent [19]

Oswald et al.

[11] Patent Number: 4,711,968
[45] Date of Patent: Dec. 8, 1987

[54] PROCESS FOR THE HYDROFOMYLATION OF SULFUR-CONTAINING THERMALLY CRACKED PETROLEUM RESIDUA

[75] Inventors: Alexis A. Oswald, Clinton Township, Hunterdon County, N.J.; Ram N. Bhatia, Baton Rouge, La.

[73] Assignee: Exxon Research & Engineering Co., Florham, N.J.

[21] Appl. No.: 914,802

[22] Filed: Oct. 3, 1986

[51] Int. Cl.$^4$ ............................................. C07C 45/50
[52] U.S. Cl. ..................................... 568/454; 568/909
[58] Field of Search ............................... 568/454, 909

[56] References Cited

U.S. PATENT DOCUMENTS

| | | | |
|---|---|---|---|
| 2,813,916 | 11/1957 | Boston | 260/666 |
| 2,905,629 | 9/1959 | Smith et al. | 208/127 |
| 2,905,733 | 9/1959 | Boston et al. | 260/683 |
| 3,661,543 | 5/1972 | Saxton | 48/206 |
| 3,816,084 | 6/1974 | Moser et al. | 48/206 |
| 4,055,484 | 10/1977 | Blaser et al. | 208/127 |
| 4,098,727 | 7/1978 | Haag et al. | 521/53 |
| 4,417,973 | 11/1983 | Angevine et al. | 208/46 |
| 4,454,353 | 6/1984 | Oswald et al. | 568/454 |
| 4,487,972 | 12/1984 | Haag et al. | 568/444 |
| 4,497,705 | 2/1985 | Weinberg et al. | 208/127 |

OTHER PUBLICATIONS

Aboul-Gheit et al, Erdol and Kohle, 38, 462–465 (1985), published Oct. 26, 1985.
Falbe, New Synthesis with Carbon Monoxide, 1980, Springer-Verglag, p. 73.
Falbe, Carbon Monoxide in Organic Synthesis, Springer-Verlag, 1970, pp. 18–22.
Alekseeva et al, Khim. i Tekhnol Topliv i Masel, 4(5), pp. 14–18 (1959)—English Translation.
Rudkovskii et al, Khim i Tekhnol Topliv i Masel, 3(6), pp. 17–24 (1958)—English Translation.
CA 95:213 and Marko et al., Chem. Ber., 96, 955–964 (1963).
CA 61:567 and Klumpp et al., Chem. Ber., 67, 926–933 (1964).
CA 54:254 and Berty, Chem. Techn. (Berlin) 9, 283–286 (1957).
CA 55:12131 and Marko et al, Chem. Ber., 94, 847–850 (1961).
CA 57:7520 and Freund et al, Acta Chim. Hung., 31, 177–84 (1962).
Marko, Proc. Symp. Coord. Chem., Tihany, Hungary, 271–279 (1964).
CA 64:6511 and Laky et al, Acta Chim. Hung. 46, 247–254 (1965).
CA 69:98140 and Marko et al, Acta Chim. Sci. Hung., 57, 445–451 (1968).
Zelenin et al, Khim i Tekhnol. Goryuch. Slantsev i Produktov ikh Pererabotki, 13, 325–332 (1964).
Forschungsgebiet T-84-064, Apr. 1984, Fell et al.
Marko et al, Chemistry and Industry, 1961, 1491–92.
Marko, Acta Chim. Sci. Hung., 59, 389–396 (1969).

*Primary Examiner*—Werren B. Lone
*Attorney, Agent, or Firm*—J. J. Mahon

[57] ABSTRACT

This invention is a catalytic process for the hydroformylation of olefinic, sulfur-containing thermally cracked petroleum streams to produce aldehydes and/or alcohols. The catalysts are homogeneous transition metal carbonyl complexes. Especially preferred catalysts for low and medium pressure hydroformylation are cobalt and rhodium carbonyl hydride complexes in which some of the carbonyl ligands have been replaced by trivalent phosphorus ligands. In a preferred high pressure hydroformylation, the sulfur-containing gas oil distillate feed is produced from vacuum residua by high temperature thermal cracking. Such a feed contains more than 20% olefins with 1-n-olefins as the single major types. These olefin components are hydroformylated in the presence of a cobalt carbonyl complex to produce a novel type of semilinear aldehyde or alcohol product containing an average of less than one alkyl branch per molecule.

31 Claims, 12 Drawing Figures

CAPILLARY GAS CHROMATOGRAM OF FLUID COKER NAPHTHA

CAPILLARY GAS CHROMATOGRAM OF THE
$C_{10}$ FRACTION OF FLUID COKER NAPHTHA

CAPILLARY GAS CHROMATOGRAM OF FLUID COKER LIGHT GAS OIL

400 MHz ¹H NUCLEAR MAGNETIC RESONANCE SPECTRUM OF FLUID COKER LIGHT GAS OIL

CAPILLARY GC ANALYSIS OF $C_{12}$ FLUID COKER FRACTION ON POLAR STATIONARY PHASE

PACKED COLUMN GC OF THE MIXTURE DERIVED FROM THE $C_{10}$ FRACTION OF FLUID COKER NAPHTHA BY HYDROFORMYLATION WITH COBALT

CAPILLARY GC OF FLUID COKER LIGHT GAS OIL MIXTURE AFTER HYDROFORMYLATION WITH TRIOCTYL PHOSPHINE COBALT COMPLEX AND ALCOHOL PRODUCT CAPPING

CAPILLARY GAS CHROMATOGRAM OF FLUID COKER LIGHT GAS OIL MIXTURE AFTER HYDROFORMYLATION IN THE PRESENCE OF COBALT

PROCESS FOR THE HYDROFOMYLATION OF SULFUR-CONTAINING THERMALLY CRACKED PETROLEUM RESIDUA

FIELD OF THE INVENTION

This invention provides a catalytic process for the hydroformylation of certain olefinic, sulfur containing, thermally cracked petroleum distillates, readily available at low cost, to produce certain desirable semilinear aldehydes and alcohols, by reacting the olefin components with CO and $H_2$. The catalysts are preferably dissolved transition metal carbonyl complexes. Especially preferred catalysts are cobalt and rhodium carbonyl hydride complexes in which some of the carbonyl ligands have been replaced by trivalent phosphorus ligands. A preferred feed is produced by the high temperature thermal cracking of vacuum resids, particularly by Fluid-coking and Flexicoking.

One aspect of the disclosure is a description of the types and structures of the compounds produced on the thermal cracking by petroleum resids. The naphtha and gas oil distillate fractions derived by the cracking of vacuum resids in fluidized bed processes were investigated by a combination of high resolution capillary gas chromatography, mass spectrometry and nuclear magnetic resonance spectroscopy. The different types of olefin reactants and the potential sulfur compound inhibitors were particularly analyzed.

Another aspect of the disclosure is the correlation, of the structures of the 1-n-olefin and the linear internal olefin reactant components of the feed and the various types of transition metal complex catalysts used, with the unique structures of the semilinear aldehyde and alcohol products. The high pressure cobalt carbonyl complex catalyzed hydroformylation of $C_{10}$ to $C_{15}$ gas oil distillate fractions and the resulting aldehyde product mixtures, consisting mostly of the corresponding n-aldehydes, 2-methyl branched aldehydes and 2-substituted ethyl and higher n-alkyl aldehydes, are particularly described.

PRIOR ART VERSUS THE PRESENT INVENTION

Hydroformylation is a well-known reaction for the conversion of pure olefin streams with CO and $H_2$ to aldehydes but has not been generally suggested for use on dilute olefin streams, such as petroleum distillates, which contain high concentrations of sulfur compounds and some nitrogen compounds. Streams containing these sulfur and nitrogen containing impurities have been considered as unsuitable hydroformylation feedstocks.

Present olefin feeds for hydroformylation are mostly propylene and its oligomers plus ethylene oligomers. The $C_7$ to $C_{13}$ alcohols derived from propylene oligomers and propylene/butenes copolymers are generally highly branched. In contrast, the $C_9$ to $C_{15}$ alcohols derived from ethylene oligomers are usually highly linear. Both types of higher alcohols are widely used intermediates in the production of plasticizer esters and ethoxylated surfactants. For most applications linear or semilinear alcohol intermediates are preferred. However, the ethylene oligomer feeds of linear alcohol production are much more costly than the branched olefin feeds derived from $C_3/C_4$ olefins.

As a part of the present invention it was discovered that thermally cracked petroleum distillates, particularly those derived from residual fuel oil by Fluid-coking and Flexicoking, contain unexpectedly major quantities of linear olefins. These olefins are valued below distillate fuel cost, because such cracked distillates have high concentrations of sulfur compounds and have to be extensively hydrogenated before they can be used as distillate fuels. The olefin components are converted to paraffins during such hydrogenations.

Furthermore, it was found in the present invention, that the sulfur compounds in such thermally cracked petroleum distillates are mostly inert aromatic, thiophene type compounds rather than catalyst inhibiting mercaptans. This finding led to the discovery of the present hydroformylation process which comprises reacting the linear and lightly branched olefin components of thermally cracked petroleum distillates containing sulfur compounds with CO and $H_2$ to produce semilinear aldehydes and alcohols.

When such olefin components were reacted with $CO/H_2$ in the presence of cobalt carbonyl complex catalysts at high pressure, the major aldehyde products were n-aldehydes, 2-methyl substituted aldehydes, 2-ethyl and higher alkyl substituted aldehydes in the order of decreasing concentrations.

As such the present process produces novel, highly desired, semilinear chemical intermediates at a low cost. Due to the unique olefin composition of the present cracked distillate feeds, such compounds cannot be produced by known processes.

The process of the present invention is particularly advantageous when the cracked petroleum distillate is a high boiling gas oil fraction containing 10 to 20 carbon atoms per molecule. In contrast to higher molecular weight olefins derived by the oligomerization of $C_3/C_4$ olefins, these gas oils are surprisingly reactive feeds for hydroformylation without prior treatment.

A group of preferred thermally cracked distillates, not previously considered as a hydroformylation feed, comprises naphtha and gas oil fractions produced in fluidized coking units. Integrated fluidized coking processes such as Fluid-coking and Flexicoking represent a superior refinery method for the conversion of residual fuel oil. The thermal cracking step of Fluid-coking and Flexicoking is identical. However, Fluid-coking does not utilize the residual coke produced with the coker distillate while Flexicoking employs the coke by-product for the production of low thermal value gas. A discussion of these processes is found in U.S. Pat. Nos. 2,813,916; 2,905,629; 2,905,733; 3,661,543; 3,816,084; 4,055,484 and 4,497,705 which are incorporated as references.

The preferred Fluid-coking and Flexicoking processes are low severity thermal cracking operations. Low severity is usually achieved by keeping the temperature relatively low in the range of 482° to 538° C. (900° to 1000° F.) while using a long residence, i.e., contact, time of about 20 to 60 seconds. Alternately, low severity can be achieved using high temperatures, in the order of 538° to 705° C. (1000° to 1300° F.) and contact times of less than 5 seconds. In a long residence time operation, additional amounts of the desired olefin components can be produced by reinjecting the heavy gas oil distillate products into the cracking line.

The residual fuel feeds for the above coking processes are usually vacuum residua which remain after most of the crude petroleum is removed by refinery distillation processes. As such these residua typically possess boiling points above 565° C. (1050° F.) and have Conradson carbon contents above 15%. These residua contain most of the undesirable components of the crude, i.e. sulfur and nitrogen compounds and metal complexes. On coking much of the sulfur ends up in the distillate products. As a result of high temperature thermal cracking, major amounts of olefinic components are also formed and become major constituents of such distillates. In spite of their high monoolefin content such distillates generally were not considered as hydroformylation feeds because of their high sulfur and conjugated diolefin content.

Although sulfur compounds in general were regarded as catalyst inhibitors, the production of alcohols or aldehydes via the hydroformylation of the olefinic components of some refinery streams has been previously suggested. For instance, U.S. Pat. No. 4,454,353 to Oswald et al, issued June 12, 1984, teaches the use of trihydrocarbyl silyl substituted diaryl phosphine transition metal carbonyl hydride complex hydroformylation catalysts with "refinery streams of olefins, containing paraffin by-products such at $C_1$–$C_{20}$ paraffins . . . ".

Haag and Whitehurst in U.S. Pat. Nos. 4,098,727 and 4,487,972 disclose the production of aldehydes and alcohols via the hydroformylation of olefinic streams in the presence of insoluble, polymer anchored complexes of Group VIII metals with nitrogen, sulfur, phosphine and arsine ligands. Example 32 shows the hydroformylation of a cracked gasoline feed containing 230 ppm sulfur in the presence of a rhodium amine complex attached to a styrene-divinylbenzene polymer.

The process disclosed in U.S. Pat. No. 4,417,973 to Angevine et al, is one for "upgrading" various straight chain olefin-containing feedstocks, such as shale oil, FCC light cycle oil, and coker liquids, to branched paraffins. The process involves the sequential steps of hydroformylation and hydrotreating/hydrogen reduction, preferably, in the presence of a heterogeneous supported Co/Mo catalyst. The reaction products of the hydroformylation step were neither separated nor identified. The final products are branched paraffins. The sulfur content of the various feedstocks are shown in the Examples to be 0.29 to 1.33 wt.%.

Other disclosures discussing the use of cobalt-based homogeneous catalysts are known.

For instance, a series of papers by Marko et al teach the reaction of dicobalt octacarbonyl, a hydroformylation catalyst precursor, with elemental sulfur and organic sulfur compounds. Various sulfur-containing cobalt complexes were isolated. Reactions with sulfur led to $[Co_2S(CO)_5]_n$ and $Co_3S(CO)_9$. See, Chem. Ber., 94, 847–850 (1961); Chem. Ind., 1491–1492 (1961); Chem. Ber., 96, 955–964 (1963). Hydrogen sulfide is said to react to give the same complexes. Mercaptans and disulfides lead mainly to sulfide derivatives of cobalt trimers and tetramers. Marko et al states that, under hydroformylation conditions, all these complexes are converted to catalytically inactive cobalt sulfide [Chem. Ber., 97, 926–933 (1964).] Cobalt thioether complexes are also said to be either inactive or less active in hydroformylation than unsubstituted dicobalt octacarbonyl [Acta Chim. Sci. Hung., 59, 389–396 (1969)].

Another series of papers by Marko and co-workers describes the hydroformylation/hydrogenation of $C_6/C_8$ olefins present in cracked gasoline. The papers describe a process for converting a sulfur-containing $C_7$ fraction of cracked gasoline using a 1 to 2 ratio of hydrogen to carbon monoxide at 200° C. under 300 atm (4,409 psi) pressure to produce 85% octyl alcohol, an intermediate for a dioctyl phthalate plasticizer, with 10% higher boiling by-product formation [J. Berty, E. Oltay and L. Marko, Chem. Tech., (Berlin) 9, 283–286 (1957); M. Freund, L. Marko and J. Laky, Acta Chim. Acad. Sci. Hung., 31, 77–84 (1962). Under these reaction conditions, using cyclohexene as a model olefin, ethyl mercaptan and diethyl disulfide were found to be strong inhibitors of hydroformylation even in small amounts while diethyl sulfide and thiophene had not effect in molar concentrations up to tenfold of cobalt [L. Marko, Proc. Symp. Coordn. Chem. Tihany, Hungary, 271–279 (1964)]. Similar but more pronounced effects were observed on the hydrogenation of aldehyde intermediates to alcohols [J. Laky, P. Szabo and L. Marko, Acta Chim. Acad. Sci. Hung., 46, 247–254 (1965)]. Sulfur containing cobalt trimers, e.g., of the formula $Co_3(CO)_9S$ and $Co_3(CO)_6(S)(SR)$ were postulated as intermediates in the conversion of active $Co_2(CO)_8$ into insoluble inactive CoS [L. Marko and M Freund, Acta Chim. Acad. Sci. Hung., 57, 445–451 (1968)].

Russian researchers, particularly Rudkovskii and co-workers, also published a series of articles on the hydroformylation of olefin components in petroleum distillates with dicobalt octacarbonyl catalyst. These distillates were not characterized chemically. One paper describes the production of $C_{11}$ to $C_{17}$ alcohols from high boiling distillate fractions of contact coking. The process entails hydroformylation, preferably at 170° C. and 300 atm (4409 psi), followed by hydrogenation in a mixture with unreacted hydrocarbons over a $2NiS.WS_2$ catalyst [K. A. Alekseeva, D. M. Rudkovskii, M. I. Riskin and A. G. Trifel, Khim, i Tekhnol. Topliv i Masel 4 (5), 14–18 (1959)]. Another paper describes a similar hydroformylation of lower molecular weight cracked gasoline olefins [D. Rudkovskii, A. G. Trifel and K. A. Alekseeva, Khim. i Tekhnol. Topliv i Masel, 3(6), 17–24 (1958)]. Suitable $C_7$–$C_8$ naphtha feeds from thermal cracking of a mixture petroleum fractions, phenol extracts and petroleum were later described [P. K. Zmiewski, T. N. Klyukanova and G. M. Kusakina, Neft, i Gas Prom., Inform. Nauchn. Tekhn. Sb (4) 48–49 (1964)].

Another journal article, appeared in a Russian journal, Khim. i Tekhnol. Goryuch. Slantsev i Produktov ikh Pererabotki, on pages 325 to 332 of the 13th issue of 1964, and was authored by N. I. Zelenin and co-workers. This publication considered the hydroformylation of the olefin components of shale gasoline and diesel fractions to produce plasticizer and surfactant alcohols. It particularly discussed the removal of sulfur compounds which can be hydroformylation inhibitors.

A research report, Forschungsbericht T-84-064, was made to the German Federal Department of Research and Technology in April 1984. The authors, B. Fell, U. Buller, H. Classen, J. Schulz and J. Egenolf disclose the hydroformylation of a $C_5$–$C_6$ cracked gasoline between 150°–175° C. at 200 atm (2939 psi) in the presence of 0.4–0.2% cobalt to obtain oxo-products with 65% selectivity. The use of a triphenyl phosphine rhodium complex based catalyst system at this high pressure was reported to result in little conversion.

Two monographs on the organic chemistry of carbon monoxide by Falbe and co-workers of Ruhrchemie include major chapters on hydroformylation. The effect of hydroformylation of cobalt catalyst poisons, particularly sulfur compounds, is summarized on pages 18 to 22 of the first monograph [J. Falbe, Carbon Monoxide in Organic Synthesis, Chapter I, The Hydroformylation Reaction (Oxo Reaction/Roelen Reaction), pages 1 to 75, Springer Verlag, New York (1970)]. The second monograph also reviews the effect of poisons on modified rhodium catalysts and concludes that these catalysts, due to their low concentration, are more susceptible to poisoning [New Synthesis with Carbon Monoxide, Ed. J. Falbe, Chapter 1 by B. Cornils, pages 1 to 225, particularly page 73, Springer Verlag, New York 1980].

Overall the prior art taught away from the hydroformylation process of the present invention rather than suggesting it. In general, the use of cracked petroleum distillates containing high concentrations of sulfur was to be avoided. Soluble transition metal carbonyl complexes containing trivalent phosphorus ligands were never used successfully for the hydroformylation of such distillates. Known low pressure hydroformylation processes have low sulfur limits for the feeds.

Although the high pressure hydroformylation of cracked gasoline of relatively low sulfur content was extensively studied by Marko et al. in the presence of added dicobalt octacarbonyl, the feeds and conditions of the present process were neither used or suggested. It was not proposed to utilize coker distillate feeds of high linear olefin and sulfur compound content for the production of aldehydes and alcohols by hydroformylation. The high pressure, cobalt catalyzed $C_7$ gasoline hydroformylation/hydrogenation process Marko et al. developed is run at 200° C. and produces $C_8$ alcohols in one step. In contrast, the temperature range of the present high pressure cobalt catalyzed process is 110° to 180° C., preferably 120° to 145° C. and the main products are aldehydes. Pure alcohol products in this process are produced in a separate step.

The present cobalt carbonyl complex catalyzed high pressure process employs $C_8$ to $C_{20}$ distillate feeds produced by high temperature fluid coking of vacuum resids. These feeds contain more than 0.1% sulfur and more than 20% olefins. More than 30% of the total olefins present are of Type I.

Due to the specific linear olefinic character of the present feeds, such hydroformylations produce unique aldehyde and alcohol products of a semilinear character having less than one branch per molecule. The major components of the primary aldehyde products are n-aldehydes, 2-methyl branched aldehydes. Most of the rest are 2-ethyl or higher n-alkyl branched aldehydes. On hydrogenation they provide the corresponding alcohols.

The present process is also distinguished over the prior art as producing $C_9$ to $C_{13}$ the above semilinear alcohols uniquely suited for the preparation of novel plasticizer esters and $C_9$ to $C_{30}$ semilinear alcohols specially applicable for the preparation of new surfactants.

None of the references teach either alone or in combination the presently described and claimed process.

SUMMARY OF THE INVENTION

Figure 1:
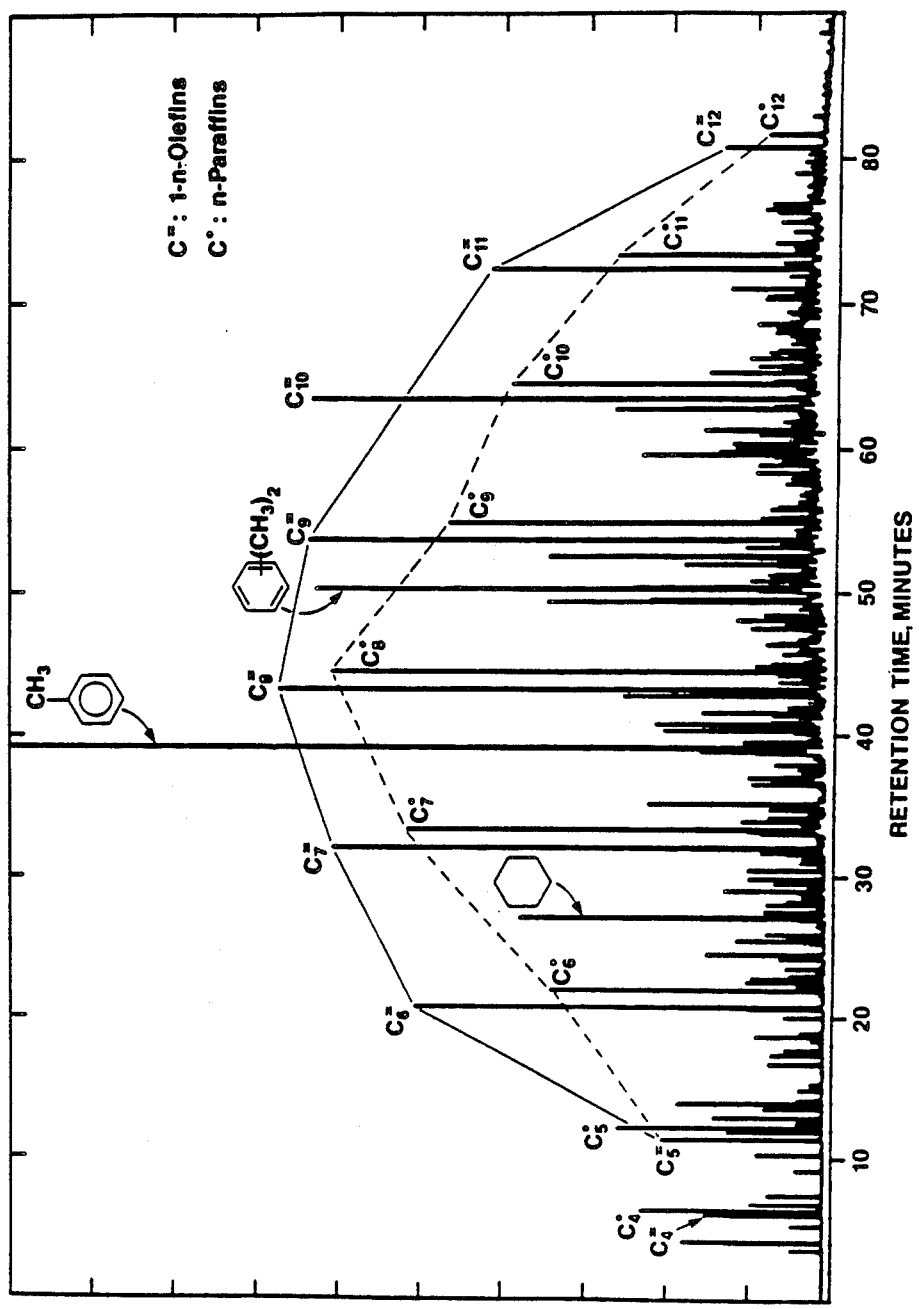
FIG. 1 shows the capillary gas chromatogram of a Fluid-coker naphtha feed in the $C_4$ to $C_{12}$ range, with an indication of the major 1-n-olefin and n-paraffin components.

This invention is a hydroformylation process in which the olefin components of a cracked petroleum distillate fraction containing substantial amounts of 1-n-olefins and sulfur bearing compounds are reacted with carbon monoxide and hydrogen in the presence of a homogeneous Group VIII transition metal carbonyl complex catalyst. The products are aldehydes and/or alcohols of largely linear character and as such preferably have less than one alkyl branch per molecule on the average. The products may be separated by distillation from the unreacted components of the distillate feed.

The preferred catalysts are soluble rhodium or cobalt carbonyl complex catalysts. The complex may be modified by a trivalent phosphorus, arsenic, nitrogen and/or sulfur ligand. Triorgano-phosphine ligands are most preferred. Cobalt carbonyl catalysts may also desirably be used without added phosphorus ligands.

The reaction conditions under which the feeds may be hydroformylated cover broad ranges. Temperatures ranging from 50° to 250° C. and pressures ranging from essentially atmospheric to 5000 psi (340 atm) may be used. The more preferred conditions depend on the type of the olefin to be reacted and the type of transition metal catalyst to be used.

When phosphorus ligand rhodium complex based catalysts are employed, low pressures ranging from 50 to 2000 psi preferably 100 to 1500 psi are used. A broad range of temperatures preferably from 50° to 250° C., more preferably from 80° to 200° C. can be used.

Phosphine cobalt complex catalysts can be advantageously employed at pressures between 500 and 4500 psi, preferably between about 500 to 2500 psi, and at reaction temperatures between 150° and 200° C.

High pressure cobalt catalysts, in the absence of added ligands, require pressures between 2500 and 6000 psi, preferably between 3000 and 4500 psi. They are preferably employed between 100° and 180° C., more preferably between 110° and 170° C., most preferably between 120° and 145° C. Higher pressures of reactant gas, specifically CO, allow the use of higher reaction temperatures without catalyst decomposition and/or deactivation.

In summary, the dependence of reaction conditions on the type of catalyst systems employed is shown by the following tabulation:

| Group VIII Metal Employed | Trivalent P Ligand Employed | Reaction Conditions Temperature °C. | Pressure psi |
|---|---|---|---|
| Rh | Yes | 50–250 | 50–2000 |
| Co | Yes | 150–200 | 500–4500 |
| Co | No | 100–180 | 3000–4500 |

In the present process, the feed for the high pressure cobalt catalyst contains 1-n-olefins as the major type of olefins and is derived from petroleum residua by Flexcoking or an equivalent high temperature thermal cracking process. Starting with this feed, the present process provides aldehydes and/or alcohols of a highly linear character having less than one alkyl branch per molecule on an average. This feed and product is also preferred for the other catalysts.

DESCRIPTION OF THE PREFERRED EMBODIMENTS

As noted above, this invention is a hydroformylation process for the production of aldehydes and/or alcohols of a largely linear character, i.e., products stream having preferably less than one alkyl branch per mole on the average, from a cracked petroleum distillate feedstock containing substantial amounts of 1-n-olefins and sulfur compounds. The process comprises reacting the distillate with $CO/H_2$ in the presence of a Group VIII transition metal complex catalyst.

As such, the present hydroformylation process comprises reacting with hydrogen and carbon monoxide an olefinic cracked petroleum distillate feed, particularly in the $C_8$ to $C_{35}$ carbon range, preferably produced from petroleum residua by high temperature thermal cracking, and containing 1-n-olefins as the major type of olefin components, the percentage of Type I olefins being preferably more than 30%, said feeds also containing organic sulfur compounds in concentrations preferably exceeding 0.1%, more preferably exceeding 1%.

The hydroformylation reaction is carried out at temperatures between about 50 and 250° C. and pressures in the range of 50 and 6000 psi, dependent on the particular catalyst employed.

The reaction takes place in the presence of effective amounts of a Group VIII transition metal carbonyl complex catalyst preferably selected from the group of Fe, Co, Rh, Ru, Ir and Os, more preferably Rh, Co, Ru and Ir, most preferably Co or Rh, a preferred group of complexes being modified by a trivalent phosphorus ligand, preferably triorgano-phosphine or phosphite ester.

Such hydroformylations produce aldehydes and/or alcohols, preferably aldehydes of a semilinear character, preferably having an average of less than one alkyl branch per molecule. These products more preferably contain n-aldehydes and 2-methyl branched aldehydes as the major products most of the rest being various 2-ethyl or higher n-alkyl branched aldehydes. The reduction of these aldehydes by hydrogen to the corresponding alcohols is preferably carried out in a separate step in the presence of a sulfur insensitive catalyst, preferably based on Co, Mo, Ni, W in a sulfided form.

Distillate Feeds

The cracked petroleum distillate feeds of the present hydroformylation process are preferably derived via thermal cracking. Thermal cracking processes produce hydrocarbons of more linear olefinic character than catalytic cracking. The presence of linear olefin components, particularly 1-n-olefins, in the cracked distillates is important for the production of normal, non-branched aldehydes and mono-branched aldehydes using hydroformylation. For example, the hydroformylation of 1-hexene can produce n-heptanal as the main n-aldehyde product and 2-methylhexanal as the minor iso-aldehyde product. These in turn can be hydrogenated to the corresponding alcohols:

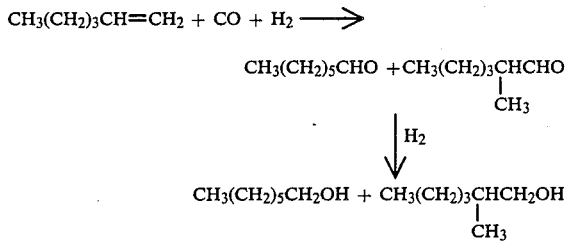

The linear normal aldehyde and alcohol products are generally more desired than the branched iso-compounds as intermediates for the production of high quality plasticizers and surfactants. Among the iso compounds, the 2-methyl branched products have the least adverse effect on product quality.

The percentage of 1-n-olefin components of thermally cracked petroleum distillates generally increases with the temperature of cracking. Therefore, the distillate products of high temperature thermal cracking processes such as Fluid-coking and Flexicoking are preferred feeds for the present process. Delayed coking, which is normally operated at a lower temperature, can also produce suitable feeds for the present process when operated at sufficiently high temperature. Other less preferred, milder cracking processes such as the thermal cracking of gas oils and the visbreaking of vacuum residues can also produce distillate feeds for the present process. Suitable distillate feeds can be also prepared in thermal processes employing a plurality of cracking zones at different temperatures. Such a process is described in U.S. Pat. Nos. 4,477,334 and 4,487,686. Each of these thermal cracking processes can be adjusted to increase the olefin contents of their distillate products.

Higher distillate fractions of steam cracking can be also used as a feed in the present process.

The olefin content of the cracked distillate feeds of the present invention is above 20%, preferably above 30%, more preferably above 40%. The 1-n-olefins are preferably the major type of olefin components.

In the high pressure operation of the present process, using cobalt carbonyl complexes without any added phosphine ligand, the feeds should be thermally cracked distillates containing 1-n-olefins as the major olefin type. These feedstocks are preferably produced by the FLEXICOKING process or FLUID-COKING process and similar high temperature coking processes.

Distillate fractions of cracking processes can be hydroformylated without prior purification. However, the cracker distillate feeds may be treated to reduce the concentration of certain sulfur and nitrogen compounds prior to the hydroformylation process. These impurities, particularly the mercaptans, can act as inhibitors to the hydroformylation step. The disclosed process is operable in the presence of the impurities but adjustments to the catalyst level and/or to the reactant gas partial pressure (notably the CO pressure) are preferably made to compensate for the inhibition by the sulfur compounds.

One method for the removal of mercaptans, is selective extraction. Most of the extractive processes employ basic solvents. Examples of such processes include the use of aqueous and methanolic sodium hydroxide, sodium carboxylate (isobutyrate, naphthenate) sodium phenolate (cresolate) and tripotassium phosphate. Sulfuric acid of carefully controlled concentration and temperature can be also used although it is less selective than caustic. For example, a 30 minute treatment with 12% $H_2SO_4$ between 10° and 15° C. can be used.

The preferred cracked distillates of the present feed contain relatively high amounts of organic sulfur compounds. The sulfur concentration is preferably greater than 0.1% (1000 ppm), more preferably greater that 1% (10000 ppm). The prevalent sulfur compounds in these feeds are aromatic, mainly thiophenic. Most preferably the aromatic sulfur compounds represent more than 90% of the total. This finding is important for the present process since thiophenes, benzothiophenes and similar aromatic sulfur compounds do not inhibit hydroformylation.

For the removal of sulfur, as well as nitrogen compounds, adsorption on columns packed with polar solids, such as silica, fuller's earth, bauxite, can be also used. Treating columns containing such adsorptive solids can be regenerated, e.g., by steam. Alternatively, zeolites can be used to enrich the present feeds in 1-n-olefins and n-paraffins.

The inert aromatic hydrocarbon components of the feed can be also removed together with the aromatic sulfur compounds, preferably by methods based on the increased polarity of aromatics compared to the aliphatic components. Selective solvent extraction methods using a polar solvent such as acetonitrile or a nonpolar solvent such as perfluoroethane may be employed for extracting the polar and nonpolar components, respectively.

Finally, sulfur compounds can also be converted to easily removable hydrogen sulfide by passing the cracked distillate through a high temperature fixed bed of either bauxite or fuller's earth or clay, preferably between 700°–750° C. One disadvantage of this catalytic desulfurization method is the concurrent isomerization of olefin.

The cracked refinery distillate feed is preferably separated into various fractions prior to hydroformylation. Fractional distillation is the preferred method of separation. The different distillate fractions contain different ratios of the various types of olefin reactants and have different inhibitor concentrations. The preferred carbon range of the thermally cracked feeds is $C_5$ to $C_{35}$. The $C_8$ to $C_{25}$ range is more preferred. The most preferred range is $C_{11}$ to $C_{20}$. It is desirable to limit the carbon number range of any given distillate feed by efficient fractional distillation to 5 carbons, preferably three carbons, more preferably one carbon, to allow efficient separation of the products from the unreacted feedstock.

For example, a cracked distillate feedstock fraction might contain hydrocarbons in the $C_7$ to $C_9$ range. The main components of such a fraction would be $C_8$ hydrocarbons. Upon hydroformylating the olefinic components of such a fraction, $C_8$ to $C_{10}$ (mainly $C_9$) aldehydes and alcohols would be obtained. These oxygenated products all boil higher than the starting $C_7$–$C_9$ hydrocarbons. The products could therefore be separated by distillation from the unreacted feed fraction.

For the preparation of plasticizer alcohols, olefin feeds containing from 5 to 12 carbon atoms are preferred. These can be converted to $C_6$–$C_{13}$ aldehydes and in turn $C_6$ to $C_{13}$ alcohols. The more preferred feeds contain $C_8$ to $C_{12}$ olefins and as such provide $C_9$ to $C_{13}$ alcohols. The most preferred feeds are $C_{10}$ to $C_{12}$ olefins. The alcohols may be reacted with phthalic anhydride to produce dialkyl phthalate plasticizers of appropriate volatility. The more linear is the character of the alcohol employed, the better are the low temperature properties of the plasticized products, e.g., plasticized PVC. The preferred feeds of the present invention are uniquely advantageous in providing low cost olefins for the derivation of high value plasticizers.

For the preparation of surfactants, higher molecular weight olefins are usually preferred. Their carbon numbers per molecular range from $C_8$ to $C_{35}$. These feeds can be used for the derivation of $C_9$ to $C_{36}$ aldehydes. $C_{12}$ to $C_{20}$ olefin feeds leading to $C_{13}$ to $C_{21}$ surfactant alcohols are more preferred. These aldehydes can be either reduced by hydrogen to the corresponding alcohols or oxidized by oxygen to the corresponding carboxylic acids. The alcohols can then be converted to nonionic surfactants, e.g., by ethoxylation; anionic surfactants, e.g., by sulfonation and cationic surfactants, e.g., by amination or cyanoethylation followed by hydrogenation.

Olefin Reactant Compounds

The main olefin reactant components of the present feed are nonbranched Types I and II or mono-branched Types III, and IV as indicated by the following formulas (R=hydrocarbyl, preferably non-branched alkyl):

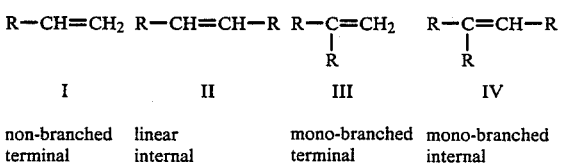

| I | II | III | IV |
|---|---|---|---|
| non-branched terminal | linear internal | mono-branched terminal | mono-branched internal |

The concentration of Type I olefins is preferably greater than 30% of the total olefin concentration. The percentage of Type II olefins is greater than 15%. Type V olefins of the formula $R_2C=CR_2$ are essentially absent.

The n-alkyl substituted Type I olefins, i.e., 1-n-olefins, are generally present at the highest concentration in thermally cracked distillates among the various olefinic species. The main product of 1-n-olefin hydroformylation is the corresponding n-aldehyde having one carbon more than the reactant. The hydroformylation of Type II linear internal olefins and Type III monobranched terminal olefins provides mono-branched aldehydes and in turn alcohols:

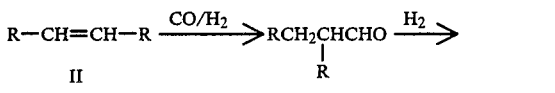

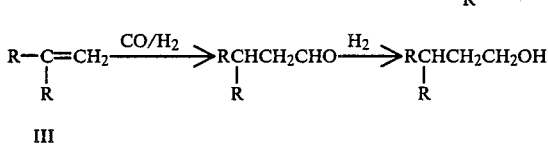

Only the hydroformylation of type IV mono-branched olefins leads to di-branched products.

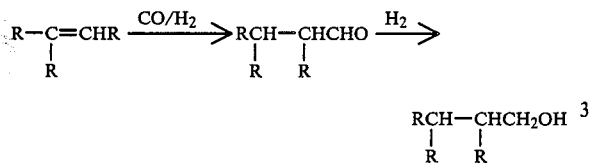

Types I to IV olefins have a decreasing reactivity in this order. Thus it is possible, using the selective catalytic process of the present invention, to convert either the Type I, or the Types I and II, or the Types I to III olefins, selectively to products containing (on an average) less than one branch per molecule. Of course, the most linear products can be derived by hydroformylating only the Type I olefins.

Type II linear internal olefins can be also converted to non-branched aldehydes and alcohols via the present process. To achieve this conversion, combined isomerization-hydroformylation may be carried out. This process uses an internal-to-terminal olefin isomerization step followed by a selective hydroformylation of the more reactive terminal olefin isomer. For example, in the case of 3-hexene, the following reactions are involved:

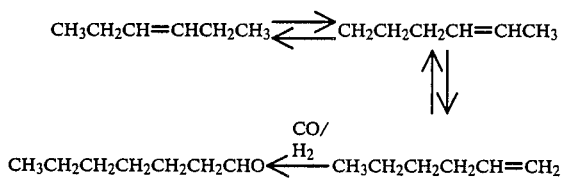

Due to its much greater reactivity, the terminal olefin is selectively hydroformylated even though its equilibrium concentration is smaller than those of the internal olefin isomers. The cobalt-phosphine-complex-based catalyst systems are particularly effective for coupling the isomerization and hydroformylation reactions.

$CO/H_2$ Synthesis Gas Feed

As a reactant gas for hydroformylating the olefin components of the present feed, mixtures of $H_2$ and CO, preferably in ratios ranging from 1-2 to 10-1, can be used. Ratios between 1 and 2 are preferred. When reacting higher olefins, most of the total reactor pressure is that of $H_2$ and CO. High $H_2$/CO pressures, particularly high CO partial pressures, usually stabilize the catalyst system. The CO as a ligand competes with the sulfur compound ligands for coordination with the transition metal to from the metal-CO complex catalyst. CO partial pressure affects the equilibria among catalyst complexes of different stability and selectivity. Thus it also affects the ratio of linear to branched products (n/i) and the extent of side reactions such as hydrogenation.

High CO partial pressures are particularly important in forming and stabilizing the desired carbonyl complex catalysts of high pressure cobalt hydroformylation. They stabilize the catalyst complex against deactivation by the sulfur compound components of the feed. In a preferred operation, the active catalyst system is produced at a low $H_2$/CO ratio. Thereafter, the catalyst is operated at increasing $H_2$/CO ratios.

The effect of CO partial pressure on the n/i ratio of aldehyde and alochol products is particularly important in the presence of rhodium complexes of trivalent phosphorus ligands, particularly phosphines. Phosphine ligands increase the strength of CO coordination to rhodium. Thus the need for increased CO partial pressure to stabilize the catalyst complex is reduced. Increased CO partial pressures result in multiple coordination of CO to rhodium, i.e., catalyst complexes leading to reduced n/i ratios. To produce products of high n/i ratios rhodium complexes containing only one CO per Rh are preferred. Thus in this case the partial pressure of CO is preferably below 500 psi.

Catalyst Complexes and Selective Feed Conversions

Catalysts suitable for use in this hydroformylation process include transition metal carbonyl complexes preferably selected from the group of Fe, Co, Rh, Ru, Ir and Os. The more preferred transition metals are rhodium, cobalt, ruthenium and iridium. Rhodium and cobalt complexes are most preferred. A preferred group of catalysts consists of transition metal carbonyl hydrides. Some of the carbonyl ligands of these complexes may be replaced by ligands such as trivalent phosphorus, trivalent nitrogen, and triorganoarsine and divalent sulfur compounds. Trivalent phosphorus ligands, and particularly triorganoposhines and phosphite esters are preferred.

The preferred triorganophosphine ligands include substituted and unsubstituted triaryl phosphines, diaryl alkyl phosphines, dialkyl aryl phosphines and trialkyl phosphines. These phosphines may be partially or fully open chain or cyclic, straight chain or branched. They may have various substituents, such as those disclosed in U.S. patent application Ser. No. 120,971 of Feb. 12, 1980 which is incorporated herein by reference.

In general, the stable but not directly active catalyst complexes of the present invention are coordinatively saturated transition metal carbonyl hydrides. They include metal carbonyl cluster hydrides. In case of Co, Rh and Ir they are preferably of the formula

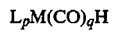

wherein L is a ligand, preferably P, N or As ligand, M is transition metal, p is 0 to 3 and q is 1 to 4, with the proviso that p+q=4. These complexes lead to catalytically active coordinatively unsaturated compounds via L and/or CO ligand dissociation

A preferred subgenus of complex catalysts consists of pentacoordinate trialkyl phosphine rhodium carbonyl hydrides of the general formula

wherein R is a $C_1$ to $C_{30}$ unsubstituted or substituted alkyl; x is 2 or 3 and y is 1 or 2, with the proviso that x+y is 4. The alkyl groups can be the same or different; straight chain or cyclic, substituted or unsubstituted. The trialkyl phosphine rhodium carbonyl complex subgenus of catalyst complexes shows outstanding thermal stability in the presence of excess trialkyl phosphine ligand even at low pressure. Thus, it can be advantageously employed at temperatures between 140°–200° C. under pressures ranging from 100 to 1000 psi. Tri-n-alkyl phosphine complexes of this type can be employed for the selective hydroformylation of Type I olefins.

In general, phosphorus ligands of low steric demand, such as tri-n-alkyl phosphines and n-alkyl diaryl diphenyl phosphines, can lead to high n/i product ratios derived from Type I olefins in rhodium catalyzed hydroformylation. This requires a high P/Rh ratio in the catalyst system and a low partial pressure of CO.

Trialkyl phosphine complexes having branching on their α- or/and β-carbons have increased steric demand. They tend to form catalyst complexes of structures which have increased reactivity toward Type II and Type III olefins. For example, the α-branched tricyclohexyl phosphine and the β-branched tri-i-butyl phosphine

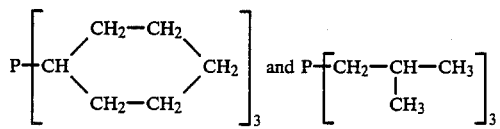

are attractive catalyst ligands of this type. These catalysts, while highly active, do not provide high n/i product ratios.

Another preferred type of phosphorus ligand for rhodium consists of alkyl diaryl phosphines of low steric demand. The tris-phosphine rhodium carbonyl hydride complexes of these ligands show a desired combination of operational hydroformylation catalyst stability and selectivity to produce high n/i product ratios.

In general, the hydrogenation activity of phosphine rhodium complexes is relatively low. Thus, in the presence of these complexes, aldehyde products of hydroformylation can be produced in high selectivity without much alcohol and/or paraffin formation, particularly at low temperatures.

Another subgenus of suitable catalyst complexes is that of pentacoordinate trialkyl phosphine cobalt carbonyl hydrides of the formula

wherein R is preferably a $C_1$ to $C_{30}$ alkyl as above, u is 1 or 2, v is 2 or 3 with the proviso that u+v is 4. Tri-n-alkyl phosphine ligands are particularly advantageous in these cobalt phosphine catalysts since they provide high selectivity in the production of normal alcohol products when hydroformylating the 1-n-olefin and linear internal olefin components of the present cracked feeds. Tri-n-alkyl phosphine ligands include those wherein the n-alkyl substituents are part of a cyclic structure including the phosphorus, e.g.,

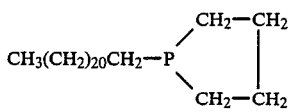

Using these catalysts it is preferred to operate at high temperatures. Thus the preferable temperatures are between 160° to 200° C. at pressures of 500 to 4500 psi. The more preferable pressure range is from 1000 to 3000 psi. Low medium pressures ranging from 1000 to 2000 psi are most preferred.

Another subgenus of catalysts is represented by cobalt carbonyl complexes free from phosphorus ligands. These catalysts include dicobalt octacarbonyl and tetracarbonyl cobalt hydride.

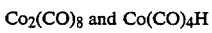

The latter compound is assumed to be an immediate precursor of catalytically active species. Cobalt carbonyl catalysts are stabilized by high $CO/H_2$ pressures ranging from 2000 to 6000 psi during hydroformylation. They are preferably used in the 100° to 180° C. temperature range. For a selective conversion of Type I olefins, lower temperatures up to 145° C. are used.

In the high pressure cobalt catalyzed reaction of the present process using high sulfur feeds, dicobalt octacarbonyl is converted to partially sulfur ligand substituted components as it is indicated by the following schemes.

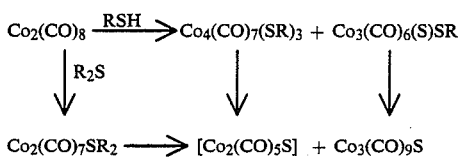

These and similar complexes and their hydride derivatives form equilibria with dicobalt octacarbonyl and tetracarbonyl cobalt hydride. The resulting catalyst system provides active catalyst species with or without sulfur. The sulfur containing species may also lead to insoluble and thus inactive CoS. The conditions of the present process, particularly the Co partial pressure, are set to suppress CoS formation.

In general, the transition metal complex hydroformylation catalysts of the present invention are employed in effective amounts to achieve the desired olefin conversion to aldehydes and/or alcohols. The catalyst concentration is typically higher in the present process using feeds of high sulfur content than in other similar processes using pure olefin feeds. The transition metal concentration can range from 0.001 to 5%. The more preferred concentrations primarily depend on the metal employed. Cobalt concentrations range from 0.01 to 5%, preferably from 0.01 to 5%, more preferably from 0.05 to 1%. Rhodium concentrations range from about 0.001 to 0.5%. Other factors determining the optimum catalyst concentration are the concentration and types of olefin in the feed and the desired olefin conversion. 1-n-olefins are generally the most reactive. For a complete conversion of branched olefins, higher catalyst concentrations are needed.

The phosphorus, nitrogen and arsenic containing catalyst ligands are employed in excess. High excess ligand concentrations have a stablizing effect on the catalyst complex. Particularly in the case of the phosphorus ligands, it is preferred to employ a minimum of 3 to 1 ligand to transition metal ratio. In the case of the phosphine rhodium complexes, the minimum P/Rh ratio is preferably greater than 10. P/Rh ratios can be as high as 1000. The sulfur-containing ligands may be provided in the feed.

The use of P-, N- and As-containing ligands, particularly phosphorus ligands, leads to increased catalyst stability and selectivity for linear product formation. At the same time activity is usually decreased. Thus, the choice of metal to ligand ratio depends on the desired balance of catalyst stability, selectivity and activity. The S-containing ligands can improve the aldehyde selectivity of the present process.

High Pressure Low Temperature Cobalt Catalyzed Process

The high pressure cobalt catalyzed hydroformylation in the absence of stabilizing added ligands such as phosphines is preferably carried out at low temperatures below 180° C. where the reduction of aldehyde products to alcohols and the aldol dimerization of aldehydes during hydroformylation is reduced.

The aldehyde primary products are generally of a semilinear character. The linear n-aldehydes are the largest single aldehyde type present in the products. The linearity of the alcohol hydrogenation products is of course determined by that of the parent aldehyde mixture. The linearity of the aldehyde products in turn is mainly dependent on the unique feed of the present process and the catalyst and conditions of the conversion. In the following the aldehyde product mixtures are further characterized particularly for the cobalt catalyzed hydroformylation.

The two major types of aldehydes are the n-aldehydes and the 2-methyl branched aldehydes. Most of the rest of the aldehydes are 2-ethyl or higher n-alkyl branched aldehydes. In general, the normal and the 2-methyl branched products preferably represent more than 40% of the total.

At the lower temperatures, between 100° and 145° C., the Type I olefins, major components of the present feeds, are not effectively isomerized to the internal, Type II olefins of lesser reactivity. Thus a high concentration of the most reaction, terminal, Type I olefins is maintained. In addition, the low temperatures favor a higher n/i ratio of the hydroformylation products of type I olefins:

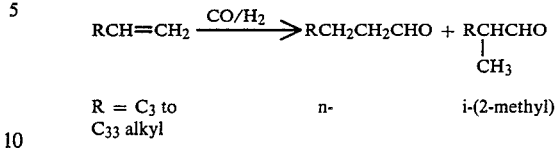

R = C₃ to C₃₃ alkyl    n-    i-(2-methyl)

Thus the use of low temperatures maximized the selectivity of the present process to the desired n-aldehyde and the 2-methyl substituted i-aldehyde products. From the Type II, linear internal olefins, 2-methyl, 2-ethyl, 2-propyl etc. substituted aldehydes are formed in decreasing concentrations as indicated by the following scheme (R=C₁ to C₃₁ alkyl):

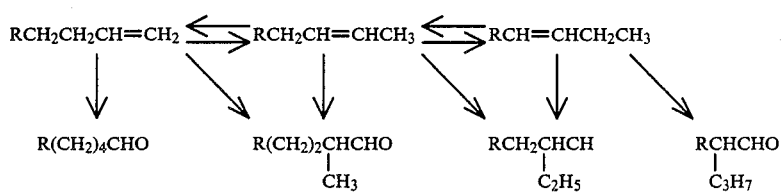

It was established by combined GC/MS studies that this product distribution of normal and 2-alkyl substituted i-aldehydes is a feature of the present process.

The low temperature cobalt catalyzed process results in high selectivity to aldehydes having one carbon more than their olefin precursors. Little aldol addition of the aldehyde products occurs during such hydroformylations. Thus the so called dimer by-products, consisting mainly of aldol condensation products are minimal. Similarly, the amounts of trimers, largely consisting of acetals and products of the Tischenko reaction of aldol adducts, is reduced.

A potential disadvantage of the low temperature operation is the relatively low reactivity of the Types II and III and particularly the Type III olefins. This can be overcome in a staged operation which involves the hydroformylation of Type I olefins in the low temperature regime and the hydroformylation of Type III olefins in the high temperature regime, between 145° and 180° C.

The low temperature operation can be effectively used for the selective conversion of Type I olefins to highly linear aldehydes. At low temperatures, the hydrogenation of the primary, aldehyde products to the corresponding secondary, alcohol products is insignificant. Thus the aldehydes can be separated and utilized as versatile chemical intermediates in various reactions.

The aldehyde and aldehyde plus alcohol products of hydroformylation are usually reduced to alcohols substantially free from aldehydes by hyrogenation. The hydrogenation catalysts are preferably sulfur resistant heterogeneous compositions based on cobalt and molybdenum. Such catalysts are preferably employed at high pressure and high temperature. Preferred pressures and temperatures are between about 2000–4000 psi (136 to 272 atm) and 149° to 260° C. (300°–500° F.).

Low temperature, high pressure, cobalt catalyzed hydroformylation can be advantageously carried out in the presence of added C₁ to C₆ monoalchols, diols or triols such as methanol, ethanol, 1,6-hexanediol, glycerol. In the presence of these lower alcohols, preferably employed in excess, the aldehyde products of hydroformylation undergo diacetal formation catalyzed by the acidic tetracarbonyl cobalt hydride. Using higher molecular weight alcohols, higher boiling acetals are formed. After the removal of the cobalt catalyst, these are readily separated from the unreacted components of the cracked distillate feed by fractional distillation. Thereafer, the acetals are hydrogenated in the presence of added water to produce the corresponding alcohols as indicated by the general reaction scheme

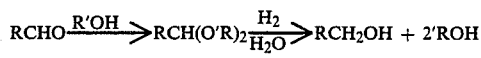

The added lower alcohols form water soluble cobalt complexes and thus also facilitate the removal of the cobalt catalyst after such combined hydroformylation acetalization reactions.

Continuous Operation

The preferred mode of operating the present processis obviously continuous rather than batchwise. The reaction conditions of continuous and batchwise operation are nevertheless similar. Continuous hydroformylation can be carried out in a single reactor or in a series of reactors using various methods of separating the catalyst from the products and unreacted feed components. Stirred, packed and plug flow reactors can be employed. Reactants are continuously introduced.

When adding stabilizing ligands (such as non-volatile phosphines) are used, the products and unreacted feed may be separated from the catalyst system by flash distillation. In low pressure hydroformylation, direct product flashoff from the reaction vessel can be employed. At increased pressures, a recirculation flash-off mode of operation is preferred. This latter method would include a continuous removal of liquid reaction mixture from the reactor. This liquid is then depressurized and flash distilled at atmospheric pressure or in vacuo. The residual solution of the catalyst may then be continuously returned to the reactor. Stabilizing ligands of hydrophilic character may be also employed to make the transition metal complex water, rather than hydrocarbon, soluble. This allows biphase catalysis in a stirred water-hydrocarbon feed mixture and a subsequent separation and return of the aqueous catalyst solution to the reaction mixture.

In the absence of stablizing ligands, the reaction mixture may be continuously withdrawn from the reactor and the transition metal carbonyl complex catalyst chemically converted to a water soluble, usually inactive form. After separation of the aqueous solution, the transition metal compound is reconverted to the precursor of the active catalyst which is then recycled to the reactor.

A variety of reactor schemes can be used for the optimum conversion of the olefin reactants in a continuous reactor. For instance, interconnected reactors may employ different catalyst systems. The first reactor may employ a phosphine-rhodium complex catalyst which selectively converts 1-n-olefins and employs direct product flash-off. This might be connected to a second reactor containing a phosphine-cobalt complex catalyst which converts the linear internal olefins via isomerization-hydroformylation. Alternatively cobalt alone may be used in the first reactor followed by a phosphine cobalt complex.

Hydroformylation-Aldolization

A further variation of the present process is the aldolization of the product aldehydes. A hydroformylation plus aldolization step in the presence of a base followed by a hydrogenation step converts a $C_{n+2}$ olefin to $C_{2n+6}$ aldehydes and alcohols. This is indicated in the following general scheme by the examples of Type I olefins.

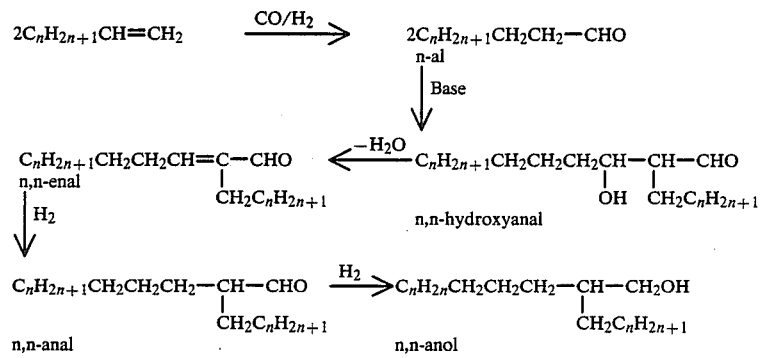

wherein the simple n-aldehyde product of hydroformylation is "n-al", the thermally unstable primary product of aldolization is "n,n-hydroxyanal", the unsaturated aldehyde resulting from aldolization is "n,n-enal", the selectively hydrogenated saturated aldehyde is "n,n-anal" and the final hydrogenated saturated alcohol is "n,n-anol". The n,n-prefixes indicate that both segments of the aldol compounds are derived from the terminal, i.e., normal, product of hydrogenation.

Minor iso-aldehyde components of the aldehyde product mixture can be also converted in a so-called cross-aldolization reaction with the normal aldehyde:

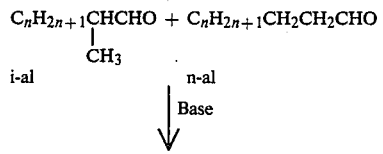

-continued

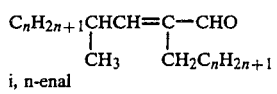
i, n-enal

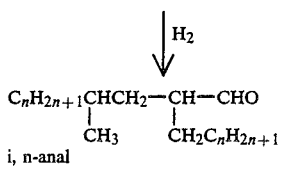
i, n-anal

The rate of the above cross-aldolization process is slower than that of the simple aldolization. However, the relative rate of cross-aldolization increases with increasing temperature and decreasing n/i aldehyde ratios. The latter can be achieved by the addition of extra i-aldehyde to the reaction mixture.

The aldolization step can be carried out separately by condensing the aldehyde product intermediates in the presence of a base catalyst. Hydroformylation and aldolization plus hydrogenation can be combined by carrying out the hydroformylation in the presence of the above-described transition metal complex based catalysts plus a base aldolization catalyst.

A preferred mode of combined hydroformylation-aldolization is carried out in the presence of trialkyl phosphine rhodium carbonyl hydride plus excess trialkyl phosphine hydroformylation catalyst system plus a base aldolization catalyst such as potassium hydroxide.

To carry out the present combined hydroformylation-aldolization process in the preferred homogeneous, liquid phase, solvent selection is important. The preferred solvent will dissolve all the widely different components of the reaction system. Solvency for the nonpolar olefin reactant and polar caustic catalyst and water by-product is therefore a compromise. Alcohols, particularly hydrocarbyloxyethyl alcohols are excellent choices. They may be of the formula, $$J(OCH_2CH_2)jOH$$

wherein $J=C_1$ to $C_4$ alkyl, preferably primary alkyl, most preferably methyl, $C_6$ to $C_{10}$ substituted or unsubstituted phenyl, preferably phenyl, j is 1 to 8, preferably 3 to 8. Desirable solvents include methoxytriglycol, $CH_3(OCH_2CH_2)_3OH$, and phenoxyethanol, $PhOCH_2$-$H_2OH$. In general, the weight proportion of the relatively nonpolar hydrocarbyl segment J to that of the highly polar oligo (-oxyethyl) alcohol segment determines the relative solvent power for the nonpolar versus polar components of the reaction mixture. As such, this type of a solvent can be readily optimized for any special application of the present process.

In a continuous combined hydroformylation-aldolization process, product flash-off is more difficult to realize because of the high boiling points of the aldol condensation products. Therefore, direct product flash-off is not generally feasible. Recirculation flash-off, aqueous catalyst separation and chemical catalyst recovery are preferred. Due to the high boiling point of the aldol condensation products, separation from the unreacted components of the distillate feed by fractional distillation is facilitated. Thus broader carbon range distillate feeds can provide reaction mixtures suitable for aldol aldehyde or aldol alcohol separation by fractional distillation.

Since high aldolization rates can be readily achieved in the combined process, the reaction parameters can be readily adjusted to provide either the unsaturated or saturated aldehydes as the major products. Short reaction times, and low olefin conversions, preferably below 50%, plus high base concentration, favor the unsaturated aldehyde. However, mostly the saturated aldol condensation product is desired. This is, of course, the favored high conversion product.

Due to the improved thermal stability of the present trialkyl phosphine rhodium complex hydroformylation catalyst, the aldol condensation products can be flashed off or distilled without affecting the catalyst. However, strong bases have an adverse effect on the thermal stability of the system. These can be either removed before distillation or replaced with weaker base aldolization catalysts such as amines and Schiff bases. For example, basic ion exchange resins can be filtered off. For known, applicable aldolization catalysts, reference is made to Volume 16, Chapter 1 of the monograph "Organic Reactions", edited by A. C. Cope et al., published by J. Wiley & Sons, Inc., New York, N.Y., 1968.

The preferred concentration of the strong organic base, i.e., alkali hydroxide, aldolization catalyst is low, between about 0.01 and 1%, preferably between 0.05 and 0.5%. Of course, smaller caustic concentrations have less adverse effect on the stability of the reaction system.

EXAMPLES

In the following, examples are provided to illustrate the claimed hydroformylation process, but not to limit the invention. Prior to the examples the cracked distillate feedstocks are described. The description of the feedstocks details the structural types and amounts of reactive olefins present, this information being a key component of the invention. Thereafter, the low and high pressure hydroformylation procedures used and the product workup are outlined. Then the examples of the actual hydroformylation experiments are given in groups according to the feeds and catalysts employed. The summarized results of these experiments are also provided in tables.

Feedstocks

The feedstocks used in the following examples were fractions of liquid distillates produced by Fluid-coking in the temperature range of 482° to 538° C. (900°–1000° F.). Fluid-coking is described in U.S. Pat. Nos. 2,905,629; 2,905,733 and 2,813,916 which were previously discussed. As a high temperature thermal cracking process, Fluid-coking produces distillate liquids and residual coke from vacuum residue. In Fluid-coking only the distillate products are utilized. The vacuum residue feeds and the thermal cracking step of Fluid-coking and Flexicoking are identical. However, the Flexicoking process is further integrated into the refinery by virtue of using the coke to manufacture low thermal value gas. Flexicoking is described in U.S. Pat. Nos. 3,661,543; 3,816,084; 4,055,484 and 4,497,705 which are incorporated as a reference.

The key factor in producing the present highly olefinic feed is the high temperature thermal cracking. However, another important factor is the origin and prior treatment of the petroleum residua to be cracked. The presence of the desired, major 1-n-olefin components of the present feed depend on the presence of n-alkyl groups in the feed. These olefins are formed by the cracking and dehydrogenation of n-alkyl aromatics and paraffins. In the past the molecular structure of higher boiling coker distillates was not known. Thus the desired feeds of the present invention were not recognized.

An important step of the present invention was the structural analysis and recognition of the preferred distillate feeds. Since these feeds are extraordinarily complex, several analytical techniques were employed. The feeds were analyzed using capillary gas chromatographs (GC) equipped with 50 m or 30 m fused silica columns to determine the individual components. A high resolution, 400 MHz, proton resonance spectrometer (NMR) was used to estimate the various types of hydrocarbons, particularly olefins. The structures of key feed components and products were determined by combined gas chromatography/mass spectrometry, GC/MS. Elemental and group analysis techniques were used to determine total sulfur, mercaptan sulfur and total nitrogen contents.

Coker Naphtha

The composition of the $C_4$ to $C_{12}$ coker naphtha distillate was analyzed by GC using a temperature programmed 50 m column. The key components of the mixture were identified by GC/MS, with the help of standards as required. The gas chromatogram obtained is shown in FIG. 1 with symbols indicating the 1-n-olefin and n-paraffin components of various carbon numbers. It is apparent from the figure that the main olefin components of the naphtha are 1-n-olefins, $C_4^=$ to $C_{12}^=$. The parent n-paraffins, $C_4°$ to $C_{12}°$ were found to be present in similar but usually smaller amounts. The corresponding 1-n-olefin to n-paraffin ratios are shown by Table I. In the $C_6$ to $C_{12}$ range these ratios range from about 1.1 to 2.1. In general, the 1-n-olefin to paraffin ratio increases with increasing carbon numbers.

TABLE I 1-n-Olefin Versus n-Paraffin Components of Fluid Coker Naphtha

| Carbon No. | Component, GC % | | Ratio, Olefin Paraffin |
|---|---|---|---|
| | 1-n Olefin | n- Paraffin | |
| 3 | 1.120 | 0.169 | 0.7101 |
| 4 | 1.193 | 0.307 | 0.6287 |
| 5 | 0.418 | 0.523 | 0.7992 |
| 6 | 1.298 | 0.924 | 1.4048 |
| 7 | 1.807 | 1.496 | 1.2079 |
| 8 | 2.223 | 1.960 | 1.1342 |
| 9 | 2.164 | 1.651 | 1.3107 |
| 10 | 2.215 | 1.483 | 1.4936 |
| 11 | 1.534 | 0.989 | 1.5511 |
| 12 | 0.623 | 0.299 | 2.0836 |
| 3–12 | 12.295 | 9.801 | 1.2545 |

As summarized by Table I, in the $C_3$ to $C_{12}$ range, the naphtha contained 12.3% 1-n-olefins and 9.8% n-paraffins. Thus, the overall 1-n-olefin to n-paraffin ratio was 1.25.

The ratio of 1-n-olefins to n-paraffins is a main factor indicating whether or not a given thermally cracked distillate is a suitable feed in the present process, particularly in case of the cobalt based catalysts. This ratio should be above 1, preferably above 1.2.

Lower cracking temperatures result in decreased olefin/paraffin ratios. For example, delayed coking which is carried out at a lower temperature than fluid coking gives distillates of lower ratios. An analysis of a naphtha fraction from a delayed coker gave an average of 0.3 1-n-olefin/n-paraffin ratio as it is shown by Table II.

TABLE II 1-n-Olefin versus n-Paraffin Components of Delayed Coker Naphtha

| Carbon No. | Component, GC % | | Ratio, Olefin Paraffin |
|---|---|---|---|
| | 1-n Olefin | n- Paraffin | |
| 6 | 1.956 | 5.008 | 0.3850 |
| 7 | 2.344 | 7.352 | 0.3188 |
| 8 | 1.879 | 6.707 | 0.2802 |
| 9 | 1.492 | 4.148 | 0.3596 |
| 10 | 0.374 | 0.994 | 0.3763 |
| 6–10 | 8.045 | 24.209 | 0.3323 |

A comparison of the olefin/paraffin ratios of Table I and Table II indicates that fluid coking provides an about 4 times greater olefin/paraffin ratio than delayed coking.

Many of the other components of the naphtha were also identified. Some of the illustrative details will be given in a discussion of certain distillate fractions.

The broad $C_3$ to $C_{12}$ coker naphtha fraction was fractionally distilled, using a column equivalent to 15 theoretical plates with reflux ratio of 10, to produce distillates rich in olefins and paraffins of a particular carbon number. The boiling ranges and amounts of the distillate fractions obtained on distilling the naphtha are shown by Tables III and IV. The 1-n-olefin and n-paraffin components and a few key aromatic hydrocarbons present are also shown. The results indicate that in the $C_5$ to $C_{10}$ range distillates containing about 15.1 to 29.6% of individual 1-n-olefins could be reproduced. In case of the higher boiling fractions, separation was more difficult and thus the maximum 1-n-olefin percentage in case of 1-dodecene was 12.7%. The separation of $C_{10}$, $C_{11}$ and $C_{12}$ fractions was adversely affected by the presence of water in the distillation vessel. This effect could be eliminated by removing the water in vacuo.

TABLE III 1-n-Olefin and n-Paraffin Components of $C_4$ to $C_8$ Distillate Fractions of Fluid Coker Naphtha Weight % Composition of Distillate Fractions and Starting Naphtha by Capillary GC

| | | Pentenes | | | Hexenes | | | Heptenes | | | Octenes | | |
|---|---|---|---|---|---|---|---|---|---|---|---|---|---|
| Fraction No.: | Trap | 1 | 2 | 3 | 4 | 5 | 6 | 7 | 8 | 9 | 10 | 11 | 12 | $C_3$–$C_{12}$ |
| Amount, g: | 705 | 590 | 526 | 698 | 951 | 1159 | 1854 | 3785 | 2508 | 1712 | 7920 | 2830 | 1985 | Starting |
| Bp. Up to °C.: | (23°) | −27° | 32° | −38° | −60° | 66° | −71° | −91° | −96° | −102° | −118° | −123° | −128° | Naphtha |
| °F.: | (74°) | −80° | −90° | −100° | −140° | −150° | −160 | −195° | −205° | −215° | −245° | −254° | −262° | −410° |
| $C_3^=$ $C_4^=$ | 21.5 | 1.1 | 0.3 | 0.1 | | | | | | | | | | 0.3 |
| 1-$C_4$ | 13.1 | 10.6 | 2.0 | 1.0 | 0.2 | | | | | | | | | 0.2 |
| $C_4°$ | 17.8 | 17.3 | 3.9 | 21.1 | 0.3 | | | | | | | | | 0.3 |
| 1-$C_5^=$ | 3.2 | 9.3 | 15.1 | 11.5 | 3.1 | 0.5 | 0.1 | | | | | | | 0.4 |
| $C_5°$ | 2.3 | 7.7 | 18.6 | 18.0 | 6.2 | 1.0 | 0.2 | | | | | | | 0.5 |
| 1-$C_6^=$ | | | | 0.1 | 16.1 | 29.6 | 16.3 | 3.4 | 0.2 | | | | | 1.3 |
| $C_6°$ | | | | | 3.0 | 15.6 | 16.3 | 3.9 | 0.3 | | | | | 0.9 |

TABLE III-continued 1-n-Olefin and n-Paraffin Components of $C_4$ to $C_8$ Distillate Fractions of Fluid Coker Naphtha Weight % Composition of Distillate Fractions and Starting Naphtha by Capillary GC

| | | Pentenes | | | | Hexenes | | | Heptenes | | | Octenes | | |
|---|---|---|---|---|---|---|---|---|---|---|---|---|---|---|
| Fraction No.: | Trap | 1 | 2 | 3 | 4 | 5 | 6 | 7 | 8 | 9 | 10 | 11 | 12 | $C_3$–$C_{12}$ |
| Amount, g: | 705 | 590 | 526 | 698 | 951 | 1159 | 1854 | 3785 | 2508 | 1712 | 7920 | 2830 | 1985 | Starting |
| Bp. Up to °C.: | (23°) | −27° | 32° | −38° | −60° | 66° | −71° | −91° | −96° | −102° | −118° | −123° | −128° | Naphtha |
| °F.: | (74°) | −80° | −90° | −100° | −140° | −150° | −160 | −195° | −205° | −215° | −245° | −254° | −262° | −410° |
| Cyclic $C_6$'s | | | | | 0.2 | 2.3 | 17.2 | 18.7 | 4.1 | 0.7 | | | | 1.7 |
| 1-$C_7$= | | | | | | | | 11.4 | 20.3 | 11.9 | 1.8 | | | 1.8 |
| $C_7$° | | | | | | | | 3.8 | 16.9 | 16.8 | 2.9 | 0.1 | | 1.5 |
| Toluene | | | | | | | | 0.2 | 1.5 | 10.6 | 26.7 | 6.7 | 2.3 | 3.4 |
| 1-$C_8$= | | | | | | | | | | | 7.5 | 16.6 | 12.0 | 2.2 |
| $C_8$° | | | | | | | | | | | 3.2 | 15.3 | 16.0 | 2.0 |
| Xylenes (m-, p-) | | | | | | | | | | | | 1.7 | 6.0 | 3.2 |
| 1-$C_9$= | | | | | | | | | | | | | | 2.2 |

1-$C_n$=: 1-n-olefin of a certain carbon number; $C_n$°: Normal paraffin of a certain carbon number.

TABLE IV 1-n-Olefin and n-Paraffin Components[a] of $C_9$ to $C_{12}$ Distillate Fractions of Fluid Coker Naphtha Weight % Composition of Distillate Fractions

| | Nonenes | | | | Decenes | | Undecenes | | | | |
|---|---|---|---|---|---|---|---|---|---|---|---|
| Fraction No. | 13 | 14 | 15 | 16 | 17 | 18 | 19 | 20 | Dodecenes | | |
| Amount, g | 10498 | 2280 | 1376 | 7979 | 4881 | 5793 | 5233 | 561 | 21 | | |
| Bp. Up to °C. | −145 | 149 | 153 | −168 | −177 | −190 | −199 | −210 | 1520 | Residue | |
| °F. | −290 | −300 | −307 | −335 | −350 | −374 | −390 | −410[b] | 425[c] | 3189 | |
| 1-$C_8$= | 2.2 | | | | | | | | | | |
| $C_8$° | 3.7 | | | | | | | | | | |
| Xylenes, m-, p- | 18.4 | 5.0 | 1.9 | 0.3 | | | | | | | |
| 1-$C_9$= | 6.3 | 18.9 | 12.0 | 2.0 | | | 0.4 | | | | |
| $C_9$° | 2.4 | 16.3 | 16.3 | 3.5 | | | | | | | |
| i-Propylbenzene | 0.3 | 2.2 | 2.5 | 0.7 | | | | | | | |
| 1-$C_{10}$= | | | | 7.1 | 15.8 | 1.8 | 0.8 | 1.7 | | | |
| $C_{10}$ | | | | 2.6 | 13.7 | 2.7 | | | | | |
| 1,2,3-Trimethylbenzene | | | | 1.1 | 7.3 | 2.4 | | | | | |
| 1-$C_{11}$= | | | | | | 8.4 | 8.3 | 2.9 | 0.4 | | |
| $C_{11}$° | | | | | | 4.2 | 9.0 | 0.6 | | | |
| Naphthalene | | | | | | | 0.8 | 5.9 | 5.1 | | |
| 1-$C_{12}$= | | | | | | | 0.6 | 6.2 | 12.7 | | |
| $C_{12}$° | | | | | | | 0.1 | 2.9 | 8.8 | | |
| 2-Methylnaphthanene | | | | | | | | | 0.4 | | |

[a] 1-$C_n$= and $C_n$° are symbols for n-olefins of a certain carbon number and n-paraffins of a certain carbon number, respectively.
[b] Atmospheric equivalent. The fraction was obtained between about 90 and 99° C. at 20 mm.
[c] Atmospheric equivalent; the fraction was obtained between 99 and 107° C. at 20 mm.

Figure 2:
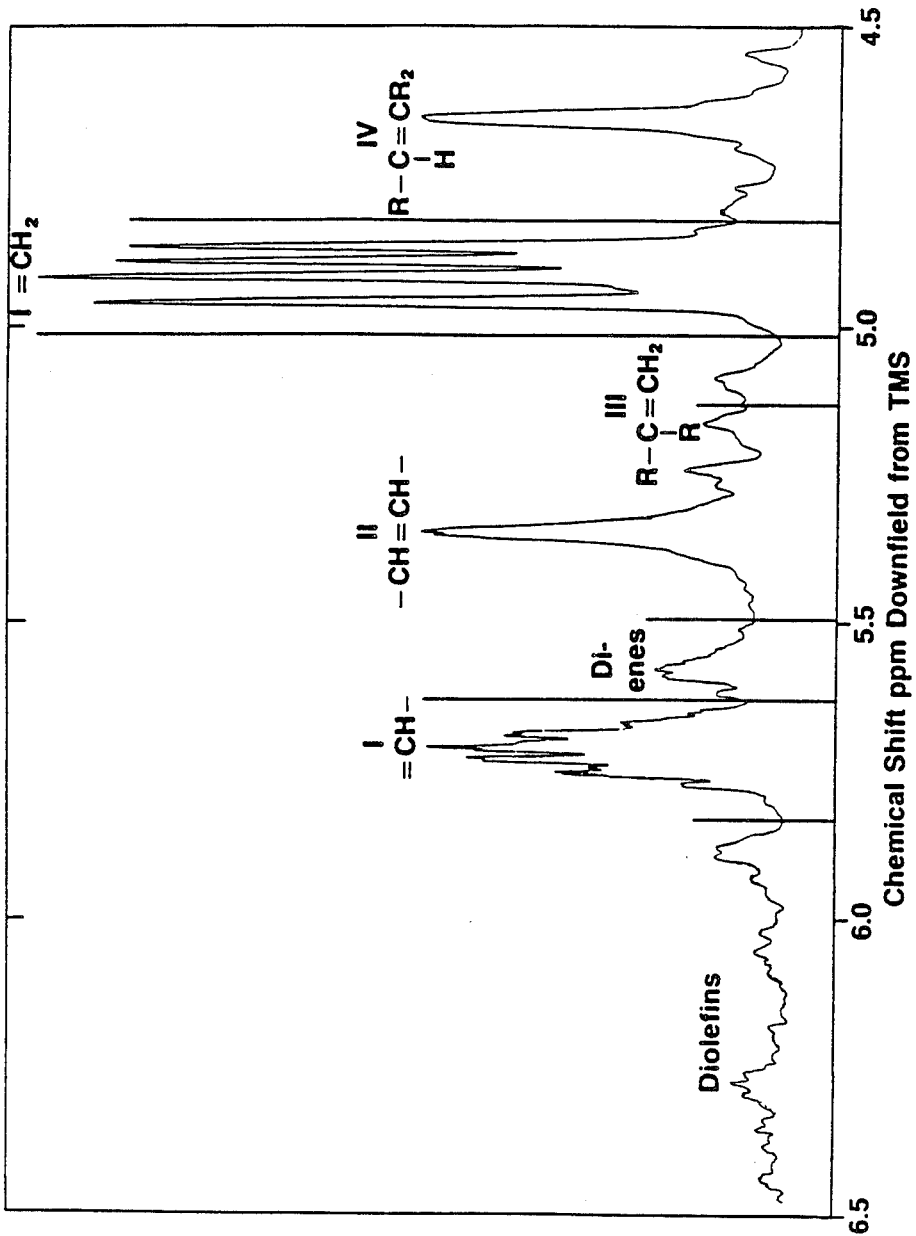
FIG. 2 shows the 400 MHz proton nuclear magnetic resonance spectrum of the olefinic protons of Fluid-coker naphtha feed, with an indication of the chemical shift regions of various types of olefins.

The $C_4$ to $C_{12}$ naphtha and selected distillate fractions thereof were also studied by proton NMR using a JEOL GX 400 MHz spectrometer. FIG. 2 shows the NMR spectrum of the olefinic region of the naphtha with an indication of the chemical shift regions assigned to the vinylic protons of various types of olefins. A quantitative determination of the olefinic protons of the various types of olefins was used to estimate olefin linearity. The relative mole percentages of olefins of varying carbon number were calculated on the basis of amounts of the different types of olefinic protons. The results of these calculations are shown in Table V.

The data of Table V show that the Type I olefins, i.e., monosubstituted ethylenes, are the major type of olefins in all the distillate fractions as well as in the starting $C_4$–$C_{12}$ naphtha. The percentage of Type I olefins in the distillation residue is, however, reduced to less than half of the original. It is assumed that this result is due to 1-n-olefin conversion during the high temperature distillation. Minor variations, between 32 and 50%, are also observed in Type I olefin content of distillate cuts. The reasons for this variation are unknown. The only Type I olefins indicated in the $C_8$ and higher carbon fractions are 1-n-olefins.

The second largest olefin type present in the naphtha and its distillate consists of 1,2-disubstituted ethylenes. The percentage of these Type II olefins varies between 18 and 26%. Most, if not all, of these olefins are linear internal olefins.

Type III olefins, i.e., 1,1-disubstituted ethylenes were found to be present in amounts ranging from 12 to 17%. The major olefins of this type were 2-methyl substituted terminal olefins. On the basis of MS studies of aldehydes derived from these olefins, it appears that their branching occurs mostly at the vinylic carbon.

Type IV olefin, i.e., trisubstituted ethylenes, were the smallest monoolefin components of these distillates. Their relative molar concentration is in the 6 to 12% range. Interestingly, the $C_8$ fractions contained the least of these olefins among the fractions examined.

TABLE V

Relative Amounts of Various Types of Olefins in Fluid Coker Naphtha Determined by 400 MHz Proton Magnetic Resonance Spectroscopy

| Naphtha Carbon No. | Mole Percentage Distribution of Various Types of Olefins | | | | | | | | | |
|---|---|---|---|---|---|---|---|---|---|---|
| | $C_4$-$C_{12}$ | $C_5$ | $C_6$ | $C_7$ | $C_8$ | $C_8$ | $C_9$ | $C_{10}$ | $C_{11}$ | $C_{12}$ | Residue |
| | | | | | Boiling Point, °F. | | | | | | |
| Initial: | — | 80– | 140– | 195 | 245– | 254– | 293– | 335– | 374– | 410– | 425– |
| Final: | –410 | –100 | –150 | 205 | –257 | –262 | –30 | 359 | –390 | –425 | — |
| Olefin I: —CH=$CH_2$ | 37 | 31 | 50 | 42 | 36 | 32 | 44 | 43 | 39 | 36 | 16 |
| II: —CH=CH— | 20 | 25 | 18 | 25 | 26 | 26 | 22 | 22 | 23 | 28 | 28 |
| III: =C=$CH_2$ | 17 | 13 | 15 | 14 | 22 | 22 | 14 | 14 | 12 | 11 | 15 |
| IV: =C=CH— | 12 | 22 | 10 | 8 | 6 | 07 | 08 | 12 | 10 | 11 | 21 |
| Conjugated Diolefin[a] | 14 | 10 | 8 | 11 | 11 | 13 | 12 | 15 | 16 | 14 | 20 |

[a]The conjugated diene values are only approximate.

Type V olefins, i.e., tetrasubstituted ethylenes, could not be determined by proton NMR. They are of little interest in the present invention since they are apparently unreactive in hydroformylation.

Finally, Table V also lists small but significant quantities (8–16%) of conjugated diolefins. The amounts listed for these olefins are approximate because conjugated olefins may have a different number of vinylic hydrogens per molecule dependent on the site of conjugation and the presence of branching at vinylic sites.

The NMR spectra of naphtha fractions were also analyzed in the area of aromatic and paraffinic protons to estimate the amounts of olefins. Table VI summarized the results. It shows the percentage distribution of various types of hydrogens. From this distribution and the elemental analyses of these fractions, the weight percentage of various types of compounds was estimated.

The type I olefins, mostly 1-n-olefins were estimated to be present in these fractions in the range of 18.7 to 28.3%. These percentages depend on both the carbon number and the particular usually narrow boiling range of the olefinic fractions studied. In the $C_6$ to $C_{10}$ range these values for the Type I olefins approximately correspond to the values obtained for 1-n-olefin by GC.

The total olefin content of these fractions is in the 47 to 62% range as determined by NMR. It is noted that the conjugated diolefins are included in this percentage since they are converted to monoolefins under hydroformylation conditions or by a prior mild hydrogenation. The amounts of paraffins are generally decreasing with increasing carbon number while the amounts of the aromatics are generally increasing.

To illustrate the detailed composition of the present naphtha feeds, more detailed data are provided on the $C_8$ and $C_{10}$ fractions on the basis of GC and GC/MS analyses.

Table VII shows the composition of two $C_8$ fractions. It is apparent that beside the major 1-octene component, there are significant quantities of all the linear internal octene isomers. The tans isomers of octene-2,-3, and 4 were identified. 2-Methylheptene-1 was also identified as the largest single branched octene. Toluene, ethylbenzene and xylenes were also present.

TABLE VI

Hydrogen Type Distribution Found and Olefins, Paraffins, Aromatics Estimated in Fluid Coker Naphtha by 400 MHz Proton Magnetic Resonance Spectroscopy

| Fraction Carbon Number | Boiling Range °C. | Hydrogen Distribution, Found % | | | | | | | Compound Types Estimated % | | | | | | | Total Olefins |
|---|---|---|---|---|---|---|---|---|---|---|---|---|---|---|---|---|
| | | Olefin Types | | | | Conj. Diene | Par- affins | Arom- atics | Olefin Types | | | | Conj. Diene | Par- affins | Arom- atics | |
| | | I | II | III | IV | | | | I | II | III | IV | | | | |
| 6 | 60–66 | 6.75 | 1.58 | 1.32 | 0.44 | 1.01 | 88.54 | 0.37 | 28.3 | 9.9 | 8.3 | 5.5 | 4.1 | 42.8 | 1.1 | 56.1 |
| 7 | 91–96 | 5.53 | 2.18 | 1.26 | 0.33 | 1.51 | 87.42 | 1.89 | 26.2 | 15.5 | 8.9 | 4.6 | 6.9 | 32.7 | 5.2 | 62.1 |
| 8 | 118–123 | 3.27 | 1.57 | 1.34 | 0.18 | 1.14 | 90.74 | 2.39 | 17.1 | 12.3 | 10.6 | 2.8 | 4.5 | 46.5 | 6.2 | 47.3 |
| 9 | 145–149 | 4.58 | 1.55 | 1.00 | 0.28 | 1.23 | 88.03 | 3.34 | 26.2 | 13.4 | 8.6 | 4.8 | 7.1 | 26.3 | 13.6 | 60.1 |
| 10 | 168–177 | 3.28 | 1.11 | 0.74 | 0.23 | 0.97 | 89.97 | 3.70 | 20.8 | 10.6 | 7.0 | 4.4 | 6.0 | 33.9 | 17.3 | 48.8 |
| 11 | 190–199 | 1.11 | 0.57 | 0.25 | 1.13 | 1.13 | 89.75 | 4.37 | 19.1 | 11.2 | 5.8 | 5.1 | 7.5 | 28.7 | 22.6 | 48.7 |
| 12 | 210–218 | 2.39 | 1.25 | 0.47 | 0.24 | 0.90 | 89.03 | 6.02 | 18.7 | 14.0 | 7.1 | 4.5 | 7.0 | 23.5 | 25.2 | 51.3 |
| 4–12 Feed | | 4.26 | 1.57 | 1.29 | 0.45 | 1.66 | 85.52 | 5.27 | | | | | | | | |
| 12+ Residue | 425+ | 0.91 | 1.03 | 0.55 | 0.40 | 1.12 | 91.19 | 4.80 | | | | | | | | |

TABLE VII

Major Olefin, Paraffin and Aromatic Hydrocarbon Components of Distillate Fractions of Fluid Coker Naphtha in the $C_8$ Range

| | Weight % Composition by GC | |
|---|---|---|
| Designation of Fraction | 1-Octene Rich | n-Octane Rich |
| Fraction No. | 11 | 12 |
| Quantity, g | 2072 | 1034 |
| Boiling Point Range, | | |
| °F. | 245–254 | 254–262 |
| °C. | 118–123 | 123–128 |
| | Others % / Olefins % | Olefins % / Others % |
| Toluene | 4.3 | 1.3 |
| 2-Methylheptene-1 | 6.3 | 3.2 |
| Octene-1 | 18.5 | 10.3 |
| trans-Octene-4 | 1.0 | 0.6 |
| trans-Octene-3 | 2.1 | 1.3 |
| n-Octane | 19.9 | 16.3 |
| trans-Octene-2 | 3.6 | 2.8 |
| cis-Octene-2 | 1.6 | 1.8 |
| Ethylbenzene | 0.6 | 6.1 |
| m-Xylene | 0.1 | 5.1 |
| p-Xylene | | 1.8 |
| o-Xylene | | 0.8 |
| Nonene-1 | | |
| Sum of Identified Compounds | 24.9 / 33.1 | 20.1 / 31.4 |

One fraction is richer in 1-n-octene, the other in n-octane. The sum of identified olefins in these fractions is 33.1% and 20.1%, respectively. Some of the octene isomers were not identified. The first fraction richer in olefins was used as the feed in the $C_8$ naphtha hydroformylation experiments.

Figure 3:
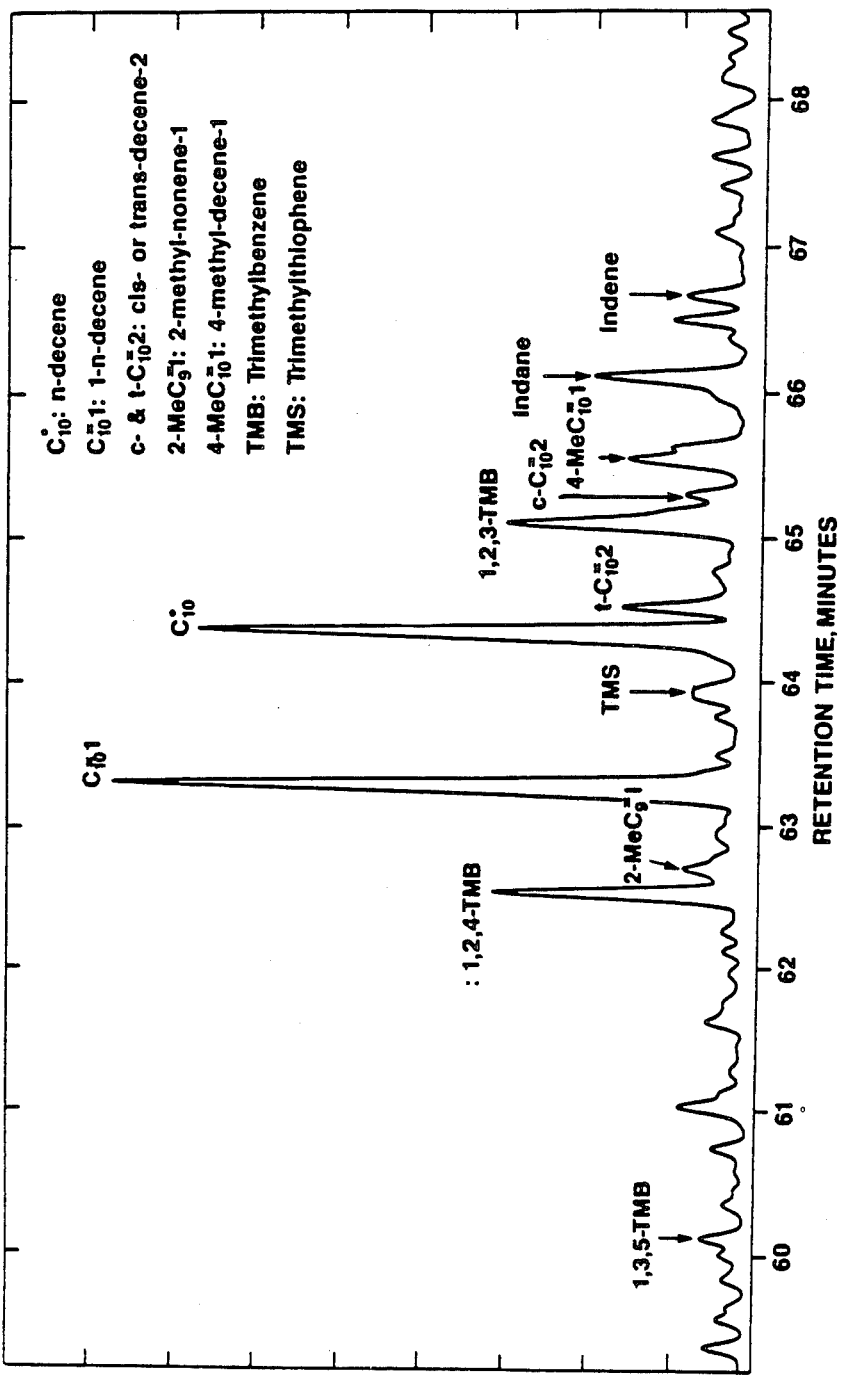
FIG. 3 shows the capillary gas chromatogram of the $C_{10}$ fraction of a Fluid-coker naphtha feed, with an indication of the major olefin, paraffin and aromatic components.

FIG. 3 illustrates the composition of the $C_{10}$ naphtha fraction. As it is indicated, besides the main 1-n-decene component several of the linear decenes and 2-methyl nonene-1 were identified. It was also shown that indene, a reactive, aromatic cycloolefin, is also present in this fraction. The main aromatic hydrocarbon components are trimethylbenzenes and indane.

The naphtha and its distillate fractions were also analyzed for sulfur and nitrogen compounds. Table VIII shows the carbon, hydrogen mercaptan and total sulfur plus total nitrogen contents.

The mercaptan content of the $C_8$ and higher fractions is surprisingly low compared to the high total sulfur content when determined by mercaptan titration by silver nitrate. It is believed that this is in part due to the facile cooxidation of mercaptans and activated olefins. The total sulfur content generally increased with the carbon number of the distillates from the $C_6$ fraction upward. Assuming the sulfur compounds of the various fractions had two fewer carbons per molecule than the corresponding hydrocarbon compounds, it was calculated that in the $C_5$ to $C_{12}$ range the approximate percentage of sulfur compounds has increased from 0.4% to 7%. In contrast to sulfur, the total nitrogen content of the $C_4$ to $C_{12}$ fractions was generally less than 160 ppm.

The mercaptan content of the two combined $C_8$ fractions (shown in Table V) was also determined by difference. At first, the total sulfur was determined by sulfur specific GC. Then the mercaptans were removed by precipitating them as silver mercaptides.

Thus this analysis provided a total sulfur content of 5560 ppm and a mercaptan content of 568. The main group of sulfur compounds were thiophenes in a concentration of 3781 ppm.

Coker Gas Oil

Similar characterizations were performed on a light coker gas oil produced by the same Fluid-coking unit from which the coker naphtha was taken.

Figure 4:
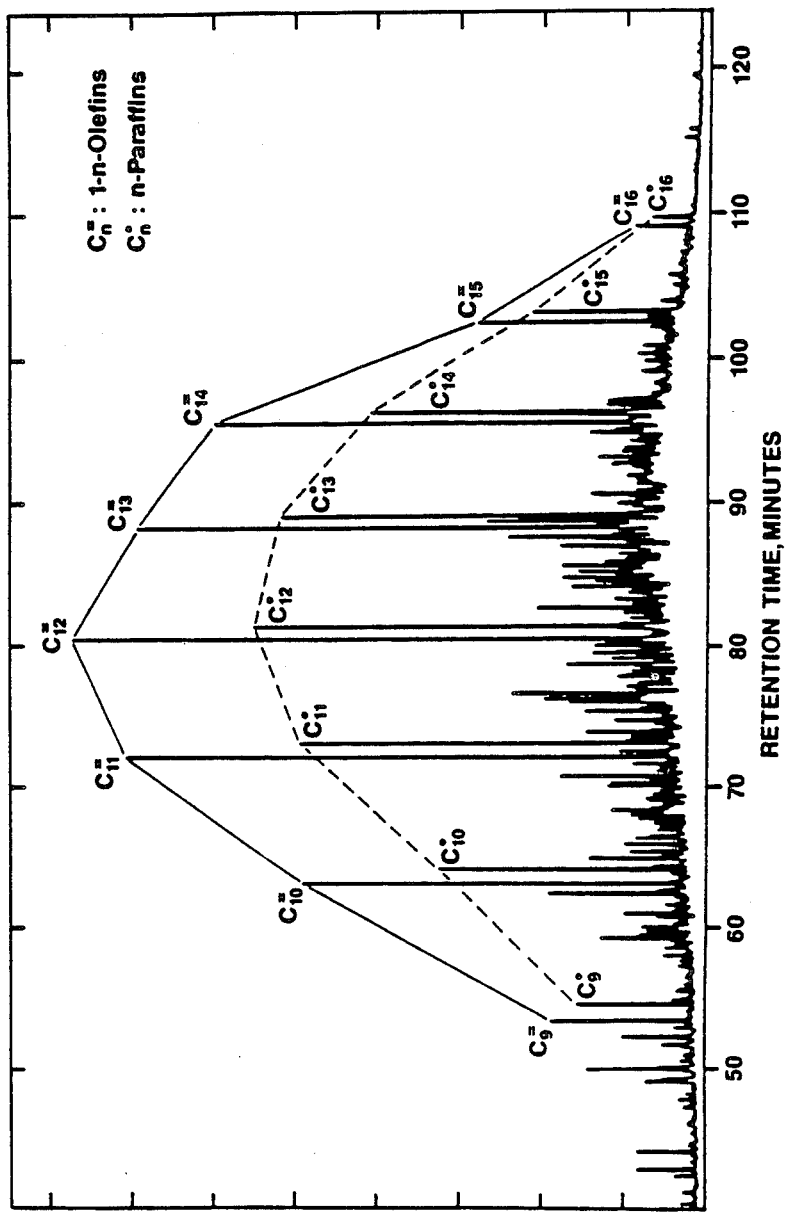
FIG. 4 shows the capillary gas chromatogram of the light Fluid-coker gas oil feed in the $C_9$–$C_{16}$ range, with an indication of the major 1-n-olefin and paraffin components.

FIG. 4 shows the capillary GC of the light gas oil in the $C_9$ to $C_{16}$ range. About 90% of the components are in the $C_{10}$ to $C_{15}$ carbon range. The $C_{11}$ to $C_{13}$ components are particularly large. Obviously, there is some overlap between this composition and that of the broad cut naphtha.

As it is indicated by the symbols of the figure, the main components are the 1-n-olefins and the n-paraffins. In general, the concentrations of the 1-n-olefins are greater than those of the corresponding paraffins. The 1-n-olefin to n-paraffin ratio is apparently maintained with increasing carbon numbers.

The light gas oil fraction was fractionally distilled to produce narrow cut distillates of a particular carbon number. The fractions obtained were then analyzed by GC. The data are summarized in Tables IX and X. The tables show the amounts of the individual cuts, the percentage concentration of the main paraffin and olefin components and separately list the heart cuts of particularly high content of a 1-n-olefin of a certain carbon number. These heart cuts were utilized in subsequent hydroformylation experiments.

The data of the tables show that 54% (44,939 g) of the distillates were in the $C_{12}$–$C_{15}$ olefin range. It is noted

TABLE VIII

| | Elemental Analyses of Distillate Fractions of Fluid Coker Naphtha | | | | | | | | | |
|---|---|---|---|---|---|---|---|---|---|---|
| | Carbon Hydrogen Sulfur and Nitrogen Content of Naphtha and its Fractions | | | | | | | | | |
| Naphtha Carbon Number | $C_4$–$C_{12}$ | $C_5$ | $C_6$ | $C_7$ | $C_8$ | $C_9$ | $C_{10}$ | $C_{11}$ | $C_{12}$ | Residue |
| | | | | | Boiling Point, °F.: | | | | | |
| Initial | — | 80– | 140– | 195– | 245– | 290– | 335– | 374– | 410– | 425– |
| Final | –410 | –100 | –150 | –205 | –257 | –300 | –350 | –390 | –425 | — |
| Carbon, % | | | 85.64 | 85.81 | 85.83 | 86.10 | 86.41 | 86.11 | 85.98 | 85.23 |
| Hydrogen, % | | | 14.39 | 14.01 | 13.49 | 13.18 | 12.95 | 12.39 | 12.33 | 10.75 |
| Mercaptan Sulfur (SH), ppm | 600 | 1770 | 850 | 450 | 80 | 20 | 60 | 30 | 100 | 490 |
| Total Sulfur, ppm | 8900 | 1700 | 1300 | 2200 | 5100 | 5900 | 8800 | 12,000 | 13200 | — |
| Total Nitrogen, ppm | 159 | 141 | 46 | 25 | 45 | 158 | 134 | 135 | 136 | 1022 |
| % SH (100 SH/Total) | 6.74 | ~100 | 65.38 | 20.45 | 1.57 | 0.34 | 0.68 | 0.25 | 0.76 | |
| Total Sulfur Compounds, % | | 0.40 | 0.36 | 0.71 | 1.86 | 2.42 | 3.99 | 5.96 | 7.14 | |

*The percentages of sulfur compounds in the various distillate fractions were calculated, assuming that they contain 2 carbon less per molecule than the hydrocarbon compounds of the fraction of a certain carbon number.

Based on such an analysis, the following ppm concentrations were obtained for the various sulfur compounds in the order of their retention times: 2-methyl- and 3-methyl thiophenes, 962 and 612; n-pentane and n-hexanethiols, 106 and 78; $C_6$ branched thioether, 200; 1-hexanethiol, 384; 2,5- 2,4-, 2,3-, 3,4-dimethylthiophenes, 1245, 945, 728, 289; unknown sulfur compounds, 11.

that the percentage values for the 1-n-olefin and n-paraffin components are relative. Absolute values could not be determined. With the increasing molecular weight of these fractions, the number of isomers is sharply increasing. Thus the GC resolution is decreased and absolute accuracy decreased.

TABLE IX

$C_7$–$C_{11}$ Distillate Fractions of Light Coker Gas Oil

| Fraction No. E-7315 | Boiling Range, °F. Atmospheric (Calculated) | Boiling Range, °F. Vacuum Found/mm | Weight % of Total | Weight Amount g | Main Components, Carbon No. & % 1-n-Olefin | Main Components, Carbon No. & % n-Paraffin | Main Components, Carbon No. & % 1-n-Olefin | Main Components, Carbon No. & % n-Paraffin | Combined Heart Cuts Wt. % of Total | Combined Heart Cuts Amount g | Combined Heart Cuts Carbon Number | Combined Heart Cuts 1-n-Olefin % | Combined Heart Cuts n-Paraffin % |
|---|---|---|---|---|---|---|---|---|---|---|---|---|---|
| III | –250/750 | — | 1.95 | 1608 | $C_7^=$ 4.8 | $C_7^\circ$ 4.7 | | | | | | | |
| IV | 250–262/750 | — | 0.45 | 373 | $C_8^=$ 10.8 | $C_8^\circ$ 11.1 | $C_8^=$ 4.0 | $C_8^\circ$ 3.0 | 0.45 | 373 | 8 | 10.8 | 11.8 |
| V | 262–293/750 | — | 1.69 | 1393 | $C_8^=$ 3.1 | $C_8^\circ$ 3.9 | | | | | | | |
| VI | 293–307/750 | — | 1.38 | 1132 | $C_9^=$ 12.5 | $C_9^\circ$ 11.9 | $C_9^=$ 6.5 | $C_9^\circ$ 3.4 | 1.38 | 1132 | 9 | 12.5 | 11.9 |
| VII | 307–3331/750 | — | 3.58 | 2944 | $C_9^=$ 4.9 | $C_9^\circ$ 5.4 | | | | | | | |
| VIII | 331–335/750 | — | 0.81 | 667 | $C_9^=$ 1.3 | $C_9^\circ$ 1.6 | | | | | | | |
| IX | 335–345/750 | — | 2.39 | 1965 | $C_9^=$ 0.7 | $C_9^\circ$ 0.7 | $C_{10}^=$ 9.9 $C_{10}^=$ 15.3 $C_{10}^=$ 18.3 $C_{11}^=$ 1.7 $C_{11}^=$ 19.5 $C_{11}^=$ 19.5 $C_{11}^=$ 12.7 | $C_{10}^\circ$ 3.8 $C_{10}^\circ$ 9.17 $C_{10}^\circ$ 13.7 $C_{11}^\circ$ 3.4 $C_{11}^\circ$ 10.5 $C_{11}^\circ$ 10.5 $C_{11}^\circ$ 4.5 | 2.39 | 1965 | 10 | 18.3 | 13.7 |
| X | 345–355/750 | — | 1.90 | 1560 | $C_{10}^=$ 10.6 | $C_{10}^\circ$ 8.5 | | | | | | | |
| XI | 355–365/750 | — | 2.30 | 1892 | $C_{10}^=$ 5.3 | $C_{10}^\circ$ 4.9 | | | | | | | |
| XII | 365–371/750 | — | 2.66 | 2189 | $C_{10}^=$ 2.9 | $C_{10}^\circ$ 2.9 | | | | | | | |
| XIII | (371–375/At) | –220/50 | 1.77 | 1458 | $C_{10}^=$ 2.5 | $C_{10}^\circ$ 2.5 | | | 7.65 | 6290 | 11 | 19.5 | 10.2 |
| XIV | (375–385/At) | 220–229/50 | 3.58 | 2947 | $C_{11}^=$ 22.8 | $C_{10}^\circ$ 11.8 | | | | | | | |
| XV | (385–395/At) | 229–238/50 | 3.66 | 3011 | $C_{11}^=$ 6.6 | $C_{11}^\circ$ 13.3 | | | | | | | |
| XVI | (395–405/At) | 238–246/50 | 3.58 | 2946 | $C_{11}^=$ 1.3 | $C_{11}^\circ$ 3.1 | $C_{12}^=$ 2.1 | $C_{12}^\circ$ 0.3 | | | | | |

TABLE X $C_{12}$–$C_{16}$ Distillate Fractions of Light Fluid Coker Oil

| Fraction No. E-7315 | Boiling Range, °F. Atmospheric (Calculated) | Boiling Range, °F. Vacuum Found/mm | Weight % of Total | Weight Amount g | Main Components, Carbon No. & % 1-n-Olefin | Main Components, Carbon No. & % n-Paraffin | Combined Heart Cuts 1-n-Olefin | Combined Heart Cuts n-Paraffin | Combined Heart Cuts Wt. % of Total | Combined Heart Cuts Amount g | Combined Heart Cuts Carbon Number | Combined Heart Cuts 1-n-Olefin % | Combined Heart Cuts n-Paraffin % |
|---|---|---|---|---|---|---|---|---|---|---|---|---|---|
| XVII | 405–412 | –213/20 | 3.73 | 3070 | $C_{12}^= $ 13.3 | $C_{12}^°$ 4.4 | | | | | | | |
| XVIII | 412–415 | 213–216/20 | 1.70 | 1401 | $C_{12}^= $ 25.7 | $C_{12}^°$ 12.6 | | | | | | | |
| XIX | 415–423 | 216–222/20 | 3.72 | 3060 | $C_{12}^= $ 22.5 | $C_{12}^°$ 23.5 | | | 10.09 | 8300 | 12 | 18.8 | 16.4 |
| XX | 425–425 | 222–2224/20 | 0.93 | 769 | $C_{12}^= $ 13.3 | $C_{12}^°$ 27.7 | | | | | | | |
| XXI | 425–432 | 224–230/20 | 3.61 | 2967 | $C_{12}^= $ 5.4 | $C_{12}^°$ 10.5 | | | | | | | |
| XXII | 432–435 | 230–232/20 | 1.28 | 1050 | $C_{12}^= $ 0.8 | $C_{12}^°$ 4.1 | | | | | | | |
| XXIII | 435–442 | 232–238/20 | 3.82 | 3146 | $C_{13}^= $ 4.0 | $C_{13}^°$ 0.9 | | | | | | | |
| XXIV | 442–445 | 238–242/20 | 2.07 | 1700 | $C_{13}^= $ 15.9 | $C_{13}^°$ 6.2 | | | | | | | |
| XXV | 445–448 | –216/10 | 3.81 | 3134 | $C_{13}^= $ 23.0 | $C_{13}^°$ 12.2 | | | 10.20 | 8387 | 13 | 19.7 | 18.2 |
| XXVI | 448–455 | 216–221/10 | 3.62 | 2977 | $C_{13}^= $ 23.1 | $C_{13}^°$ 26.6 | | | | | | | |
| XXVII | 455–455 | 221–222/10 | 0.70 | 576 | $C_{13}^= $ 12.2 | $C_{13}^°$ 27.8 | | | | | | | |
| XXVIII | 455–465 | 221–230/10 | 3.81 | 3134 | $C_{13}^= $ 5.2 | $C_{13}^°$ 12.5 | | | | | | | |
| XXIX | 465–472 | 230–236/10 | 3.05 | 2506 | $C_{13}^= $ 0.7 | $C_{13}^°$ 2.2 | | | | | | | |
| XXX | 472–475 | 236–238/10 | 1.15 | 947 | $C_{14}^= $ 13.0 | $C_{14}^°$ 4.7 | | | | | | | |
| XXXI | 475–481 | 238–243/10 | 3.75 | 3086 | $C_{14}^= $ 19.8 | $C_{14}^°$ 10.2 | $C_{14}^= $ 4.8 | $C_{14}^°$ 1.2 | 7.05 | 5803 | 14 | 20.8 | 16.8 |
| XXXII | 481–485 | 243–246/10 | 3.30 | 2717 | $C_{14}^= $ 21.9 | $C_{14}^°$ 24.3 | | | | | | | |
| XXXIII | 485–495 | –229/5 | 3.27 | 2692 | $C_{14}^= $ 4.5 | $C_{14}^°$ 13.6 | | | | | | | |
| XXXIV | 495–505 | 229–237/5 | 2.66 | 2187 | $C_{14}^= $ 0.3 | $C_{14}^°$ 0.3 | | | | | | | |
| XXXV | 505–515 | 237–245/5 | 0.86 | 709 | $C_{15}^= $ 35.0 | $C_{15}^°$ 31.2 | | | 4.63 | 3810 | 15 | 24.7 | 28.2 |
| XXXVI | 517–522 | 245–273/5–8 | 3.78 | 3111 | $C_{15}^= $ 23.2 | $C_{15}^°$ 27.6 | $C_{16}^= $ 3.4  $C_{16}^°$ 2.3 | | | | | | |
| XXXVII | 525–535 | –242/3 | 1.96 | 1614 | $C_{16}^= $ 16.0 | $C_{16}^°$ 21.7 | $C_{17}^= $ 3.6  $C_{17}^°$ 3.1 | | | | | | |
| Total Distillates Tables I & II | | | 88.31 | 72638 | | | | | 49.50 | 35.960 | | | |
| XXXVIII Distillation Residue | | | 11.69 | 9620 | | | | | | | | | |

Nevertheless, it appears at least in a qualitative sense that the high 1-n-olefin concentrations are maintained.

Figure 5:
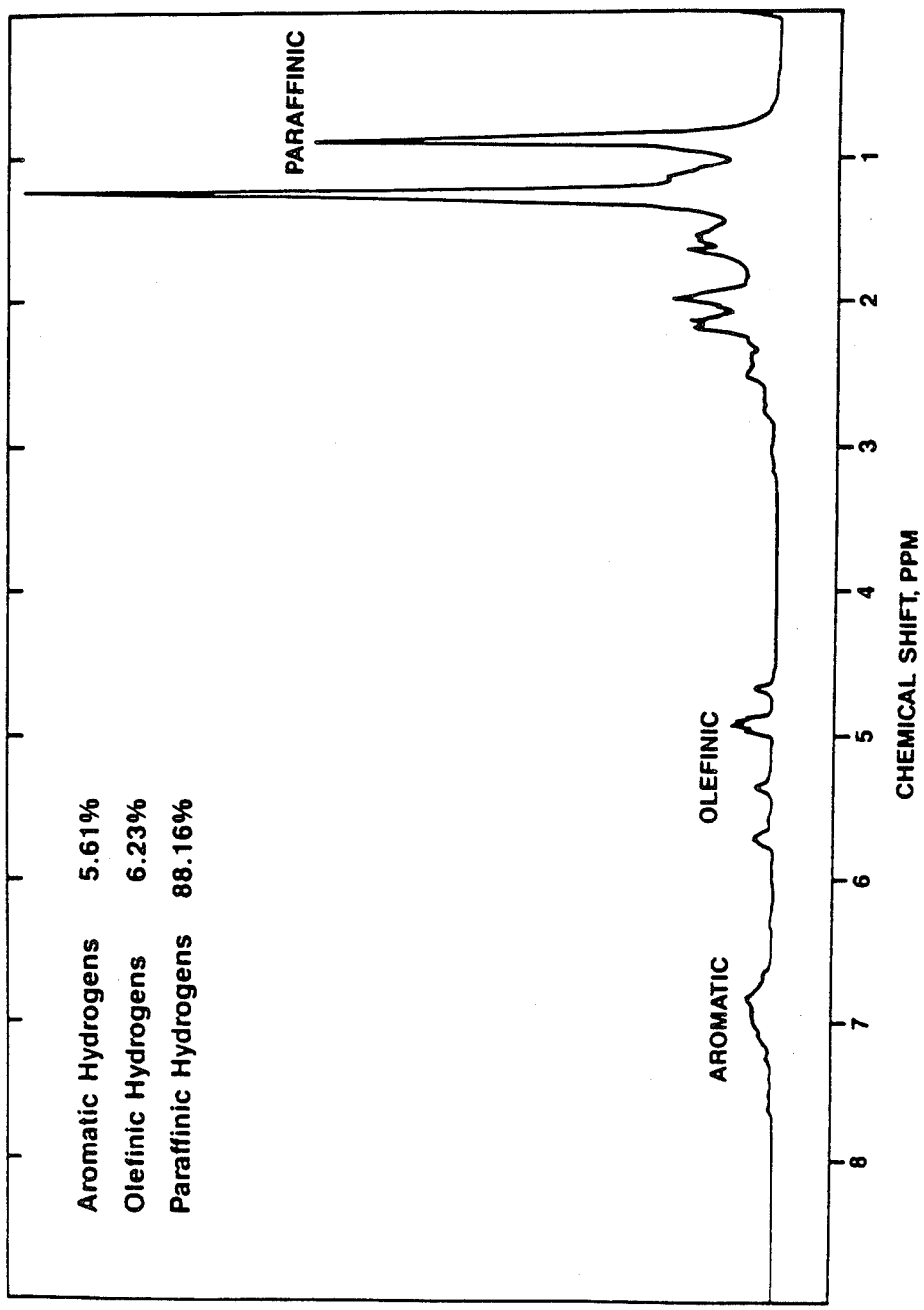
FIG. 5 shows the 500 MHz proton nuclear magnetic resonance spectrum of light Fluid-coker gas oil feed, with an indication of the olefinic, paraffinic and aromatic components.

The $C_9$ to $C_{16}$ gas oil and selected distillate fractions were also studied by proton NMR. The results are illustrated by the spectrum of FIG. 5 which shows the aromatic, olefinic and paraffinic hydrogens. A quantitative analysis of the spectrum showed that this gas oil is highly olefinic with a strong aliphatic character in that 88.2% of the hydrogens in the mixture are on saturated carbons, 6.2% on olefinically unsaturated carbons and only 5.6% on aromatic rings. Overall, the gas oil has a significantly higher percentage of linear olefins than does the coker naphtha as is shown by the following tabulation:

| Type | Vinylic Segment | Mole % Unsaturation | |
|---|---|---|---|
| | | Gas Oil $C_{10}$–$C_{15}$ | Naphtha* $C_4$–$C_{12}$ |
| I | —CH=CH$_2$ | 42 | 37 |
| II | —CH=CH— | 22 | 20 |
| III | —C=CH$_2$ | 16 | 17 |
| IV | —C=CH— | 7 | 12 |
| Conj. Diolefin | —C=C—C=C— | 14 | 14 |

*From Table IV.

Type I olefins represent about 42% of the total olefin content in the gas oil and about 37% in the naphtha. Most of the Type I olefins are 1-n-olefins which do not have branching anywhere on their hydrocarbon chain. The mass spectrometry data indicated that branching is mostly by methyl groups on the vinylic double bonds.

Selected distillate cuts of the light gas oil were also analyzed by NMR in a similar manner. The distribution of their vinylic hydrogens was particularly studied to determine the relative amounts of the various types of olefins present. The results are summarized in Table XI.

of different boiling points were found to be present. Thus the proportion of the Type I olefins changed from 4.5 to 33.8%.

The percentages of various types of olefinic hydrogens, are shown by Table XII. From the hydrogen distributions, the weight percentages of the various types of olefins were estimated. As it is shown by Table XII, the estimate of total olefins including dienes is between 50.4 and 61.7%. It is noted that the 61.7% value is for the $C_{16}$ fraction which was distilled with decomposition. As a result of cracking this fraction contained not only $C_{16}$ but lower molecular weight olefins as well. In case of the $C_{12}$ range, four narrow cut fractions were analyzed to determine changes in the proportion of different types of compounds. Only moderate changes were found in total olefin concentration (45.5 to 54.4%).

Figure 6:
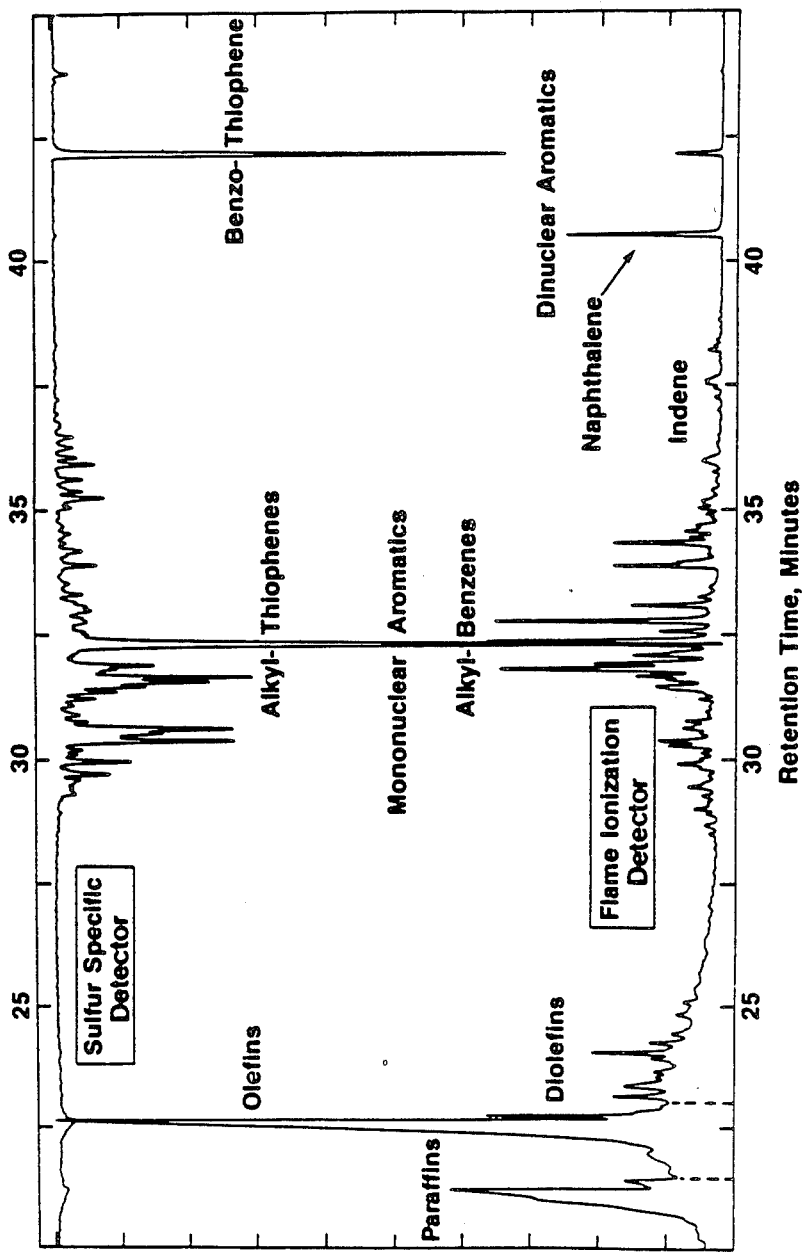
FIG. 6 shows the capillary gas chromatogram on a highly polar column of a $C_{12}$ fraction of light Fluid-coker gas oil, with separation of various types of aliphatic and aromatic components and sulfur compounds.

To illustrate the detailed composition of the present gas oil feeds, more detailed data are provided on a narrow $C_{12}$ fraction on the basis of GC/MS analyses. Such a cut cannot be separated on a nonpolar (boiling point) methylsilicone GC column. However, it was found that a highly polar type CP Sil 88 column (with a cyanopropylated silicone stationary phase) separated the various types of components according to their polarity. [This column is particularly suitable for the analysis of high boiling fractions since it has a high use temperature limit (about 275° C.)]. These components could then be largely identified via GC/MS studies. Two capillary GC traces with the groups of components identified are shown by FIG. 6.

The effluent of the above polar capillary column was split and led to a flame ionization and a sulfur specific detector. The chromatogram of the flame ionization detector shows the distribution of the organic compounds according to polarity in the lower part of the Figure. The upper chromatogram produced by the

TABLE XI

Relative Amounts of Various Types of Olefins in Light Fluid Coker Gas Oil Determined by 400 mHz Proton Magnetic Resonance Spectroscopy

| | Olefin Type in Gas Oil Fraction, % | | | | | | | | | | |
|---|---|---|---|---|---|---|---|---|---|---|---|
| Gas Oil Carbon Number | $C_9$–$C_{16}$ | $C_9$ | $C_{11}$ | $C_{12}$ | $C_{13}$ | $C_{14}$ | $C_{15}$ | $C_{16}$ | Narrow $C_{12}$ Cuts | | |
| Boiling Point, °F. Initial | 293 | 335 | 365 | 405 | 442 | 475 | 505 | 525 | 405 | 412 | 415 | 423 |
| Calcd. for 1 Atm. Final | 307 | 345 | 385 | 425 | 454 | 485 | 522 | 535 | 412 | 415 | 423 | 425 |
| Olefin I: —CH=2 | 42 | 37.1 | 43.6 | 40.0 | 38.5 | 43.5 | 44.0 | 37.9 | 43.4 | 45.5 | 42.5 | 33.8 |
| II: —CH=CH— | 22 | 16.4 | 16.8 | 22.0 | 17.3 | 21.2 | 21.6 | 16.2 | 19.6 | 17.5 | 20.3 | 23.4 |
| III: —C=CH$_2$ | 16 | 16.4 | 12.3 | 13.4 | 18.7 | 16.1 | 12.2 | 18.6 | 15.6 | 12.3 | 12.0 | 14.5 |
| IV: —C=CH— | 7 | 18.3 | 15.9 | 12.7 | 15.5 | 9.1 | 13.1 | 15.9 | 9.5 | 14.7 | 14.0 | 15.1 |
| Conjugated Diolefins | 14 | 11.8 | 11.3 | 11.9 | 10.1 | 10.1 | 9.1 | 11.3 | 11.9 | 9.9 | 11.2 | 13.2 |

The data of Table XI show that the relative olefin percentages of the distillate cuts vary. However, the percentage of the Type I olefins, including the desired 1-n-olefins, is generally more than a third of the total. The type I and II olefins combined, which includes all the linear olefins represent more than 55% of the total. The vinylically branched olefins are present in less than 35% amounts. The percentages of the conjugated diolefins are included in the table since they are converted to monoolefins during hydroformylation. However, the diene structures are uncertain and as such of approximate values.

Table XI also shows the distribution of olefin types in case of four narrow cut $C_{12}$ distillate fractions. As expected varying amounts of the different types of olefins sulfur specific detector shows the elution of the sulfur compounds in the order of their polarity.

The lower GC of FIG. 6 shows good separation of the aliphatic, monoaromatic and diaromatic hydrocarbon components of the $C_{12}$ fraction. With the help of GC/MS the aliphatic components could be broken down to paraffins, olefins plus diolefins. Their percentages were 18.6 and 50.5%, respectively. The monoaromatics included alkylbenzenes, naphthenobenzenes and trace amounts of alkylthiophenes. The total amount of monoaromatics was 28.2%. The main diaromatic compounds were indene, nephthalene and benzothiophene. Surprisingly, trace amounts of trimethyl phenols were also found.

The upper, sulfur specific GC of FIG. 6 shows that essentially all the sulfur compounds of the $C_{12}$ fraction were aromatic. The majority were alkyl thiophenes. Benzothiophene was also present in significant amounts.

A similar analysis of the $C_{14}$ fraction showed an even better separation of the components according to their polarity. In this case the distribution of the aliphatic components was similar but the major aromatic components were dinuclear: methylnaphthalenes and methylbenzothiophenes.

The distillate fractions of light gas oil were also analyzed for elemental composition, particularly for sulfur and nitrogen compounds and mercaptans. The data obtained are summarized in Table XIII.

The percentages of carbon and hydrogen were rather well maintained with increasing molecular weights. They indicate that the aliphatic character of the gas oil was fairly maintained. The total sulfur content remained at about 1% in the $C_9$ to $C_{12}$ range. Thereafter, there was a rapid increase of sulfur up to 2.82% in the $C_{16}$ fraction.

Experimental Procedures

Except as otherwise specified in the examples, the process found in those examples were carried out using the following experimental procedures.

Low and Medium Pressure Hydroformylation

The low and medium pressure hydroformylation experiments employed 300 ml and 150 ml steel autoclaves, respectively. Both autoclaves were equipped with impeller type stirrers operating at 1500 rpm. The total liquid feed was 100 g and 50 g respectively.

In a standard hydroformylation experiment, 80% of the feed was placed into the autoclave and deaerated with repeated pressurization with nitrogen. The solution, now at atmospheric nitrogen pressure, was then sealed and pressurized with 1:1 $H_2/CO$ to 50% of the reaction pressure.

The catalyst precursors, i.e., rhodium carbonyl acetylacetonate, dicobalt tetracarbonyl or dicobalt octacarbonyl plus the appropriate phosphorus ligand, were dissolved in 20% of the feed and placed into a pressure feed vessel connected to the initial $H_2/CO$ feed line and the autoclave.

The autoclave was then heated to the reaction temperature. Thereafter the catalyst solution, about 40 or 80 ml dependent on the volume of the autoclave, was pressured into the autoclave by the initial feed gas and the desired reaction pressure was established without stirring.

Thereafter, a switch was made to the feed gas pressure vessel of known volume which contained an appropriate mixture of $H_2/CO$ at higher initial pressure. Then the stirring of the reaction mixture started. This resulted in efficient contact of the gaseous $H_2/CO$ with the

TABLE XII

Hydrogen Distribution and Percentage of Various Types of Olefins Estimated in Light Fluid Coker Gas Oil by 400 MHz Proton Nuclear Magnetic Resonance Spectroscopy

| Distillate Fraction | | Hydrogen Distribution Found % | | | | | | Olefin Types Types Estimated, % | | | | | |
|---|---|---|---|---|---|---|---|---|---|---|---|---|---|
| Carbon Number | Boiling Range °C./mm | Olefin Types | | | | Conj. Diene | Paraffins | Aromatics | Olefin Types | | | | Conj. Dienes | Total Olefins |
| | | I | II | III | IV | | | | I | II | III | IV | | |
| 9 | 145–153/Atm | 3.76 | 1.10 | 1.10 | 0.62 | 1.21 | 86.45 | 5.77 | 19.9 | 8.8 | 8.8 | 9.8 | 6.3 | 53.5 |
| 11 | 185–196/Atm | 3.71 | 0.96 | 0.70 | 0.45 | 0.97 | 88.44 | 4.78 | 24.4 | 9.5 | 6.9 | 8.9 | 6.3 | 56.0 |
| 12 | 100–106/20 | 3.15 | 1.16 | 0.70 | 0.25 | 0.96 | 88.80 | 4.99 | 21.8 | 12.0 | 7.3 | 6.9 | 6.5 | 54.4 |
| 13 | 114/20–105/10 | 2.68 | 0.80 | 0.90 | 0.36 | 0.71 | 88.14 | 6.41 | 19.4 | 8.7 | 9.4 | 7.8 | 5.1 | 50.4 |
| 14 | 114–199/10 | 2.76 | 0.90 | 0.68 | 0.19 | 0.64 | 88.48 | 6.35 | 21.1 | 10.3 | 7.8 | 4.4 | 4.9 | 47.5 |
| 15 | 114–188/5 | 2.42 | 0.79 | 0.45 | 0.24 | 0.50 | 90.50 | 5.10 | 19.8 | 9.7 | 5.5 | 5.9 | 4.0 | 45.5 |
| 16 | –117/3 | 2.56 | 0.73 | 0.84 | 0.36 | 0.78 | 89.97 | 4.75 | 23.4 | 10.0 | 11.5 | 9.8 | 7.0 | 61.7 |
| 12 | 100/20 | 2.99 | 0.90 | 0.72 | 0.44 | 0.83 | 83.37 | 6.75 | 19.7 | 8.9 | 7.1 | 4.3 | 5.4 | 45.5 |
| 12 | 100–102/20 | 3.54 | 0.91 | 0.64 | 0.38 | 0.72 | 89.22 | 4.57 | 24.7 | 9.5 | 6.7 | 8.0 | 5.4 | 54.4 |
| 12 | 102–105/20 | 3.09 | 0.98 | 0.58 | 0.34 | 0.72 | 90.60 | 3.69 | 21.6 | 10.3 | 6.1 | 7.1 | 5.7 | 50.8 |
| 12 | 105–110/20 | 2.33 | 1.06 | 0.66 | 0.34 | 0.83 | 91.12 | 3.66 | 16.6 | 11.5 | 7.1 | 7.4 | 6.5 | 52.1 |

TABLE XIII

Elemental Composition of Light Fluid Coker Gas Oil

| Gas Oil Carbon Number | $C_9$ | $C_{10}$ | $C_{11}$ | $C_{12}$ | | | | | $C_{13}$ | $C_{14}$ | $C_{15}$ | $C_{16}$ |
|---|---|---|---|---|---|---|---|---|---|---|---|---|
| Boiling Point, °F. Initial | 293 | 335 | 365 | 405 | 405 | 412 | 415 | 423 | 442 | 475 | 505 | 525 |
| (Calcd. for 1 Atm) Final | 307 | 345 | 385 | 425 | 412 | 415 | 423 | 425 | 454 | 485 | 522 | 535 |
| Carbon, % | 86.10 | 85.62 | 85.77 | 86.17 | 85.71 | 85.11 | 85.48 | 86.14 | 85.74 | 85.65 | 84.51 | 84.77 |
| Hydrogen, % | 12.58 | 12.40 | 12.81 | 12.29 | 11.79 | 12.47 | 12.47 | 12.89 | 11.92 | 11.69 | 11.69 | 12.22 |
| Total Sulfur, % | 1.06 | 1.06 | 1.01 | 1.15 | 1.39 | 1.14 | 0.96 | 0.97 | 1.56 | 2.34 | 2.62 | 2.82 |
| Total Nitrogen, % | .0163 | .0244 | .0243 | 0.131 | .0294 | .0364 | .0352 | .0289 | .0395 | .0306 | .0652 | .0713 |
| Mercaptan Sulfur, % | .0084 | | .0105 | .0118 | .0132 | .0115 | .0116 | .0127 | .0061 | .0084 | .0825 | 0.1395 |
| Sulfur Compounds, %[a] | 4.17 | 4.63 | 4.86 | 5.53 | 6.69 | 5.49 | 4.62 | 4.68 | 7.50 | 12.28 | 14.90 | 17.27 |

[a] The weight percentages of sulfur compounds were calculated on the basis of total sulfur found assuming that the sulfur compounds were $C_3$ to $C_5$ alkylthiophenes in the $C_9$ to $C_{11}$ olefin range, benzothiophene in the $C_{12}$–$C_{13}$ range, $C_1$ to $C_{13}$ benzothiophenes in the $C_{14}$ to $C_{16}$ range It is noted that there was increasing decomposition during the distillation of these fractions. When the $C_{16}$ fraction was redistilled a broad molecular weight range of 1-n-olefins was found in the distillates. This suggests the breakdown of nonvolatile aliphatic sulfur compounds to generate olefins and mercaptans.

The total nitrogen contents of the distillates were more than an order less than that of the total sulfur. The mercaptan content is generally even lower. However, both the nitrogen and mercaptan contents rose sharply in the $C_{15}$ and $C_{16}$ fractions.

liquid reaction mixture. As the reaction proceeded the reactor pressure dropped due to the $H_2/CO$ reactant gas consumption. In response, feed gas was automatically provided as needed to maintain the pressure in the reactor. The feed gas had an appropriately high $H_2/CO$ ratio above one so as to provide $H_2$ not only for the main hydroformylation reaction but the hydrogenation side reactions as well.

The progress of the hyroformylation was followed on the basis of the CO and $H_2$ consumed. The latter was calculated on the basis of the pressure drop in the 1 liter $H_2/CO$ cylinder. Reactant conversion was estimated by plotting the CO consumption against the reaction time. In some cases, reaction rates were also estimated in spite of the complexity of the feeds and were expressed as the fraction of the theoretical $H_2/CO$ consumed per minute. Reaction rate constants were normalized for 1M transition metal concentration, assuming a first order rate dependence on the metal concentration.

When the reaction was discontinued, the $H_2/CO$ valve was shut and the autoclave immediately cooled with water. The synthesis gas in the head space of the autoclave was analyzed to determine the $H_2$ to CO ratio. After the release of excess $H_2/CO$, the residual liquid reaction mixture was also analyzed to determine conversion and selectivity. For these analyses a capillary gas chromatograph with a 50 m fused silica column was used.

Reactant conversions and product selectivities were also estimated on the basis of the gas chromatograms of the reaction mixture. The conversion of 1-n-olefins could be usually determined on the basis of the reduction of their peak intensities compared to those of the inert n-paraffins. These conversions could be correlated with the formation of the corresponding n-aldehyde and 2-methyl branched aldehyde products. When comparing hydrocarbon signal intensities with those of aldehydes and alcohols, a correction factor of 0.7 was assumed for the oxygenated compounds.

When the major products of the present hydroformulation process were alcohols, e.g. in cobalt-phosphine catalyzed reactions, samples of the reaction mixtures were silylated prior to GC analyses. An excess of N-methyl-N-trimethylsilyl-trifluoroacetamide was used to convert the alcohols to trimethylsilyl derivatives:

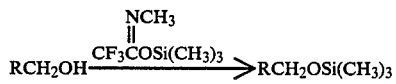

These derivatives of increased retention time are easier to chromatographically resolve and determine than their alcohol precursors.

High Pressure Hydroformylation

In the high pressure hydroformylation experiments, a 1 liter and a 1 gallon stirred autoclave were used. In these experiments, the amounts of synthesis gas consumed were not monitored. However, the liquid reaction mixture was sampled, usually after 10, 30, 120 and 180 minutes, and analyzed to determine olefin conversions and product selectivities.

In the one liter autoclave, the thermally cracked distillate was usually diluted with an equal amount of n-hexane, to provide a hydroformylation feed for standard experiments. However, about 20% of the diluent was employed to dissolve the catalyst, usually dicobalt octacarbonyl. In the one gallon autoclave, the cracked distillate was placed as such without solvent. The catalyst was usually dissolved in toluene solvent amounting to about 5% of the distillate reactant.

The high pressure experiments were carried out in a manner basically similar to those employed in the low pressure experiments. The distillate reactant was typically preheated to the reaction temperature with stirring under an initial $H_2/CO$ pressure equalling about $\frac{3}{4}$ of the final reaction pressure. The catalyst solution was then pressured into the stirred mixture using the initial $H_2/CO$ at reaction pressure and the pressure was maintained with additional, $H_2/CO$ feed gas as the reaction proceeded. During the periodical sampling of the liquid mixture, significant losses of $H_2/CO$ occurred, thus the $H_2/CO$ ratio thereafter was that of the feed gas rather than the initial gas. At the completion of the experiment the reaction mixture was rapidly cooled under $H_2/CO$ pressure and discharged when cold.

For a more detailed study of some of the products of high pressure cobalt hydroformylation, particularly those prepared in the one gallon reactor, the reaction mixtures were fractionally distilled. To avoid decomposition, the cobalt was removed as cobalt acetate by hot aqueous acetic acid plus air treatment. In a typical procedure, a 200% excess of acetic acid is used as an about 6% aqueous solution. As a reaction vessel a three necked glass vessel equipped with a mechanical stirrer, sintered glass bubbler, reflux condenser and a bottom valve for liquid takeoff, was used.

The stirred mixture of the cobalt hydroformylation reaction mixture and the theoretical amount of aqueous acetic acid was heated to reflux temperature while introducing air. Thereafter, stirring and aeration were continued for 20 minutes while refluxing. As indicated by the lightening of the color of the reaction mixture, cobalt conversion was usually substantially complete by the time refluxing started. The mixture was then allowed to cool and settle. Thereafter, the bottom pink aqueous phase was separated. The organic phase then was treated the same way again. After the second acid wash, two washes with distilled water followed. Lack of color of the aqueous washings indicated a complete prior removal of cobalt.

The cobalt free organic phase was fractionally distilled in vacuo using a 1 to 2 ft long, glass beads packed column. The composition of distillate fractions was monitored by capillary GC to help appropriate fractionation. Selected fractions were also analyzed by a combined gas chromatography/mass spectrometry (GC/MS).

Aldehyde Hydrogenation To Produce Alcohols

Typically, 1 liter aldehyde product or heptane solution thereof was hydrogenated in the presence of 60 ml water which was routinely added to facilitate the hydrolysis of any diacetals formed via aldehyde alcohol condensation. About 200 ml of a Co/Mo based catalyst was used.

The hydrogenations were carried out in a 1 gallon rocking autoclave at 232° C. (450° F.) under 3000 psi (204 atm) pressure for 24 hrs. The resulting crude alcohol was characterized by GC/MS and purified by fractional distillation.

Low Pressure Hydroformylation of $C_4$–$C_{12}$ Naphtha Fractions in the Presence of Phosphine-Rhodium Complexes (Examples 1–12)

The previously described $C_4$–$C_{12}$ Fluid coker naphtha and its distillate fractions were hydroformylated without prior treating in the presence of rhodium complexes of various phosphines under varying low pressure conditions.

The rhodium catalyst systems employed and the reaction conditions used are summarized together with some results for orientation in Table XIV. In general, in the presence of sufficient amounts of phosphine-rhodium catalyst complexes, rapid and selective hydroformylation occurs at low pressure. Very little hydrogenation occurs. GC analysis provides a quantitative measure of the two major aldehyde products and a more qualitative estimate of the total aldehyde products. At low pressure, the total aldehyde products could be more reliably estimated, on the basis of the $H_2/CO$ consumed, by comparing the found values with the amounts calculated for converting the 1-n-olefin component. Based on the initial rates of $H_2/CO$ consumption (0–1 minute) the hydroformylation rates of the most reactive 1-n-olefin components were also compared in the presence of different catalyst complexes.

Comparative 1-n-decene hydroformylation experiments with the $C_{10}$ naphtha fraction as a feed showed that the activity and selectivity of rhodium complex catalysts could be controlled by the chemical structure and excess concentration of the phosphine ligand added, as it will be discussed in the individual examples.

$H_2/CO$ ratio during the run indicated that very little hydrogenation side reaction occurred.

The final reaction mixture was analyzed by GC. The chromatogram showed no 1-n-olefin components, indicating their complete conversion. The main products were the n-aldehydes. Among the minor aldehyde products, those of the 2-methyl substituted aldehydes were readily recognizable. Table XV shows the signal intensities of these two types of aldehyde products and those of the n-paraffin components. The paraffin components represent multiple internal standards which were present in the starting reactants in amounts comparable to the 1-n-olefin reactants of corresponding carbon numbers. The data of the table qualitatively show that the

TABLE XV

Major Aldehyde Products and n-Paraffin Components of Fluid Coker Naphtha

| Alkyl Carbon No. | GC Signal Intensity, % | | |
|---|---|---|---|
| | Normal Aldehyde | 2-Methyl Aldehyde | Normal Paraffin |
| 5 | 1.104 | 0.926 | 0.798 |
| 6 | 1.837 | | 1.468 |
| 7 | 1.796 | | 2.927 |
| 8 | 2.259 | 1.586 | 3.064 |
| 9 | 2.047 | 1.350 | 2.208 |
| 10 | 2.182 | 1.115 | 2.043 |
| 11 | 1.423 | 0.715 | 1.409 |
| 12 | 0.514 | 0.239 | 0.393 |
| 5–12 | 13.162 | | 14.310 | conversion of the 1-n-olefins resulted in the formation of the expected normal aldehyde and 2-methyl branched aldehyde products:

TABLE XIV

Hydroformylation of Fluid Coker Naphtha with Phosphine-Rhodium Complex Catalysts

| Feed Carbon No. | Rh Conc. mM | Phosphine Ligand | | Reaction Conditions | | | | GC Analyses | | 1-n-Olefin Based | |
|---|---|---|---|---|---|---|---|---|---|---|---|
| | | Conc. M | Structure | Temp. °C. | Press. psi | Time Min | $H_2/CO$ Final | Two Major Products | | $H_2/CO$ Consumed % | Rate $K_N$ 1 min. |
| | | | | | | | | n/i | Yield, %[a] | Total Products Yield, %[a] | |
| 4–12 | 10 | 0.14 | $(C_4H_9)_3P$ | 180 | 1000 | 40 | 1.95 | ~2 | | 238 | 1042 |
| 10 | 2 | 0.14 | $(C_8H_{17})_3P$ | 180 | 1000 | 60 | 1.08 | 1.88 | 118 | 177 | 238 | 1042 |
| 10 | 2 | 0.14 | $(C_8H_{17})_3P$ | 180 | 350 | 60 | 1.05 | 2.0 | 119 | 187 | 224 | 554 |
| 10 | 1 | 0.14 | $(i\text{-}C_8H_9)_3P$ | 180 | 100 | 60 | 1.05 | 1.64 | 94 | 128 | 210 | 630 |
| 7 | 2 | 0.14 | $(C_4H_9)_3P$ | 180 | 1000 | 12 | ~1 | 2.3 | 115[b] | 133[b] | 71 | 360[b] |
| 7 | 10 | 0.14 | $(C_4H_9)_3P$ | 180 | 1000 | 1 | 1.47 | 2.15 | 118 | 165 | 161 | 720 |
| 7 | 1 | 0.14 | $(C_4H_9)_3P$ | 180 | 1000 | 20 | ~1 | 2.3[b] | — | — | 27[c] | — |
| 10 | 4 | 1.0 | $(C_4H_9)_3P$ | 180 | 1000 | 60 | 0.95 | 2.02 | 102 | 130 | 238 | 210 |
| 10 | 2 | 0 | — | 180 | 1000 | 120 | 1.0 | 1.93 | 77 | | 95 | 7 |
| 10 | 2 | 1.0 | $(C_4H_9)_3P$ | 180 | 350 | 60 | 5.1 | 3.20 | 101 | 147 | 210 | 88 |
| 10 | 2 | 1.0 | $Ph_2PC_{18}H_{37}$ | 145 | 350 | 60 | 5.75 | 6.76 | 106 | 164 | 214 | 308 |
| 10 | 2 | 0.14 | $(i\text{-}C_4H_9)_3P$ | 180 | 1000 | 60 | 1.05 | 1.25 | 90 | 161[d] | 309 | 3610 |

[a]Expressed in percent compared to the amount theoretically required for the conversion of the 1-n-olefin component.
[b]According to G.C. only 42% of the 1-n-heptene reacted before inhibition occurred.
[c]According to G.C. only 15% of the 1-n-heptene reacted. $H_2/CO$ uptake ceased in 1 minute.
[d]The total yield of aldehydes plus alcohols was 165%, according to G.C.

EXAMPLE 1

Hydroformylation of a $C_4$–$C_{12}$ Naphtha with a Tributyl Phosphine Rhodium Complex The broad naphtha cut previously described was hydroformylated in the presence of a catalyst system containing 10 mM rodium, employed as dicarbonyl acetylacetonate, and 0.14M tri-n-butyl phosphine. The reaction was run at 180° C. under 1000 psi (6900 kPa) pressure for 40 minutes. The initial $H_2/CO$ ratio was 1, the $H_2/CO$ feed ratio employed during the run 1.22 and the final head space ratio 1.95. The increase of the $$C_nH_{2n+1}CH{=}CH_2 \xrightarrow{CO/H_2} C_nH_{2n+1}CH_2CH_2CHO +$$

$$C_nH_{2n+1}\underset{\underset{CH_3}{|}}{CH}CHO$$

The n/i ratio of these linear versus branched aldehydes is about 2. Using the present catalyst system and conditions, this ratio is in the range of n/i values obtained on the hydroformylation of pure 1-n-olefins and Type I olefins, in general. As the 1-n-olefins were converted, the reaction rate decreased and the reaction was discontinued. Thus the results of this example indicate that the 1-n-olefin components of the distillate feed can be selectively hydroformylated in the presence of phosphine rhodium complex based catalysts.

EXAMPLE 2

Hydroformylation of $C_{10}$ Naphtha With a Tri-n-octyl Phosphine Rhodium Complex at 1000 psi The previously described $C_{10}$ fraction of the Fluid coker-naphtha was hydroformylated at 180° C. under 1000 psi, using the low pressure procedure. The catalyst system was derived from 2 mM rhodium dicarbonyl acetylacetonate and 0.14M tri-n-octyl phosphine. The reaction period was 60 minutes. The ratio of the initial $H_2/CO$ was 1; the $H_2/CO$ feed was of 51 to 49 ratio. The final $H_2/CO$ ratio of the head space was 52 to 48, indicating a virtual absence of hydrogenation.

The reaction was very fast during the initial period of about 5 minutes, then the reaction became slower and slower. Apparently, the 1-n-decene component of the feed was rapidly hydroformylated while the isomeric Type II and Type III decenes were more sluggish to react.

A GC analysis of the final reaction mixture showed that 1-n-decene was absent. Apparently, it reacted to form n-undecanal and 2-methyl decanal. The latter compounds constituted about 69% of the total aldehydes formed. The ratio of the normal to the iso aldehyde produced was 1.88.

On the basis of the original concentration of 1-n-decene in the feed, the theoretical amount of $C_{11}$ aldehydes was calculated. The total aldehydes were 171% of the amount which could have been derived from 1-n-decene. Apparently major amounts of the Type II decene components of the feed were also hydroformylated. On the other hand, the GC showed that 2-methylnonene was still substantially unconverted in the reaction mixture. This indicated that the Type III olefins of the feed are of low reactivity in the presence of this catalyst system.

EXAMPLE 3

Hydroformylation of $C_{10}$ Naphtha With a Tri-n-octyl Phosphine Rhodium Complex at 350 psi The experiment of Example 2 was repeated at 350 psi instead of 1000 psi pressure. Qualitatively, the reaction was very similar. The reaction rate was only slightly lower. The final $H_2/CO$ ratio in the head space was 51/49.

The ratio of the two major products, n-undecanal versus 2-methyldecanal was about 2. These two aldehydes represent 119% of the calculated yield based on the starting 1-n-decene. The total aldehyde yield is 187% of the 1-decene based value. Thus, the amount of the above two aldehydes is about 62% of the total.

EXAMPLE 4

Hydroformylation of $C_{10}$ Naphtha With a Tri-i-octyl Phosphine Rhodium Complex Example 2 was repeated using the rhodium complex of tri-i-octyl phosphine [tris-(2,4,4-trimethyl-pentyl)-phosphine] as the catalyst instead of that of tri-n-octyl phosphine. The reaction was very similar to that of Example 2 except for the lower n/i ratio of the two main products. The ratio of n-undecanal to 2-methyl decanal was 1.64 in the present experiments while a ratio of 1.88 was found in Example 2. The reduced n/i ratio was apparently a result of the steric crowding effect of the bulky tri-i-octyl phosphine ligand.

The two main aldehyde products represent 94% of the theoretical yield based on the 1-n-decene contact of the feed. On the same basis, the yield of the total aldehydes was found to be 128%. Thus, the two main aldehydes amounted to about 74% of the total aldehydes produced.

EXAMPLES 5-7

Hydroformylation of $C_7$ Naphtha With Tri-n-butyl Phosphine Rhodium Complex

The previously described $C_7$ fraction of the Fluid coker naphtha was hydroformylated at 180° C. under 1000 psi pressure with the standard low pressure procedure using 1/1 $H_2/CO$ as reactant. Three hydroformylation experiments were carried out using different concentrations of rhodium in the presence of excess tri-n-butyl phosphine, at 0.1M concentration. The rhodium was provided as a dicarbonyl acetylacetonate derivative in 1,2 and 10 mM concentration. Reasonably fast reaction occurred with 2 mM rhodium. The results of this experiment (Example 5) will be discussed at first.

Gas consumption data indicate that initially the reaction rate was very high but started to drop in 2 minutes. When the reaction was discontinued after 12 minutes, gas absorption was minimal. The $H_2/CO$ ratio remained close to 1 during the reaction.

Gas chromatography showed that 42% of the 1-n-heptene component of the feed was reacted. The -n-heptene derived component of the product was mostly n-octanal and 2-methylheptanal. The n/i ratio of these products was 2.3. The amount of the two compounds was 115% of the calculated value based on the converted n-1-heptene. The total aldehyde products correspond to 133% of that value. Apparently, minor amounts of other heptene isomers besides 1-n-heptene were also reacted.

In another experiment (Example 6) the same reaction was run in the presence of 10 mM rhodium. This resulted in an extremely fast reaction. About 0.645 moles of $H_2/CO$ mixture was consumed within the one minute reaction time. The run gas used had a 52/48 ratio. The final ratio of $H_2/CO$ was 1.47, a substatial increase over the initial $H_2/CO$ ratio of 1. Apparently, no significant hydrogenation occurred.

The gas chromatogram of the reaction mixture showed that all the 1-n-heptene was converted. The two main products were again n-octanal and 1-methyl heptanal, in a ratio of 2.15. The sum of these two corresponds to 18% more than the amount which could have been theoretically derived from 1-heptene. The total amount of aldehyde product is 165% of the amount derivable from 1-heptene. Thus, the n-octanal formed equals to 48% of the total aldehydes formed.

In a thid experiment (Example 7) only 1 mM rhodium was employed. At this low catalyst concentration, little reaction occurred. In 20 minutes only 15% of the 1-n-heptene was consumed. The n/i ratio of the two main products was 2.3.

EXAMPLE 8

Hydroformylation of $C_{10}$ Naphtha with Rhodium Complex in the Presence of 1M Tributyl Phosphine The $C_{10}$ fraction of the coker naphtha was hydroformylated under the conditions of Example 2. However, 1M tri-n-butyl phosphine was used instead of 0.14M tri-n-octyl phosphine to ascertain the effect of an increased excess of phosphine ligand. Also, 4 mM instead of 2 mM rhodium was used to counteract the inhibitory effect of the added ligand.

The intial reaction was very fast. All the 1-n-decene was converted in about 140 seconds. Thereafter, the internal decenes were being converted at a much slower rate. At 60 minutes, the $CO/H_2$ consumption rate was quite low. The reaction was discontinued after 60 minutes.

A GC analysis of the reaction mixture showed that the two main reaction products, n-undecanal and 2-methylnonanal were formed at an increased ratio. Due to the increased excess trialkyl phosphine ligand concentration, the n/i value was significantly higher, 2.02. (In the presence of the smaller ligand concentration Example 3, the n/i ratio was 1.88). The amount of the two major products was 102% of the value calculated for the amounts derivable for 1-n-decene. The total amount of aldehyde products formed was 130% of the theoretical value calculated for 1-n-decene.

EXAMPLE 9

Hydroformylation of $C_{10}$ Naphtha With Rhodium Dicarbonyl Acetylacetonate

The same $C_{10}$ naphtha was also hydroformylated under the conditions of the previous example, but without any phosphine catalyst modifier. In this example, the usual rhodium catalyst precursor, rhodium dicarbonyl acetylacetonate was used alone in amounts corresponding to 2 mM rhodium concentration.

Apparently due to the absence of phosphine modifying ligand, the reaction was slow. Although the reaction time was increased to 120 minutes, even the conversion of the most reactive olefin component of the feed, 1-n-decene, remained incomplete. Also, the amount of the $CO/H_2$ reactant gas consumed was only about half of that of the previous example. (The 1/1 ratio of $H_2/CO$ was well maintained during reaction). The main products of the reaction were again un-decanal and 2-methyldecanal derived from 1-n-decene. They represented about 77% of the aldehyde products. No alcohol product was observed. The n/i ratio of the two main products was 1.93.

EXAMPLE 10

Hydroformylation of $C_{10}$ Naphtha with Tri-n-butyl Phosphine Rhodium Complex at 350 psi 5/1 $H_2/CO$ Pressure The $C_{10}$ naphtha was hydroformylated under the conditions of Example 8 but at reduced pressure, at 350 psi of 5/1 $H_2/CO$. The amount of rhodium was cut to 2 mM. The tri-n-butyl phosphine concentration was the same, 1M. The 5/1 $H_2/CO$ ratio was maintained by a feed gas ratio of 53/47.

The sharply reduced CO partial pressure of this reaction significantly increased the n/i ratio of the two major aldehyde products without a major drop in the reaction rate.

Compared to Example 8, the n/i ratio of the two main products increased from 2.02 to 3.2. These two products represented 68.5% of the total aldehyde yield. No alcohols were formed during the 60 minutes reaction time. The yield based on 1-decene was 101% for the two main aldehydes. The total aldehydes amounted to 147% of the 1-decene based calculated yield, indicating a significant conversion of some of the other olefin components of the feed. The amount of $H_2/CO$ needed to hydroformylate all the 1-decene was consumed during the first 7 minutes of the experiment.

EXAMPLE 11

Hydroformylation of $C_{10}$ Naphtha With a Rhodium Complex of n-Octadecyl Diphenyl Phosphine at 145° C.

The $C_{10}$ naphtha fraction was hydroformylated with the rhodium complex of an alkyl diaryl phosphine to produce a higher ratio of normal versus iso aldehyde products. To derive the catalyst system, 2 mM rhodium and 1M n-octadecyl diphenyl phosphine were used. The reaction was run at 145° C. under 350 psi 5/1 $H_2/CO$ pressure. During the reaction a 53/47 mixture of $H_2/CO$ was fed. This feed gas more than maintained the initial $H_2/CO$ ratio during the 60 minutes run. The final $H_2/CO$ ratio was 5.75, indicating the absence of major hydrogenation side reaction. Compared to the previous example the difference is in the type of phosphine ligand used and the reaction temperature.

The use of the akyl diaryl phosphine ligand resulted in a much increased selectivity of 1-n-decene hydroformylation to n-undecanal. The n/i ratio of the two main aldehyde products was 6.76. Also, in the presence of this ligand a faster hydroformylation rate was observed. An amount of $H_2/CO$ sufficient to convert all the 1-n-decene was consumed within 3 minutes.

After the 60 minutes reaction time, GC analyses indicated that the amount of the two main aldehyde products was 106% of the calculated yield for 1-n-decene. The total aldehyde product were 164% of this yield and no alcohols were formed.

EXAMPLE 12

Hydroformylation of $C_{10}$ Naphtha with a Rhodium Complex of Tri-i-butyl Phosphine The $C_7$ naphtha fraction was hydroformylated under conditions similar to those in Examples 2, 21 and 22, i.e., at 180° C. under 1000 psi 1/1 $H_2/CO$ pressure. However instead of a tri-n-alkyl phosphine, a sterically crowded tri-i-alkyl phosphine, tri-2-methylpropyl phosphine (tri-i-butyl phosphine) was used. The phosphorus ligand concentration was 0.14M, the rhodium concentration 2 mM. Feeding a 51/49 mixture of $H_2/CO$ as usual maintained the equimolar synthesis gas reactant mixture during the 60 minutes reaction time.

The use of the tri-i-butyl phosphine ligand resulted in a fast reaction of low n/i selectivity. Enough $H_2/CO$ reactant was consumed during the first minute of the reaction to convert all the 1-n-decene in the reaction mixture. The n/i ratio of the two main aldehyde products was 1.25. After the complete run, GC showed that the combined yield of the two main products formed was 90% of the value calculated for 1-n-decene. The total aldehyde yield corresponded to 161% of this value. In this reaction minor amounts of alcohols were also formed. Thus, the combined yield of aldehydes and alcohols was 165% of the theoretical yield of the hydroformylation of the 1-n-decene component.

Medium Pressure Hydroformylation of $C_4$-$C_{12}$ Naphtha Fractions in the Presence of Phosphine-Cobalt Complexes (Examples 13–16)

The previously described, untreated $C_4$-$C_{12}$ Fluid coker naphtha and its distillate fractions were also hydroformylated in the presence of cobalt complexes of trialkyl phosphine complexes. The reaction conditions used and results obtained are summarized in Table XVI.

In general, the substitution of cobalt for rhodium in these phosphine complex catalyst system changes the activity and the selectivity of the system. The inherent activity of the cobalt systems is about 2 orders of magnitude smaller. In contrast to rhodium, the cobalt complexes are multifunctional catalysts. Olefin isomerization is extensive; this results in an increase of the n/i ratio of the products. Aldehyde to alcohol hydrogenation is also extensive. Since the major products are alcohols and the reactions are performed at medium rather than low pressure, syn gas consumption based olefin conversions are relative rather than absolute values.

EXAMPLE 13

Hydroformylation of a $C_4$–$C_{12}$ Naphtha With a Tributyl Phosphine Cobalt Complex About 93.8 g of the broad cut naphtha feed previously described was hydroformylated in the presence of a catalyst system containing 80 mM of cobalt, added as dicobalt octacarbonyl, and 0.24M tri-n-butyl phosphine (P/Co=3). The reaction was run under the conditions of the first example (180° C., 1000 psi) but for a longer period (60 min). While the initial $H_2/CO$ ratio was again 1/1, the synthesis gas added during the run had a significantly higher $H_2/CO$ ratio of 3/2. This higher run gas ratio was employed because cobalt phosphine complexes catalyze both olefin hydroformylation to aldehydes and aldehyde reduction to alcohols.

During the reaction about 1 mole of $H_2/CO$ mixture was consumed. In contrast to the first example, no significant reduction in the reaction rate was observed. The final head space ratio of $H_2/CO$ dropped to 0.68, indicating that hydrogenation took place to a major degree.

cobalt and 120 mM phosphine ligand (P/Co=6). The reaction was carried out at 180° C. under 1500 psi for 2 hours. The initial $H_2/CO$ ratio was 1. During the run an $H_2/CO$ ratio of 60/40 was used. The final $H_2/CO$ ratio of the head space was 48/50. There was no apparent decrease of hydroformylation rate during the reaction. The maximum rate was reached after about 10 minutes. In 120 minutes, the $H_2/CO$ feed consumed was about 155% of the amount theoretically required to convert the 1-n-decene component to undecyl alcohol.

The gas chromatogram of the final reaction mixture shows no significant amounts of 1-n-decene present. However, other decene isomers appear to be present in increased amounts as a consequence of concurrent isomerization-hydroformylation.

The hydroformylation produced the expected two significant aldehyde products derived from 1-n-decene. However, these were largely hydrogenated to the corresponding alcohols, as shown by the reaction scheme:

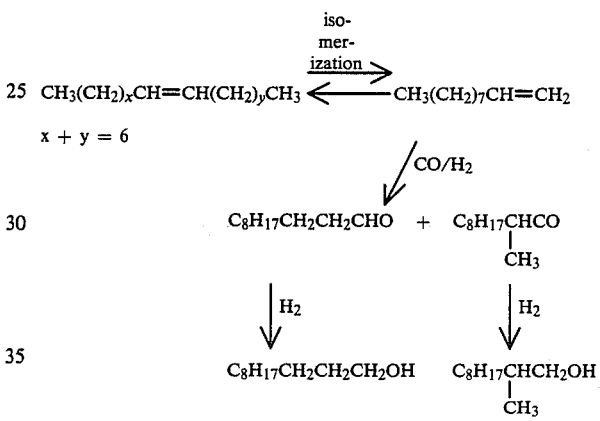

TABLE XVI

Hydroformylation of Fluid Coker Naphtha with Phosphine Cobalt Complex Catalysts
The reactions were carried out at 180° C. using an initial $H_2/CO$ feed ratio of 1 and a run gas ratio of 3/2, in the presence of sufficient tri-n-butyl phosphine to provide an P/Co ratio of 3

| Example No. | Feed Carbon No. | Co Conc. nM | Reaction Conditions | | 1-n-Olefin Based Rate Data | | | Total Product Yield %[c] | 4 Major Products Yield % C | Normal Products in Total % | Alcohol Products in Total % | n/i Ratio 4 Major Products |
|---|---|---|---|---|---|---|---|---|---|---|---|---|
| | | | Press. psi | Time min. | $H_2/CO$ Consumed % (Total)[a] | Normalized Rate $K_N$ (Period) | Period[b] Measured Min. | | | | | |
| 13 | 4–12 | 80 | 1000 | 60 | | | | | | | | |
| 14 | 10 | 40[e] | 1500 | 120 | 155 | 4 | 10–20 | 139 | 73.5 | 52.1 | 92.1 | 7.62 |
| 15 | 7 | 40 | 1000 | 60 | 70 | 0.8 | 10–20 | 38.8 | 28.6 | 56.0 | 58.3 | 10.06 |
| 16 | 10 | 40 | 1500 | 120 | 160 | 1 | 15–20 | 63.2 | 35.7 | 49.5 | 91.2 | 7.00 |
| 17 | 10 | 120 | 1500 | 60 | 191 | 1.6 | 5–6 | 129 | 64.8 | 44.8 | 92.8 | 8.45 |

[a]Expressed in percent theoretically required for the conversion of the 1-n-olefin component to the corresponding alcohol.
[b]The hydroformylation rate increases with time.
[c]Expressed as percent of the theoretical amount of the product of the hydroformylation of the 1-n-olefin component of the feed.
[d]The four major products are two aldehydes and the two alcohols which can be derived from the 1-n-olefin component feed.
[e]Instead of tri-n-butyl phosphine, tri-n-octyl phosphine was used as a ligand.

The final reaction mixture was again analyzed by GC. The chromatogram obtained showed an essentially complete conversion of the 1-n-olefin components and the formation of major amounts of the corresponding n-aldehydes and alcohols.

EXAMPLE 14

Hydroformylation of $C_{10}$ Naphtha With a Tri-n-octyl Phosphine Cobalt Complex at 1500 psi The $C_{10}$ fraction of the Fluid-coker naphtha used in the previous examples was also hydroformylated using a catalyst system based on dicobalt octacarbonyl and tri-n-octyl phosphine. The concentrations were 40 mM The amount of the above 4 products is about 75.5% of the calculated yield for 1-decene.

The total yield of aldehydes plus alcohols was also estimated on the basis of the capillary GC analysis of the final reaction mixture. It was 139% of the products calculated for a complete conversion of the 1-n-decene component. The n-aldehyde plus n-alcohol amounted to 52.1% of the total products. Most of the products, 92.1% were alcohols. Only about 7.9% were aldehydes. The n/i ratio of the 4 major products, mostly derived from 1-n-decene was high, 7.62.

EXAMPLE 15

Hydroformylation of $C_7$ Naphtha With a Tributyl Phosphine Cobalt Complex

The $C_7$ fraction of the Fluid coker naphtha employed in Examples 5, 6 and 7 was also hydroformylated with a catalyst system derived from dicobalt octacarbonyl and trioctyl phosphine. Forty mM cobalt and 0.12 mM ligand were used (P/CO=3). The reaction conditions were similar to those in Example 6: 180° C., 1500 psi for 1 hour using a 60/40 ratio of run gas. The initial and final ratio of $H_2$/CO in the reactor were both very close to 1. The $H_2$/CO feed consumed was about 70% of the amount calculated for the conversion of the 1-n-heptene component to octanols.

According to GC there was no unconverted 1-n-heptene left in the reaction mixture. Besides hydroformylation isomerization occured. The major hydroformylation products present were n-octanal, 2-methylheptanal and the corresponding alcohol hydrogenation products. The overall n/i ratio of these products is about 10.06. These four products represent about 56% of the total aldehyde and alcohol products. About 58.3% of the total products were alcohols. The significant percentage, 41.7%, of the aldehydes present indicated that the reaction was incomplete.

EXAMPLES 16 AND 17

Hydroformylation of $C_{10}$ Naphtha With a Tri-n-butyl Phosphine Cobalt Complex The $C_{10}$ fraction of the coker naphtha was hydroformylated in the presence of two dicobalt octacarbonyl plus tris-n-butyl phosphine catalyst systems having a P/Co ratio of 3. The reactions were run at 180° C. under 1500 psi 1/1 $H_2$/CO pressure. The high $H_2$/CO ratio was maintained by the addition of a 60/40 feed gas mixture during the reaction.

The rate of absorption of the $H_2$/CO reactant gas showed that the reaction has an initial inhibition period, dependent on the concentration of catalyst. At 40 mM cobalt, this inhibition period is about 5 minutes; at 120 mM Co, it is less than 1 min. At 40 mM cobalt (Example 16), it takes about 35 minutes to consume enough $H_2$/CO for a complete conversion of the 1-n-decene component of the naphtha cut. At 120 mM cobalt (Example 17), only about 10 minutes are required to achieve this conversion. The rate of absorption indicate a first order reaction rate dependence on cobalt concentration.

The first reaction with 40 mM cobalt (Example 16) was run for a total of 120 minutes. In that time 0.254 moles of $H_2$/CO was consumed. This is about two and a half fold of the amount necessary to convert the 1-decene component to the corresponding aldehydes. However, most of the primary aldehyde products were reduced to the corresponding alcohols. The two main aldehyde products and the corresponding alcohols are derived from 1-decene via combined isomerization hydroformylation as described in Example 14. Capillary GC indicated that the yield of the total oxygenated products 63.2% of the value calculated for a complete conversion of the 1-decene component. About half of the products were of straight chain. Most of the products, 91.2% were alcohols rather than aldehydes. The n/i ratio of the four major products was 7.

The second reaction with 120 mM cobalt (Example 17) was run for a total of 60 minutes and consumed 0.292 moles of $H_2$/CO. This is almost 3 fold of the amount needed to convert 1-decene to aldehydes. Again most of the aldehydes formed were reduced to alcohols. Capillary GC indicated that the increased catalyst concentration resulted in approximately doubling the total product yield to 129% of the calculated value for the 1-n-decene feed component. The yield of the four major products which could be derived from 1-n-decene was 64.8%. The n/i ratio of these products was 8.45. About 44.8% of the total products was completely linear.

EXAMPLES 18 AND 19

Hydroformylation of 2-Butene with a Tr-n-Butyl Phosphine Cobalt Complex and Added Thiol Comparative hydroformylation experiments were carried out with 2-butene as a model olefin reactant under the conditions of Example 13 to demonstrate that thiol inhibition can be overcome by the use of cobalt phosphine complex catalysts in the present process.

Two reactions were carried out, each starting with 100 g reaction mixture containing 20 g (0.1 mole) 2-butene, 2.43 g (12 milimole) tri-n-butylphosphine and 0.68 g (2 milimole) dicobalt octacarbonyl in 2-ethylhexyl acetate as a solvent. One of the reaction mixtures also contained 38.8 mg (0.626 milimole) ethyl mercaptan to provide 200 ppm mercaptan sulfur. Both reactant solutions were reacted with 1/1 $H_2$/CO under 1000 psi pressure at 180° C. An equimolar ratio of $H_2$/CO was maintained during the run by supplying additional $H_2$/CO in a 3/2 ratio during the reaction.

Both reaction mixtures were hydroformylated with similar selectivity. The only significant difference was in the reaction rates. The 2-butene was more reactive in the absence of ethanethiol. In the absence of the thiol, 50% olefin conversion was achieved within 18 minutes. In the presence of the thiol a similar conversion took 36 minutes.

After the reaction, both mixtures were analyzed. The most significant difference between the mixtures was the selectivity to 1-butene; 10.5% in the absence of thiol versus 5.8% in its presence. This indicated inhibition by the thiol of the isomerization of 2-butene to produce the more reactive 1-butene which is then hydroformylated to produce n-valeraldehyde with high selectivity. The latter is largely converted by hydrogenation to n-amyl alcohol.

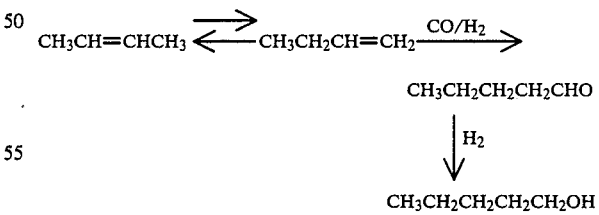

The selectivities toward the various oxygenated products were similar in the absence and presence of thiol: overall n/i 8.15 vs. 8.92; alcohol/aldehyde 0.52 vs. 0.57; aldehyde n/i 6.81 vs. 7.34; alcohol n/i 12.6 vs. 13.8.

High Pressure Hydroformylation of $C_4$–$C_{12}$ Naphtha Fractions in the Presence of Cobalt Complexes (Examples 20–30)

The previously described $C_4$–$C_{12}$ Fluid coker naphtha containing 1-n-olefins as the major type of olefin reactant was also hydroformylated successfully in the presence of cobalt complexes without phosphine modifiers at high pressure. $C_{10}$ and $C_8$ feeds were studied in detail. The reaction conditions used and some of the results obtained are summarized in Table XVII.

In general, the omission of the trialkyl phosphine modifying ligand from these cobalt carbonyl complex catalysts resulted in greater hydroformylation activity. However, the ratio of n-aldehydes to the 2-methyl branched aldehydes was drastically reduced to values between about 1.9 and 3.2. The cobalt catalysts could be used not only at high but at low temperature as well. In the low temperature region of 110° to 145° C., the process was selective for the production of these major aldehyde isomers. The rate of olefin isomerization was drastically reduced. The n/i ratio of the products and the amount of aldehyde dimer and trimer products were inversely proportional with the reaction temperature.

GC retention times of components are approximately proportional to their boiling points, this indicates that the overlapping components cannot be separated by fractional distillation.

EXAMPLES 21 AND 22

Hydroformylation of $C_{10}$ Naphtha By 3/2 $H_2$/CO with 0.2 and 1% Cobalt at 130° C. and 3000 psi The previously described $C_{10}$ fraction of the Fluid coker naphtha was hydroformylated as a 1/1 mixture with hexane at 130° C. by an about 60/40 mixture of $H_2$/CO at 3000 psi, using the high pressure procedure. The catalyst precursor was dicobalt octacarbonyl.

In the first experiment, the cobalt complex catalyst used was equivalent to 0.2% cobalt, i.e., 34 mM. The reaction mixture was periodically sampled and analyzed by capillary GC. The progress of the reaction was followed by determining both the 1-decene reactant con-

TABLE XVII

Hydroformylation of Billings Fluid Coker Naphtha With Cobalt Complexes Derived from $Co_2CO_8$

| Examples No. | Run No. E- | Feed Carbon No. | Diluent 50% cyclo-hexane | Co Conc. % | Reaction Conditions Temp. °C. | Press. psi | $H_2$/CO Ratio | Reaction Time Total Period | To react 1-n-olefin | Two Major Products n/i | Yield | Total Products Yield, % |
|---|---|---|---|---|---|---|---|---|---|---|---|---|
| 1620 | 7020 | 4–12 | Yes | 0.2 | 150 | 450 | 55/45 | 180 | 120 | | | |
| 1721 | 7013 | 10 | Yes | 0.2 | 130 | 3000 | 60/40 | 120 | 60 | 3.15 | 105 | 203 |
| 22 | 7012 | 10 | Yes | 1.0 | 130 | 3000 | 60/40 | 120 | 10 | | | |
| 1823 | 7014 | 8 | Yes | 0.2 | 130 | 3000 | 60/40 | 120 | 120 | 2.78 | 92 | 144 |
| 24 | 7018 | 8 | Yes | 0.2 | 130 | 300 | 1/1 | 180 | 100 | 2.84 | 98 | 187 |
| 1925 | 7017 | 8 | Yes | 0.2 | 150 | 3000 | 60/40 | 120 | >120 | | | |
| 26 | 7015 | 8 | Yes | 0.2 | 150 | 3000 | 1/1–3/2 | 120 | 30 | 1.92 | 84 | 201 |
| 27 | 7019 | 8 | Yes | 0.2 | 150 | 3000 | 1/1 | 120 | 120 | 2.48 | 86 | 170 |
| 2028 | 7016 | 8 | Yes | 0.2 | 150 | 4500 | 3/2 | 120 | 30 | 2.90 | 105 | 291 |
| 29 | 7023 | 10 | No | 0.2–0.3 | 130 | 3000 | 1/1 | 300 | 120 | 2.70 | 104 | 253 |
| 30 | 7022 | 10 | No | 0.2–0.4 | 130 | 3000 | 3/2 | 180 | 10 | 2.50 | 89 | 257 |

EXAMPLE 20

Hydroformylation of a $C_4$–$C_{12}$ Naphtha by $H_2$/CO with Dicobalt Octacarbonyl at 150° C. and 4500 psi The previously described broad naphtha cut was hydroformylated as a 1/1 mixture with hexane in the presence of 0.2% Co at 150° C. by an approximately 55 to 45 mixture of $H_2$ and CO at 4500 psi, using the high pressure procedure. The reaction mixture was sampled after 10, 30, 60, 120 and 180 minutes to follow the progress of the reaction by capillary GC analyses.

The GC data indicated a long induction period. Up to 30 minutes, no n-1-olefin conversion was observed. For example, the ratio of n--decene to n-decene component remained the same. However, thereafter a fast reaction occurred. The GC of the 120 minute sample showed that all the 1-n-olefin components were completely converted. The major product peaks of the GC are those of the corresponding n-aldehydes. The minor but distinct aldehyde products are 2-methyl substituted aldehydes. The n/i ratio of these major products is about 2.8.

Figure 7:
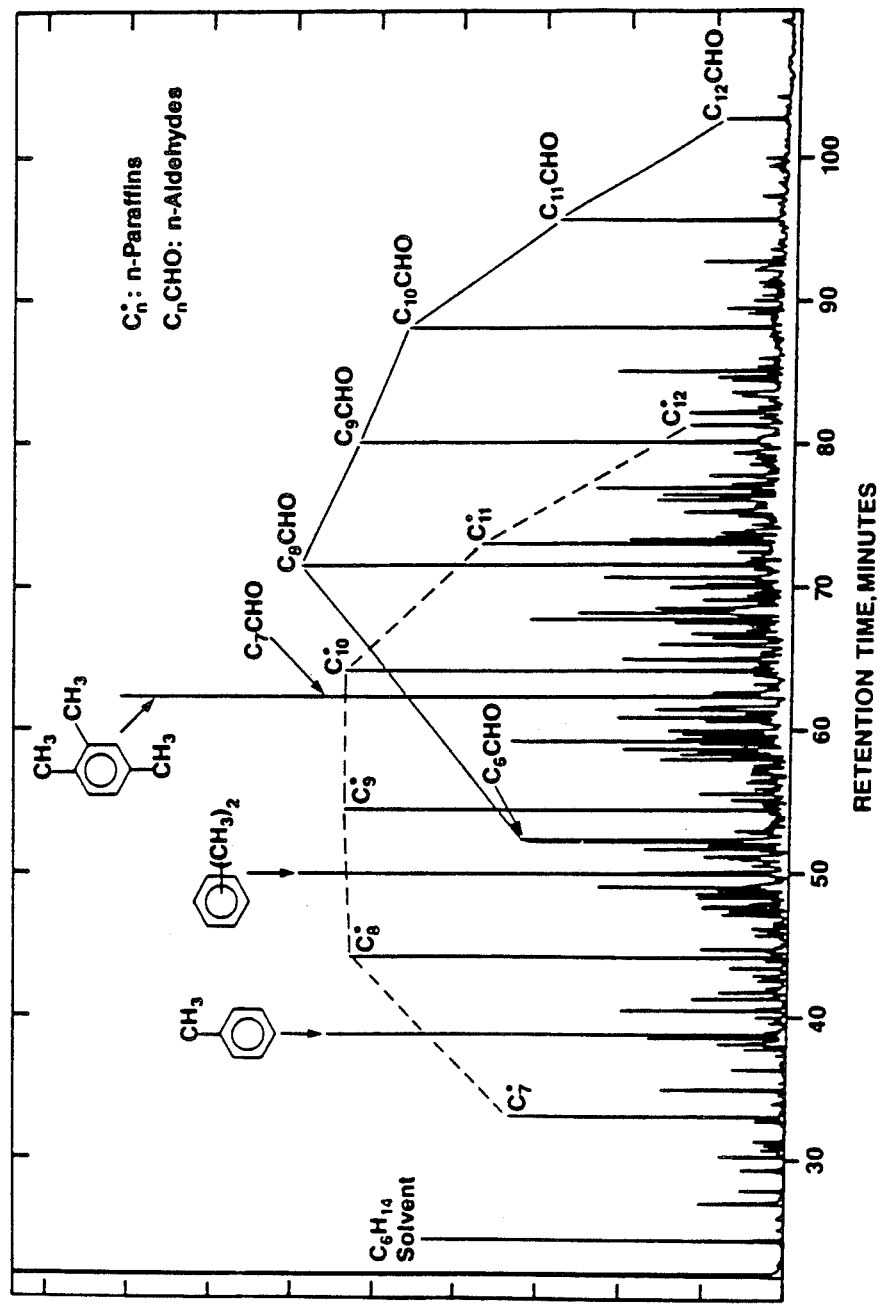
FIG. 7 shows the capillary gas chromatogram of a Fluid Coker naphtha mixture after cobalt catalyzed hydroformylation, with an indication of the major n-paraffin and n-aldehyde components.

The GC of the final reaction mixture is shown by FIG. 7. It expressly shows the major $C_7$ to $C_{13}$ aldehyde products formed and the $C_7$ to $C_{12}$ n-paraffins. A comparison of the hydrocarbon region of the figure with FIG. 1 of the naphtha feed clearly indicates that on hydroformylation the 1-n-olefin components were essentially completely converted to provide mainly the n-aldehyde products. FIG. 7 also shows that the peaks of the hydrocarbon and sulfur compound components of the feed in the $C_9$ to $C_{12}$ n-paraffins region overlap with those of the $C_7$ to $C_{10}$ aldehyde products. Since the sumed and the aldehyde product. The main aldehyde products were the n-aldehyde and 2-methyl substituted aldehyde derived from 1-decene. The data obtained are tabulated in the following

| | Reaction Time, Min | | | |
|---|---|---|---|---|
| | 10 | 30 | 60 | 120 |
| 1-Octene Converted, % | 12 | 54 | 100 | 100 |
| Major Aldehydes Formed, % | 7 | 51 | 93 | 105 |
| Total Aldehydes Formed, % | | | 143 | 203 |
| n/i Ratio of Major Aldehydes | | 3.35 | 3.39 | 3.15 |

It is apparent from the data that the 1-n-decene was converted at first. However, by the end of the 2 hour reaction period a significant reaction of the isomeric decenes also occurred. The final ratio of the two major aldehydes formed was 3.15. No significant secondary reaction took place. Alcohol formation was negligible. High boiling by-products were virtually absent.

In the second experiment, the same reaction was carried out in the presence of 1% cobalt. This resulted in a very fast reaction. In 10 minutes, the -decene component was completely converted. The amount of the two major aldehydes formed was 105% of the theoretical quantity derivable from 1-decene. The total aldehydes formed were 212% of this calculated value. The n/i ratio of the two major aldehyde products was 2.71.

The second experiment was also run for 2 hours. During the second hour much hydrogenation occurred. By the end of the second hour, essentially all the primary aldehyde products were converted to the corresponding alcohols.

EXAMPLES 23 AND 24

Hydroformylation of $C_8$ Naphtha by 3/2 and 1/1 $H_2$/CO with Cobalt at 130° C. and 3000 psi The $C_8$ fraction of the previously described naphtha was hydroformylated in hexane in the presence of 0.2% cobalt at 130° C. and 3000 psi in two experiments. The $H_2$/CO reactant ratio was about 60/40 in the first experiment while an equimolar mixture of synthesis gas was used in the second.

Qualitatively, the reaction of octenes in this example was similar to that of decenes as described in the previous examples. However, the reaction rates were generally lower. A summary of data obtained in the first experiment with 60/40 $H_2$/CO is provided by the following tabulation.

|  | Reaction Time, Minutes | | | |
| --- | --- | --- | --- | --- |
|  | 10 | 30 | 60 | 120 |
| 1-Octene Converted, % | 6 | 14 | 29 | 100 |
| Major Aldehyde Formed, % | 3 | 10 | 21 | 92 |

The reaction had a long slow period of induction during the first hour. However, the conversion of 1-n-octene and some of the isomeric octenes was rapid during the second hour. The total amount of aldehydes formed was 144% of the theoretical amount produced from 1-n-octene. Nevertheless, due to the low reaction temperature, no aldehyde hydrogenation to alcohol occurred. The n/i ratio of the two major products was 2.78, definitely lower than in the analogous experiment of the previous example.

The second experiment of this example was carried out under the same process conditions but using a 1/1 rather than 3/2 mixture of $H_2$ and CO reactant. The results of the two experiments were very similar; the $H_2$/CO reactant ratio had no apparent major effect at this temperature. The second experiment using 1/1 $H_2$/CO appeared to have a slightly longer induction period. However, during the second hour of the reaction, a rapid conversion took place. By the end of the second hour, all the 1-n-octene was converted. The reaction was continued for a third hour. Additional conversion of the two other isomers occurred. After three hours reaction time, the total amount of aldehydes formed was 187% of the theoretical yield calculated for the 1-n-octene component of the feed. On the same basis, the yield of the total aldehydes formed in 2 hours was 125%.

EXAMPLES 25-27

Hydroformylation of $C_8$ Naphtha by $H_2$/CO Mixtures of Varying Ratios with Dicobalt Octacarbonyl at 150° C. and 3000 psi $C_8$ naphtha fraction was hydroformylated in hexane solution as usual in the presence of 0.2% cobalt provided as dicobalt octacarbonyl. Compared to the previous example, the only significant difference was the use of a higher temperature, 150° C. Three experiments were run with different initial and/or final $H_2$/CO ratios.

In the first experiment, where a 3/2 ratio of $H_2$/CO was used all through the reaction, a severe inhibition of hydroformylation was observed. After 1 and 2 hours reaction time, the amounts of reacted 1-n-octene were only 20 and 27%, respectively. As expected, the significant products were n-nonanal and 2-methyl octanal. Their ratio was 3.48.

In the second experiment with an initially equimolar $H_2$/CO reactant, a much faster reaction was observed. About 20% of the 1-n-octene component reacted in 10 minutes according to GC; all the 1-octene reacted in 30 minutes. In 60 minutes, much of the linear octenes and 2-methylheptene-1 were also converted. The product data obtained on GC analyses of product samples were the following.

|  | Reaction Time, Min | | |
| --- | --- | --- | --- |
|  | 30 | 60 | 120 |
| Two Major Aldehydes Formed, % | 59 | 92 | 84 |
| Total Aldehydes Formed, % | 82 | 182 | 201 |
| n/i Ratio of Major Aldehydes | 2.59 | 2.41 | 1.92 |

The data indicate that significant amounts of olefin isomerization occurred during hydroformylation. During the first part of the reaction, the major 1-n-octene component was partly isomerized to the thermodynamically favored linear octenes. Thus, no 1-octene was shown in the reaction mixture after 30 minutes, even though only 59% of the products derivable from 1-n-octene were formed. Most of the hydroformylation took place during the subsequent 30 minutes. An apparent side reactin during the second hour was the hydrogenation of aldehyde products to the corresponding alcohols. By the end of the reaction, 11% of the total n-octanal formed was converted to n-octanol. However, the hydroformylation of internal octenes during the same period more than made up for the loss of total aldehydes via hydrogenation. During the second half of the hydrogenation period, the yield of the total aldehydes formed increased from 182% to 201% of the calculated yield for 1-n-octene. At the end of the reaction, less than half of the aldehydes were derived from 1-n-octene. As the amount of aldehydes formed from isomeric octenes rather than 1-n-octene increased with time, the n/i ratio of the two main aldehyde products dropped from 2.59 to 1.92. The apparent increase of 2-methyloctanal formed in part was due to the overlap of GC peaks. However, additional amounts were formed from 2-octene.

It is noted that although the initial $H_2$/CO mixture used to pressure the reaction vessel was equimolar, the feed gas during the reaction had a $H_2$/CO ratio of about 60/40. Since the liquid reaction mixture was sampled four times with considerable gas loss, by the end of the reaction the $H_2$/CO ratio increased to 60/40. It is felt that the initially low value of $H_2$/CO was critical in overcoming reaction inhibition.

In the third experiment, the $H_2$/CO reactant ratio of both the initial and run synthesis gas was equimolar. However, the maintenance of the low $H_2$/CO ratio resulted in decreased reaction rates when compared to the previous experiment.

The amounts of 1-octene converted after 10, 30, 60 and 120 minutes, were 30, 38, 79 and 100%, respectively. The yields of the two major products, n-octanal plus 2-methyl heptanal, after 60 and 120 minutes were 44 and 86%, respectively, based on 1-n-octene. During the same last two periods, the yield of the total aldehydes formed was 61 and 170%. The n/i ratio of the two major products was 2.70 and 2.48, respectively. By the end of the reaction, 3.5% of the n-octanal was hydrogenated to n-octanol. Overall, the GC data obtained showed that although 1-octene conversion started immediately, the final extent of hydroformylation was lower than in the previous example. High CO partial pressure was important in overcoming the initial inhibition, but the $H_2$ partial pressure was insufficient to assure a high hydroformylation rate.

EXAMPLE 28

Hydroformylation of $C_8$ Naphtha by 3/2 $H_2$/CO with Dicobalt Octacarbonyl at 150° C. and 4500 psi A hexane solution of $C_8$ naphtha was hydroformylated as usual in the presence of 0.2% cobalt by 3/2 $H_2$/CO at 150° C. and 4500 psi. The conditions were identical to those of the first experiment of the previous example, except the pressure was increased in the present experiment from 3000 to 4500 psi. This resulted in a drastically reduced initiation period and a much more complete conversion of the olefin components during the two hour reaction period.

In ten minutes, 19% of the 1-n-octene was converted and n-octanal was formed in amounts corresponding to 11% of the starting 1-n-octene reactant.

Thereafter, a rapid reaction took place. In 30 minutes, essentially all the 1-n-octene and the 2-methyl heptene-1 were converted. GC analyses provided the following data on the products formed.

|  | Reaction Time, Min | | |
| --- | --- | --- | --- |
|  | 30 | 60 | 120 |
| Two Major Aldehydes Formed, % | 95 | 120 | 105 |
| Total Aldehydes Formed, % | 149 | 247 | 291 |
| n/i Ratio of Major Aldehydes | 2.9 | 2.7 | 2.5 |
| n-Octanal Converted to n-Octanol, % | 10 | 16 |  |

It is particularly noted, that after the initial conversion of the 1-n-octene in 30 minutes, the total yield of aldehydes increased from 149 to 291% of the calculated yield for 1-n-octene. This increase is due to the conversion of internal olefins. It should also be noted that the final n/i ratio of the two major aldehyde products was fairly high (2.5), considering the high conversion of internal olefins.

During the second hour of the reaction period, there was a slight decrease of the two major aldehydes in the mixture. This is apparently due to hydrogenation of aldehydes to alcohols. A comparison of the GC signal intensities indicated that about 16% of the n-octanal formed was converted to n-octanol.

Thus the results show that at the increased pressure of the 3/2 $H_2$/CO mixture, the concentration of CO is sufficient to overcome the sulfur inhibition. The high partial pressure of hydrogen results in a high reaction rate of both 1-n-olefins and internal olefins.

EXAMPLE 29

Hydroformylation of $C_{10}$ Naphtha By $H_2$/CO Mixtures of Varying Ratios and With Varying Concentrations of Cobalt and Separation of $C_{11}$ Aldehyde Products The $C_{10}$ fraction used was a high boiling naphtha fraction. The 1-decene content of this fraction by GC was about 16%. Based on an NMR analysis, the type distribution of the decene components was the following:

| $RCH=CH_2$ | $RCH=CHR$ | $R_2C=CH_2$ | $R_2C=CHR$ | Decadiene |
| --- | --- | --- | --- | --- |
| I | II | III | IV | Conjugated |
| 43% | 22% | 14% | 9% | 12% |

Assuming that 1-decene is the only type I olefin present, the total percentage of olefinic unsaturates was 37%.

About 1900 g portions of a $C_{10}$ fluid coker naphtha fraction similar to the one previously described were hydroformylated without any significant amount of added solvent in a 1 gallon reactor. The cobalt catalyst was added as an approximately 10% solution of dicobalt octacarbonyl in toluene. The resulting essentially non-diluted feeds contained increased concentrations of both olefin reactants and sulfur inhibitors. As such, they required greater amounts of cobalt for effective catalysis.

There were two experiments carried out using dicobalt octacarbonyl as a catalyst precursor at 130° C. under 3000 psi pressure, with 1/1 $H_2$/CO and 3/2 $H_2$/CO reactant gas, respectively. The initial amount of the catalyst employed was equivalent to 0.2% cobalt in both cases. This amount of catalyst did not lead to any significant hydroformylation in 5 hours in either case. Thereafter, an additional 0.1% and 0.2%, respectively, of cobalt were added after cooling the mixture and starting the reactions again.

When the first experiment (Example 29) was resumed in the presence of a total of 0.3% cobalt, hydroformylation occurred at a moderate rate. All the 1-n-decene was consumed in 120 minutes. The total reaction time was 5 hours. GC analysis of the final reaction mixture indicated a total aldehyde product yield of about 253%, based on the amount of 1-n-decene in the feed. The n/i ratio of the two major aldehydes was about 2.7. The percentage of these aldehydes in the total aldehyde mixture was 41%. In the case of the second experiment (Example 30), with a total of 0.4% cobalt, the hydroformylation was fast. All the 1-decene was converted within 10 minutes. This reaction was continued with the increased amounts of cobalt for 3 hours.

Overall, the two experiments gave similar results, and indicated that the initial small amounts of cobalt catalyst were deactivated, but the inhibitors were thus consumed. Thus, the added amounts of cobalt showed high activity which was little dependent on the $H_2$/CO ratio employed.

Figure 8:
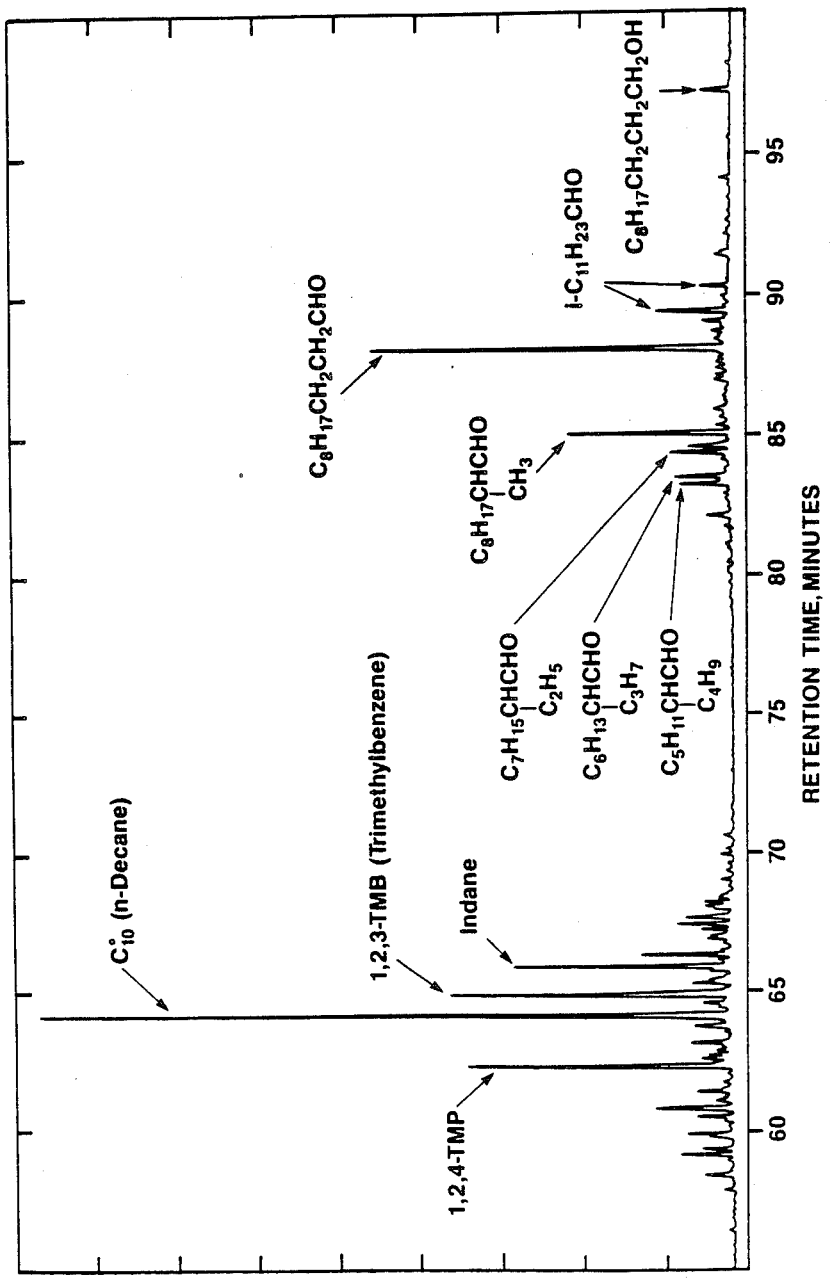
FIG. 8 shows the capillary gas chromatogram of $C_{10}$ Fluid Coker naphtha after cobalt catalyzed hydroformylation, with an indication of the isomeric $C_{11}$ aldehyde products formed.
Figure 9:
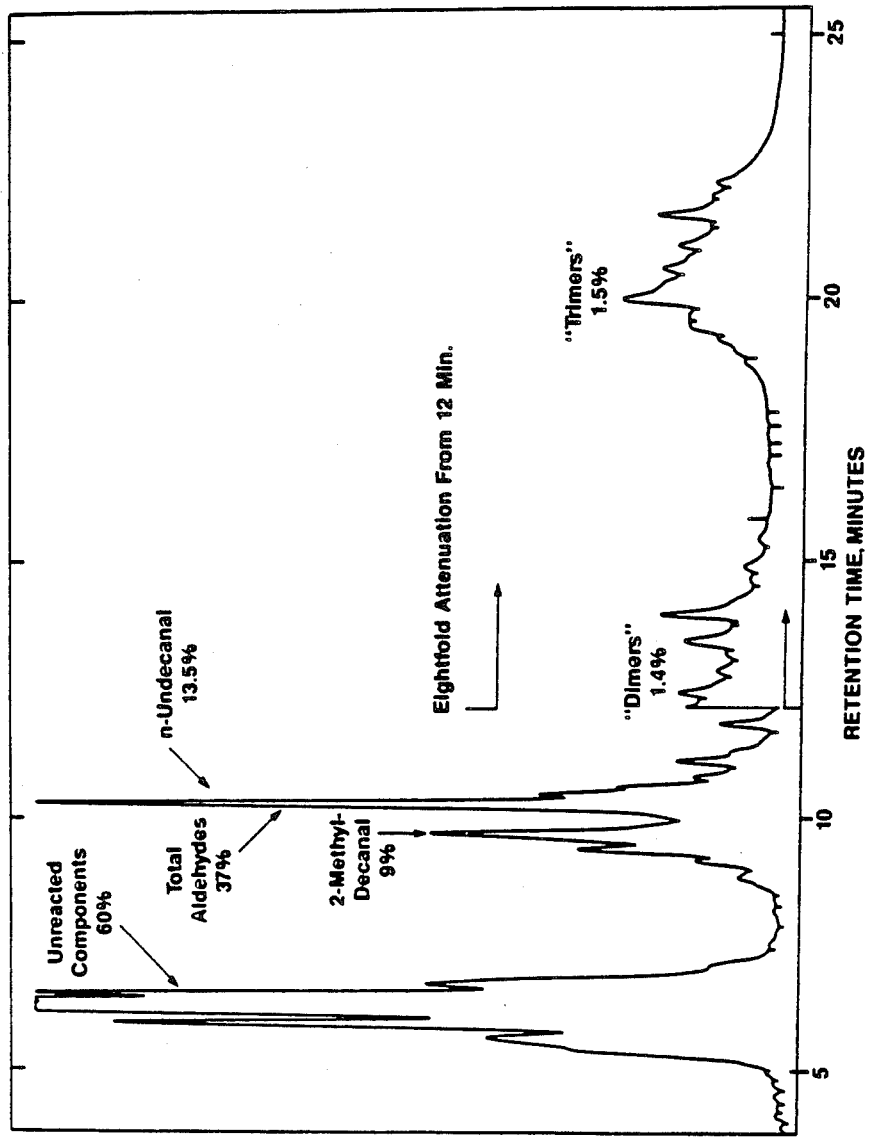
FIG. 9 shows the packed column gas chromatogram of $C_{10}$ Fluid Coker naphtha after cobalt catalyzed hydroformylation, with an indication of the $C_{11}$ aldehydes products and dimer and trimer by-products.

The composition of the combined final reaction mixtures is shown by capillary GC and packed column GC's in FIGS. 8 and 9, respectively.

FIG. 8 shows a typical reaction mixture containing major amounts of n-paraffin and n-aldehyde. Clearly, recognizable isomeric aldehyde products are also shown. These 2-alkyl substituted aldehydes are apparently derived from the various linearolefin isomers of the feed. Their structure was established in GC/MS studies on the basis of the characteristic ions formed on electron impact ionization. As it is indicated by the spectrum, decreasing amounts methyl, ethyl, propyl and butyl branched aldehydes are present.

FIG. 9 shows the packed column GC of the same reaction mixture. This GC shows less separation of the individual components, but extends the analysis to the high boiling aldehyde dimer and trimer by-products. It indicated that they amount only to about 2.9% of the total reaction mixture.

For a more detailed study of the products, it was decided to distill the reaction mixtures. The two products were combined. The cobalt was removed as cobalt acetate by hot aqueous acetic acid plus air treatment. The organic phase (976 g) was then fractionally distilled in high vacuo using a one foot packed column. The unreacted $C_{10}$ hydrocarbons were distilled at room temperature at room temperature at 0.1 mm and were collected in a cold trap, (491 g, 50 wt%). Thereafter, the $C_{10}$ aldehydes were distilled. During the distillation, some thermal decomposition of the residual liquid (probably of the formate by-products) took place. As a consequence, the vacuum dropped to 0.5 mm. However, while the bath temperature was slowly increased to 100° C., the decomposition has subsided, the vacuum improved and the $C_{11}$ aldehyde products were distilled between about 50 and 60° C. at 0.1 mm and received as colorless liquids (371 g, 38 wt%). The residual liquid dimers and trimers were 112 g, 12 wt%. Packed GC indicated that about ⅔ of this residue was consisted of very high boiling compounds, probably trimers. A large percentage of these heavy by-products was formed upon heating the mixture during fractional distillation.

The distillation results indicate that the total oxygenated product corresponds to the yield calculated for a feed at 45% olefin content assuming complete conversion. The isolated aldehyde content is less, it corresponds to an effective utilization of about 36% of the total feed.

Capillary GC of the distillate product showed that the two major aldehyde products are derived via the hydroformylation of 1-n-decene:

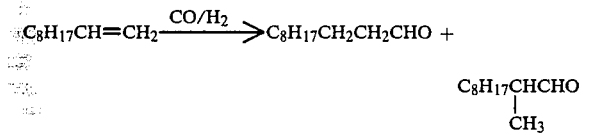

These two major products, n-undecanal and 2-methyl-decanal, constitute 49% of the aldehydes. Their ratio is 2.23. Other minor aldehydes were also identified by GC/MS.

Based on the above detailed analyses, it was calculated that the total oxygenated products contain 0.65 branch per molecule.

EXAMPLES 30-32

Hydroformylation of Atmospherically and Vacuum Distilled $C_{10}$ Naphtha Fractions with Cobalt A series of three hydroformylation experiments was carried out with three different $C_{10}$ naphtha fractions in a manner described in the previous two examples to determine the effect of the conditions of the fractional distillation of the naphtha feed on the reactivity. Information about the feeds and hydroformylation results is summarized in Table XVII.

The first fraction employed as a feed was an atmospherically distilled $C_{10}$ cut between 342° and 350° F. (172°-177° C.). According to capillary GC, it contained 10.9% 1-n-decene and 13.9% n-decane. About 55.5% of the components of this cut had longer retention times than n-decane. These components included indene.

The second fraction was obtained at reduced pressure under 240 mm. It contained 17.0% 1-n-decene and 15.0% n-decane plus 42.7% of higher boiling components.

The third fraction was derived from an atmospherically distilled $C_{10}$ fraction by redistilling it in vacuo at 50 mm. This vacuum distilled fraction mainly consisted of compounds boiling in the range of 1-n-decene, n-decane or lower. The n-decene and n-decane contents were 19.5 and 16.5% respectively. Only 23.1% of this fraction had GC retention times greater than that of n-decane.

The above described, somewhat different, three $C_{10}$ fractions were used as hydroformylation feeds in the presence of 0.1% and then an additional 0.1% Co catalyst, both added as $Co_2(CO)_8$. Each run was carried out using 1/1 $H_2$/CO as reactant gas under 3000 psi at 130° C. (266° F.). The reaction mixtures were sampled at intervals and analyzed by packed and capillary GC columns. The results are summarized in Table XVIII.

The GC composition data of the three $C_{10}$ reaction mixtures hydroformylated in the presence of 0.1% cobalt (Seq. Nos. 1a, 2a, 3a in Table XVII) show that no significant hydroformylation occurred in 360 minutes. There was some initial reaction as indicated by a small pressure drop and minor aldehyde during the first ten minutes. However, the reaction soon virtually stopped. It is apparent that the cobalt carbonyl was deactivated by the inhibitors present in the $C_{10}$ coker distillate feed.

After the unsuccessful attempts of reacting the three $C_{10}$ fractions in the presence of 0.1% cobalt, an additional 0.1% cobalt was added to the reaction mixtures. This resulted in effective hydroformylation in all three cases (Seq. Nos. 1b, 2b and 3b). However, the hydroformylation rates were somewhat dependant on the particular $C_{10}$ feed as described in the following.

The atmospherically distilled $C_{10}$ naphtha was the least reactive (Seq. No. 1). Even after the addition of the incremental cobalt (Seq. No. 1b) the reaction was slow to start and sluggish as it indicated by the minor amounts of products formed in an hour. The vacuum distilled naphtha fraction was significantly more reactive (Seq. No. 2). When the additional amount of cobalt was added, major amounts of aldehyde products (29%) were formed within an hour (Seq. No. 2b). The reaction was essentially complete in 3 hours. The atmospheric $C_{10}$ naphtha cut which was redistilled in vacuo was somewhat more reactive (Seq. No. 3). However, the vacuum distilled naphtha was more active than the atmospheric naphtha redistilled in vacuo. This seems to indicate that the inhibitors formed during atmospheric distillation are not removed on redistillation in vacuo.

The data of the table also show that there was very little dimer by-product formation in all cases. The amount of dimers formed during these reactions was less than 3% of the main aldehyde products. Although the amounts of trimers formed were not determined in this series of experiments, it is noted that as a rule considerably less trimer is formed than dimer.

TABLE XVIII

Hydroformylation of $C_{10}$ Olefinic Fractions of Fluid Coker Naphtha in the Presence of 0.2 Cobalt Catalyst Derived From $Co_2(CO)_8$ at 130° C. (266° F.) with 1/1 $H_2$/CO at 3000 psi

| Example No. | Feed Reactant Carbon Number | Feed Components % by Capillary GC | | | Catalyst Conc. Co, % | Reaction Time Min. | Total Mixture % by Packed Column GC | | | Two Main Products[a] by Capillary GC | | |
|---|---|---|---|---|---|---|---|---|---|---|---|---|
| | | 1-n-Decene | n-Decane | Higher | | | Unreacted | Aldehydes[b] | Dimers[c] | n/i Ratio | n- % | n + i % |
| 30a | $C_{10}$ Naphtha | 10.9 | 13.7 | 55.5 | 0.1 | 360 | 97.7 | 2.3 | | 3.4 | | |
| 30b | Atmospherically Distilled | | | | +0.1 | +60 | 91.8 | 8.2 | | 3.4 | 33.4 | 43.8 |
| | | | | | | 120 | 79.1 | 20.9 | | 3.3 | 30.0 | 38.7 |
| | | | | | | 180 | 70.3 | 29.6 | 0.1 | 3.1 | 28.4 | 37.2 |
| | | | | | | 360 | 64.0 | 35.2 | 0.8 | 3.0 | 26.3 | 34.7 |
| 31a | $C_{10}$ Naphtha | 17.0 | 15.0 | 42.7 | 0.1 | 360 | 96.0 | 4.0 | | 3.4 | | |
| 31b | Distilled in Vacuo (240 mm) | | | | +0.1 | +60 | 70.9 | 29.0 | 0.1 | 3.2 | 37.1 | 48.3 |
| | | | | | | 120 | 65.8 | 33.6 | 0.6 | 3.0 | 33.0 | 44.7 |
| | | | | | | 180 | 62.6 | 36.6 | 0.8 | 3.1 | 34.0 | 44.8 |
| 32a | $C_{10}$ Naphtha | 19.5 | 16.5 | 23.1 | 0.1 | 360 | 97.7 | 2.3 | | 3.3 | | |
| 32b | Distilled Atmospherically & in Vacuo (50 mm) | | | | +0.1 | +60 | 88.1 | 11.8 | 0.1 | 3.2 | 49.7 | 65.5 |
| | | | | | 120 | 69.9 | 27.0 | 0.1 | 3.2 | 43.2 | 56.6 | |
| | | | | | | 180 | 63.8 | 35.9 | 0.3 | 3.0 | 38.3 | 51.1 |

[a] n-Undecanal and 2-methyldecanal expressed as a percentage of total $C_{11}$ aldehydes.
[b] Mostly $C_{11}$ aldehydes; minor amounts of higher aldehydes and traces of $C_{11}$ alcohols are included
[c] The amounts of trimers were not determined in this series. Workup of the mixtures showed less trimers and dimers.

Analyses by capillary GC show that, as expected, the two main products of these hydroformylations were n-undecanal and 2-methyldecanal, derived from 1-n-decene. As it is shown by Table XVII, the n/i ratio of these two main products in the final reaction mixture was in the b 2.9 to 3.7 range. There were, of course, other minor branched aldehydes present. These were derived from internal and branched olefins. The amount of the completely linear aldehyde, n-decanal, in the final reaction mixtures ranges from 31.1 to 38.3% (Seq. No. 1b and 3b). This variation clearly reflects the different percentages of 1-n-decene present in these feeds. Similarly, as a consequence of the varying feed composition, the combined amounts of n-undecanal and 2-methyldecanal (n+i) changed from 41.7% to 51.1%. The rest of the product largely consisted of other monobranched 2-alkyl substituted $C_{11}$ aldehydes such as 2-ethylnonanal, 2-propyloctanal and 2-butylheptanal. These monobranched aldehydes were apparently derived from isomeric linear internal decenes.

In general, comparisons of samples, taken from the reaction mixtures at different intervals, indicate that the 1-n-decene component reacted at first, as expected. Consequently, the products of partially reacted feeds were mainly consisting of n-undecanal and 2-methyldecanal (n+i). As the reaction proceeded, and the internal and branched olefinic components were also converted, various branched aldehydes were formed and the relative amounts of the two major products derived from 1-n-decene (n+i) decreased.

Only minimal amounts of the aldehyde hydroformylation products were reduced by hydrogen to the corresponding alcohols. The only identifiable alcohol by-product was n-undecanol. Its amount was below 1% of the $C_{11}$ aldehyde products.

The three final reaction mixtures obtained were brown, as usual. Some of the brown color of the mixture derived from the atmospherically distilled feed persisted after the removal of the cobalt by the usual aqueous acetic acid, air treatment. However, the brown color of the mixtures derived from the vacuum distilled feeds changed to dark yellow upon cobalt removal.

The cobalt free reaction mixtures were fractionally distilled, using a 2 ft. packed column in vacuo, at pressures in the range of 0.1–0.2 mm. The unconverted feed components were distilled as colorless liquids with a yellow tint at ambient temperatures (20°–30° C.) using a dry ice cooled receiver. The aldehyde products were obtained as light yellow liquids between 47° and 57° C. at 0.1 mm pressure.

Due to the relatively low distillation and heating bath temperatures (100°–135° C. bath), relatively little aldehyde dimerization and trimerization occurred during distillation. For example, in the experiment using vacuum redistilled feed, 1700 g of the crude reaction mixture was distilled to obtain 570 g product and 51 g distillation residue. GC analysis indicated that this residue contained 31% product, 43% dimer and 26% trimer. Thus, the combined dimer and trimer product was 35.2 g i.e., about 6% of the main product.

The aldehyde distillate products o the three runs were combined. The combined product contained 37.1% n-undecanal, 10.4% 2-methyldecanal, about 8.6% of other 2-alkyl substituted monobranched aldehydes, about 28.7% of aldehydes having retention times longer than that of n-decanal. These latter compounds include doubly branched and possibly $C_{12}$ aldehydes. The amount of n-undecanol is minimal, about 0.2%.

Hydroformylation of $C_9$–$C_{18}$ Fluid Coker Light Gas Oil Fractions (Examples 33–59)

The previously described $C_9$ to $C_{16}$ light coker gas oil and its distillate fractions were hydroformylated without prior treating in the presence of various catalyst systems (Examples 33–50). Some hydroformylation experiments were also carried out with a broad, heavy gas oil fraction in the $C_{16}$–$C_{18}$ range in the presence of phosphine cobalt and phosphine rhodium complex catalysts (Examples 51–54).

The hydroformylation of the non-fractionated $C_9$ to $C_{16}$ light gas oil was studied with cobalt in the presence and in the absence of added phosphine ligand (Examples 33 and 35). Thereafter, the hydroformylation of narrow single carbon distillate fractions from $C_{11}$ to $C_{15}$ was investigated in the presence of cobalt at 3000 psi (Examples 36 to 50). In general, it was found that the gas oil fractions were more reactive than the naphtha fractions, particulary when distilled in vacuo. The reaction rates were directly related to the temperature, in the 110° to 170° C. range. The n/i ratio of the aldehyde products was inversely related to the reaction temperature. The isomeric aldehyde products were isolated from the reaction mixtures by fractional distillation in vacuo. The two major types of products were n-aldehydes and the corresponding 2-methyl aldehydes. The aldehydes products were reduced to the corresponding alcohols, in the presence of a sulfur resistant Co/Mo catalyst (Examples 55-59).

EXAMPLE 33

Hydroformylation of $C_9$-$C_{16}$ Light Gas Oil With Trioctyl Phosphine Cobalt Complex The previously described $C_9$-$C_{16}$ light gas oil was hydroformylated using a tri-n-octyl phosphine cobalt complex based catalyst system at 180° C. under 1000 psi pressure and a 3/2 $H_2$/CO reactant ratio. Cobalt carbonyl was employed as a catalyst precursor; its concentration was 40 mM, i.e., 0.0472% cobalt metal. The phosphine ligand was employed in 240 mM concentration to provide a 3/1 P/Co ratio. It was added to stabilize the cobalt and to obtain a more linear product.

The reaction was carried out without solvent. No induction period was observed. The reaction was discontinued after 60 minutes, although $H_2$/CO uptake continued throughout the reaction period. The amount of $H_2$ and CO consumed indicated that hydroformylation and hydrogenation both occurred to a great extent. GC indicated that the products were mainly alcohols. To enhance the analysis of the alcohol products in the GC, the reaction mixtures were treated with an excess of a silylating reagent which acts to convert the —CH$_2$OH groups of the alcohols to —CH$_2$OSi(CH$_3$)$_3$ groups. The retention time of the resulting capped alcohols in the GC column is significantly increased. The shifts of retention times by silylation confirmed that the main products were alcohols.

Figure 10:
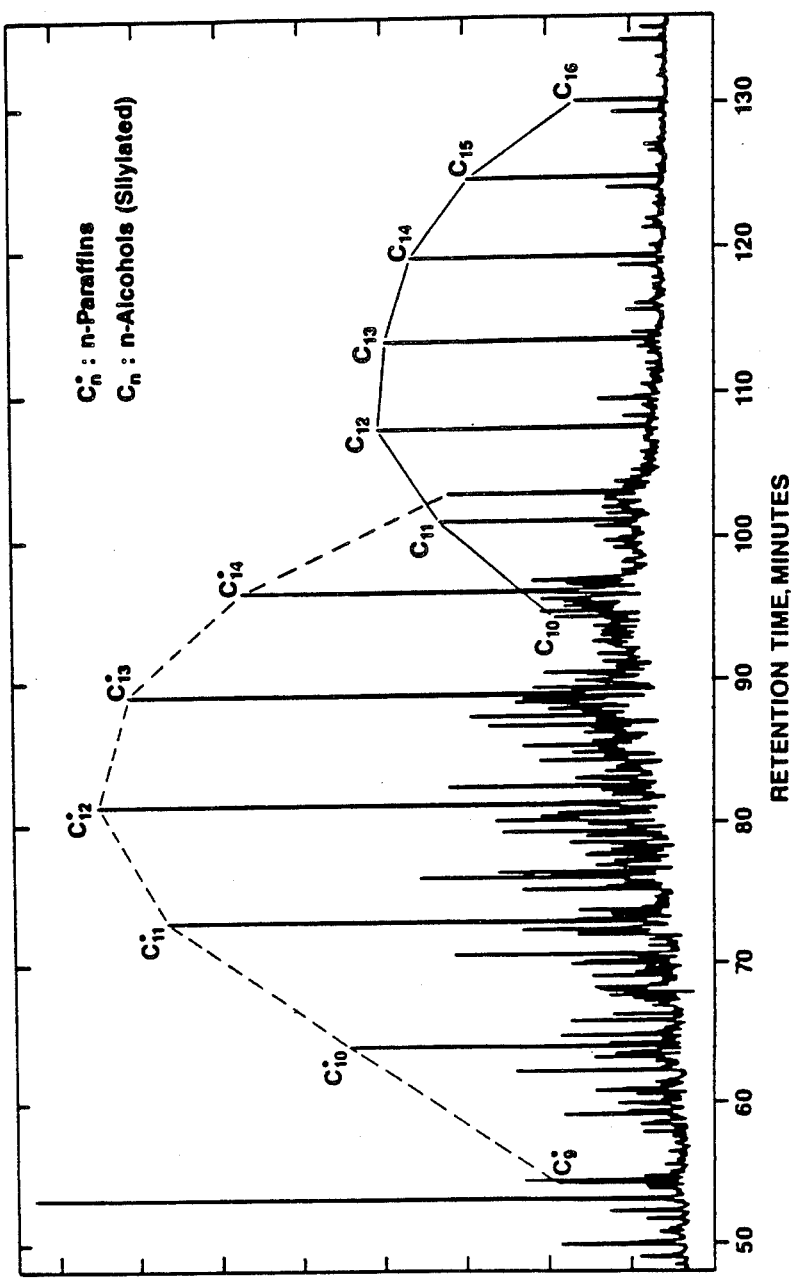
FIG. 10 show the capillary gas chromatogram of a Fluid Coker light gas oil mixture after trioctyl phosphine cobalt complex catalyzed hydroformylation, with an indication of the major n-paraffin and capped n-alcohol components.

The GC of the final silylated reaction mixture is shown by FIG. 10. The GC shows that none of the 1-n-olefin components of the feed remain in the product stream. The capped alcohol products are mostly n-alcohol derivatives. Although many branched alcohol derivatives are present, they are mostly in minor amounts. Due to their increased retention time, the peaks of most of the capped alcohols is beyond those of the hydrocarbon feed.

A comparison of the peak heights of the capped n-alcohol products derived from gas oil indicated a distribution similar to that of the starting 1-n-olefins (and n-paraffins). Thus, the reactivity of the feed 1-n-olefins is essentially independent of the olefins' carbon number in the presence of the phosphine cobalt complex catalyst.

EXAMPLE 34

Hydroformylation of $C_{10}$ Gas Oil with Triethyl Phosphine Cobalt Complex

The hydroformylation of the previously described $C_{10}$ coker gas oil fraction was also attempted in the presence of a tri-n-alkyl phosphine cobalt complex catalyst at high pressure, i.e., 3000 psi. Examples 13-17 have shown us that phosphine cobalt complexes catalyze coker naphtha hydroformylation under low pressure, i.e., 1000 psi at 180° C. and medium pressure, i.e., 1500 psi at 180° C. The purpose of the present experiments was to determine the effect of pressure on the stability and selectivity of the catalyst system.

Triethyl phosphine was selected as the ligand because it is potentially applicable in the present high temperature process. Triethyl phosphine is fairly volatile (bp. 130° C.), thus excess ligand can be removed as a forerun by distillation if desired. Triethyl phosphine can be also readily removed from the reaction mixture by an aqueous acid wash and then recovered by the addtion of a base.

As a precursor for the phosphine complex, dicobalt octacarbonyl was employed. An amount equivalent to 0.472% Co was used [0.04M Co$_2$(CO)$_8$]. The triethyl phosphine added was 2.9% (0.24M). Thus the P/Co ratio was 3.

The triethyl phosphine catalyst was dissolved in the naphtha feed which was then heated under $H_2$/CO pressure. Under the reaction conditions, a concentrated solution of the dicobalt octacarbonyl was added to the reaction mixture to preform the catalyst and start the reaction.

The reaction was followed by capillary GC analyses of samples taken after 10, 30, 60, 120 and 180 minutes. Extensive isomerization of 1-n-decene to internal decenes occurred in 30 minutes. Hydroformylation and hydrogenation of the aldehyde were rather slow. As expected, the phosphine complex of the cobalt is a more stable, but less active, hydroformylation catalyst.

Figure 11:
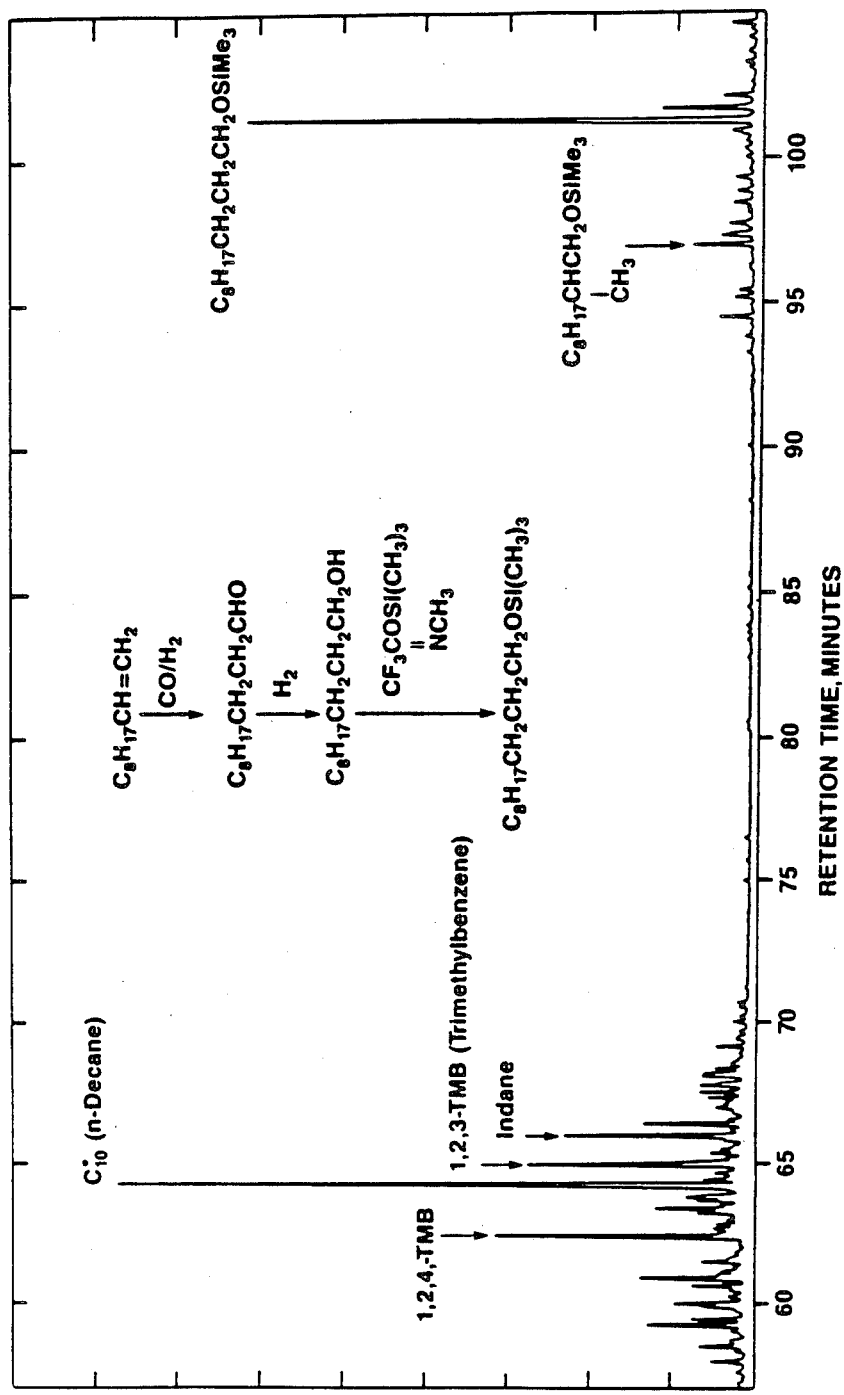
FIG. 11 shows the capillary gas chromatogram of $C_{10}$ Fluid Coker gas oil after triethyl phosphine cobalt complex catalyzed hydroformylation, with an indication of the isomeric $C_{11}$ alcohol products formed.

To increase the GC and GC/MS sensitivity for alcohols and to increase their retention time, the reaction mixture was treated with a silylating agent. The capillary GC of the resulting mixture is shown by FIG. 11.

The GC/MS established that most of the reaction products were primary alcohols. The only detectable aldehyde components present were minor amounts of n-undecanal and 2-methyldecanal. They are present in amounts less than 5% of the total oxygenated products.

As it is apparent from the figure, the main product of the reaction was the n-$C_{11}$ alcohol, undecanol. It represents 50% of the total reaction mixture. Thus, only about 50% of the products have branching. Significant amounts of 2-methyldecanol were also formed. The n/i ratio of these two products was about 10. This means that the hydroformylation of 1-decene was highly selective, since both of these compounds were derived from it. The minor alcohol components could not be identified because of similarities in their mass spectra. Based on the relatively short GC retention time the isometric $C_{12}$ alcohols were probably dibranched compounds.

The reaction mixture was also analyzed using packed column GC to estimate the amount of heavies formed. The heavies were only about 0.3% in the residual product. The presence of the phosphine ligand apparently inhibited the formation of the heavy by-products.

The reaction was stopped after 180 minutes. Thereafter, the remaining 1704 g of the product catalyst mixture was worked up. The excess phosphine and then the unreacted components were first removed in high vacuo at room temperature. However, in the absence of excess phosphine, the remaining product plus catalyst mixture was unstable when heated to 90° C. in vacuo. Thermal decomposition was indicated by a loss of vacuum. Therefore, the attempted distillation was discontinued and the catalyst was removed from the residue by aqueous acetic acid plus air treatment as usual. The water-organic mixture was diluted with hexane to facilitate the separation of the organic phase. After the removal of the solvent in vacuo, the residual product weighed 420 g. This is about 25 weight percent of the crude reactant mixture. Disregarding the weight increase of the olefinic reaction mixture during the reaction, the above amount of total oxygenated products corresponds to the conversion of 25% of the gas oil fraction employed as a feed.

The cobalt free residual product was distilled under 0.12 mm pressure. The isomeric undecyl alcohol products were obtained as a clear, colorless liquid distillate between 80° and 90° C. The dark residual heavy by-products amounted to about 5% of the total oxygenates.

EXAMPLE 35

Hydroformylation of $C_9$–$C_{15}$ Whole Coker Light Gas Oil With Cobalt at 150° C. and 4500 psi The previously described $C_9$–$C_{16}$ light gas oil was hydroformylated without solvent by a 1:1 mixture of $H_2/CO$. A toluene solution of $Co_2(CO)_8$ was introduced at 120° C. temperature and 3000 psi pressure into the reaction mixture to provide a cobalt concentration of 0.4%. When no reaction occurred, the conditions were changed to 150° C. and 4500 psi. After a 30 minute induction period, a rapid hydroformylation reaction occurred. This agrees with the hypothesis that there are equilibria among the various sulfur substituted cobalt carbonyl complexes. Dependent upon the types and amounts of sulfur compounds present in the feed, sufficiently high concentrations of CO are required to avoid the formation of inactive carbonyl-free complexes.

Figure 12:
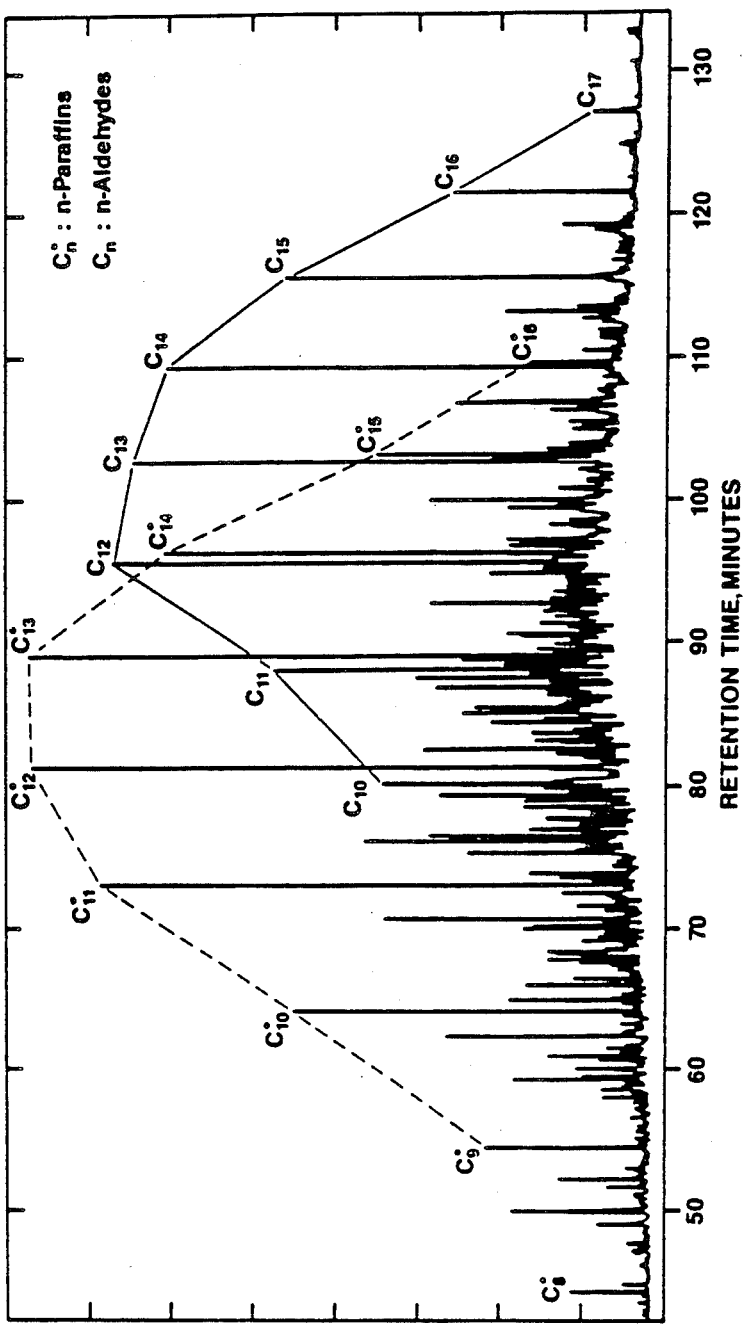
FIG. 12 shows the capillary gas chromatogram of a Fluid Coker light gas oil mixture after cobalt catalyzed hydroformylation, with an indication of the major n-paraffin and n-aldehyde components.

After a total reaction period of 3 hours, the reaction was discontinued. The capillary GC of the resulting mixture is shown by FIG. 12. It is apparent from the figure that the prominent 1-n-olefin peaks of the gas oil feed are absent after hydroformylation. The 1-n-olefins were converted mainly to n-aldehydes which show up as prominent peaks in the high retention region of the GC. The relative intensities of the $C_{11}$ to $C_{16}$ aldehyde peaks are about the same as those of the parent $C_{10}$ to $C_{15}$ olefins. The 1-n-olefins of the feed appear to be of similar reactivity without regard to their carbon number. This is in contrast to the behavior of branched higher olefins whose reactivity is rapidly decreasing with increasing carbon number.

EXAMPLES 36-38

Hydroformylation of Atmospherically and Vacuum Distilled $C_{11}$ Naphtha and Gas Oil Fractions with Cobalt A series of three hydroformylation experiments was carried out with a $C_{11}$ fraction of naphtha and the combined $C_{11}$ light gas oil fractions of a Fluid-coker distillate in the manner described in Examples 29 and 30. The experiments were designed to determine the effect of the conditions of the distillation of the gas oil feed on reactivity. Information about the feeds used and the hydroformylation results obtained is summarized in Table XIX. Some of the details are described in the following.

A narrow cut $C_{11}$ naphtha fraction boiling between 63°–71° C. (146°–150° F.) under 238 mm pressure was used in Example 36. In Example 37, the previously described combined $C_{11}$ fractions of light Fluid-coker gas oil from Billings, were employed. These fractions were obtained between 185°–196° C. (365°–385° F.) at atmospheric pressure. Part of the same $C_{11}$ fraction of light coker gas oil was redistilled without fractionation at 50 mm pressure. This redistillation of the orange $C_{11}$ fractions gave a yellow distillate, used as a hydroformylation feed in Example 38.

Each of the above $C_{11}$ feeds was hydroformylated in the presence of 0.1% Co, added as $Co_2(CO)_8$. Each run was carried out using 1/1 $H_2/CO$ under 3000 psi at 130° C. (266° F.). The reaction mixtures were sampled at intervals and analyzed by packed column and capillary GC.

The GC composition data of the reaction mixtures of Table XIX show that all the $C_{11}$ fractions could be hydroformylated under the above conditions but at different rates.

TABLE XIX

Hydroformylation of $C_{11}$ Olefinic Fractions of Naphtha and Light Gas Oil from a Fluid Coker in the Presence of 0.1% Cobalt Catalyst Derived from $Co_2(CO)_8$ at 130° C. (266° F.) with 1/1 $H_2/CO$ at 3000 psi

| Example No. | Reactant Carbon Number | Reaction Time Min. | Total Mixture, %[a] | | | Two Main Products[b] | | | 2-Alcohols[d] |
|---|---|---|---|---|---|---|---|---|---|
| | | | Unreacted | Aldehydes[e] | Dimers (Trimers) | n/i Ratio | n-[c] % | n + i[c] % | n + i |
| 36 | $C_{11}$ Naphtha | 60 | 88.5 | 11.3 | 0.2 | 3.3 | 54.3 | 71.1 | <0.1 |
| | Distilled | 120 | 73.1 | 26.3 | 0.6 | 3.2 | 39.9 | 52.2 | 0.2 |
| | in Vacuo | 180 | 68.5 | 30.7 | 0.8 | 3.1 | 39.3 | 51.9 | 0.3 |
| 37 | $C_{11}$ Gas Oil | 60 | 91.9 | 8.0 | 0.1 | 3.3 | 60.0 | 66.7 | <0.1 |
| | Atmospherically | 120 | 80.7 | 18.4 | 0.9 | 2.9 | 45.6 | 61.3 | 0.1 |
| | Distilled | 180 | 72.1 | 27.0 | 0.9 | 2.9 | 44.8 | 60.3 | 0.1 |
| | | 360 | 66.5 | 32.5 | 1.0 | 2.7 | 38.8 | 53.3 | 0.2 |
| 38 | $C_{11}$ Gas Oil | 60 | 77.1 | 22.7 | 0.2 | 2.9 | 42.8 | 57.5 | 0.1 |
| | Redistilled | 120 | 70.6 | 28.9 | 0.5 | 2.9 | 39.4 | 53.2 | 0.2 |
| | in Vacuo | 180 | 66.8 | 32.5 | 0.7 | 2.9 | 37.7 | 48.2 | 0.3 |

[a]The composition of the total reaction mixture by packed column gas chromatography.
[b]n-Dodecanol and 2-methylundecanol determined by capillary gas chromatography.
[c]Expressed as a percentage of total $C_{12}$ oxygenated products.
[d]n-Dodecanol and 2-methylundecanol determined by capillary gas chromatography.
[e]Mostly $C_{12}$ aldehydes: minor amounts of higher aldehydes and traces of alcohols are included.
[f]Mostly dimers are recorded; the minor amounts of trimers formed usually did not register.

The vacuum distilled naphtha fraction was more reactive than the atmospherically distilled gas oil fraction (Examples 36 and 37, Seq. Nos. 1 and 2). The gas oil redistilled in vacuo was the most reactive $C_{11}$ fraction of all (Example 38).

It is clear from the comparative reactivities observed that distillation in vacuo rather than at atmospheric pressure resulted in increased reactivity. While the present invention is independent of the explanation of these findings. We hypothesize that atmospheric distillation at high temperature results in the thermal decomposition of some of the thiol components to $H_2S$ plus olefin. Some of the $H_2S$ formed may dissolve in the atmospheric distillate and inhibit the hydroformylation process.

The analyses of the total reaction mixture by packed column GC show that, concurrent with the decrease of the percentage of the $C_{11}$ feeds, mostly $C_{12}$ aldehydes formed. There is very little aldehyde dimer and trimer formation; only about 3% of the main aldehyde products.

Analyses by capillary GC show that the two main products are n-dodecanal and 2-methylundecanal derived from the 1-n-undecene component of the feeds. As it is shown by the table, the ratio of these two products in the final reaction mixtures is in the 2.7 to 3.1 range. These are of course, other branched aldehydes present. These are derived from internal and branched olefins. Thus, the amount of the completely linear aldehyde, 1-n-dodecanal, is ranging from 37.7 to 39.4% of the total $C_{12}$ oxygenated products. 1-n-Dodecanal and 2-methylundecanal together represent 48.2 to 51.9%. The rest of the product contains major amounts of other, monobranched 2-alkyl substituted $C_{12}$ aldehydes such as 2-ethyldecanal, 2-propylnonanal, 2-butyloctanal and 2-pentylheptanal. These monobranched aldehydes were apparently derived from isomeric linear internal undecenes.

Only minimal amounts of the aldehyde hydroformylation products were reduced by hydrogen to give the corresponding alcohols. The only identifiable alcohol by-products were n-dodecanol and 2-methylundecanol. Their combined concentration was only 1 to 3% of that of the total aldehydes.

The three reaction mixtures obtained in the above described three examples of $C_{11}$ coker distillate hydroformylation were worked up in a manner similar to that described in Examples 29 and 30.

It was noted that the reaction mixtures derived from the vacuum distilled $C_{11}$ feeds were of definitely lighter brown color than that from the atmospheric distillate feed. The removal of cobalt by the usual aqueous acetic acid, air treatment reduced the color of all the mixtures. However, the difference between the now generally lighter colored mixtures persisted. All the mixtures were clear, free of any precipitate.

The cobalt free reaction mixtures were fractionally distilled using a 2 ft. packed column, at about 0.1 mm pressure. The unconverted feed components were distilled at close to ambient temperatures (20°–30° C.). The aldehyde product was obtained between 57°–67° C. Both distillates were light yellow, clear liquids. Due to the relatively low distillation temperature of the aldehyde products, relatively little aldehyde dimerization and trimerization occurred during distillation. The residual dimers were only about 2.5% of the total oxygenated products formed. The trimers were less than 1% although it is noted that their accurate determination by GC was not possible.

EXAMPLES 39–42

Hydroformylation of $C_{12}$ Gas Oil with Cobalt in the 110° to 150° C. Temperature Range A series of four hydroformylation experiments was carried out with a previously described, vacuum distilled combined $C_{12}$ fraction of gas oil in a manner described in Examples 29 and 30 to determine the effect of temperature on reaction rate and selectivity. Each run was carried out using 1/1 $H_2$/CO at 3000 psi. The reaction temperatures employed were 110°, 120°, 130° and 150° C. The reaction mixtures were sampled at intervals and analyzed by packed and capillary GC as usual. The results are summarized in Table XX.

The results of the table show that the $C_{12}$ fraction was more reactive than the lower boiling fractions produced by the same Fluid-coker unit.

TABLE XX

Hydroformylation of the $C_{12}$ Olefinic Fractions of Light Gas Oil from a Fluid Coker in the Presence of Cobalt Catalyst with 1/1 $H_2$/CO at 3000 psi

| Example No. | Reaction Conditions | | | | | Total Mixture, %[a] | | | Two Main Products[b] | | | 2 Alcohols[d] |
|---|---|---|---|---|---|---|---|---|---|---|---|---|
| | Temp. | | Catalyst Added | | Time | Unreacted | Aldehydes[e] | Dimers[f] | n/i Ratio | n-[c] % | n + i[c] % | n + i[c] % |
| | °C. | °F. | Complex | Co % | Min. | | | | | | | |
| 39 | 110 | 230 | Co$_2$(CO)$_8$ | 0.1 | 60 | 91.2 | 8.7 | 0.1 | | | | |
| | | | | | 180 | 73.2 | 26.6 | 0.1 | 3.7 | 58.1 | 73.7 | 0.1 |
| | | | | | 360 | 70.1 | 29.4 | 0.5 | 3.3 | 48.0 | 62.8 | 0.3 |
| 40 | 120 | 248 | (RCO$_2$)$_3$Co[g] | 0.1 | 60 | 93.4 | 6.5 | 0.1 | | | | |
| | | | | | 180 | 77.1 | 22.8 | 0.1 | 3.6 | 57.4 | 73.2 | |
| | | | | | 360 | 69.6 | 30.0 | 0.5 | 3.1 | 47.5 | 62.8 | 0.2 |
| 41 | 130 | 266 | Co$_2$(CO)$_8$ | 0.1 | 60 | 73.0 | 26.0 | 0.05 | 3.4 | 55.6 | 72.0 | 0.1 |
| | | | | | 180 | 66.1 | 33.0 | 0.5 | 2.9 | 44.1 | 59.1 | 0.3 |
| 42 | 150 | 302 | Co$_2$(CO)$_8$ | 0.05 | 60 | 95.3 | | | | | | |
| | | | | | 180 | 75.6 | 23.8 | 0.5 | 2.9 | 52.3 | 70.1 | 0.1 |
| | | | | | 360 | 65.9 | 32.9 | 1.0 | 2.3 | 35.7 | 50.9 | 0.9 |

[a]The composition of the total reaction mixtures by packed column gas chromatography.
[b]n-Tridecanol and 2-methyldodecanol determined by capillary gas chromatography.
[c]Expressed as a percentage of total $C_{13}$ oxygenated products
[d]n-Tridecanol and 2-methyldodecanol determined by capillary gas chromatography
[e]Mostly $C_{13}$ aldehydes: minor amounts of higher aldehydes and traces of alcohols are included.
[f]Mostly dimers are recorded; the minor amounts of trimers formed usually did not register.
[g]Cobalt naphthenate was used as a catalyst precursor.

About 0.1% cobalt was found effective in the first three examples of the present series, while 0.2 to 0.4% cobalt was required in the previous experiments.

As the temperature was increased from 100° to 130° C. in Examples 39, 40 and 41, the reaction rate significantly increased, At 150° C. in Example 4, only 0.05% cobalt was used. Hydroformylation occurred, nevertheless, indicating increased activity. The composition of the final reaction mixtures indicated that in the hydroformylations 130° and 150° C., at about ⅔ of the feed was converted to aldehydes.

It was found that selectivity of hydroformylation to produce a high n/i ratio of the two major aldehyde products decreased with increasing temperature. Also, more aldehyde dimer by-product and alcohol hydrogenation products were formed at 150° C. than at lower temperatures.

For the selective production of aldehydes with good olefin conversions, temperatures in the order of 130° C. are preferable. The data indicate that, in general, the 1-n-dodecene is selectively hydroformylated at first, producing a high ratio of n-tridecanal and 2-methyldodecanal. Thereafter, the linear internal olefin components are converted to various 2-alkyl substituted aldehydes. Concurrently, hydroformylation of the minor branched olefins also occurs to give some further branched aldehydes. Thus, with increasing conversion, product linearity decreases. For example, at 130° C. in Example 41, the percentage of n-tridecanal decreases from 55.6 to 44.1% as the percentage of unconverted feed drops from 73 to 66%.

Example 40 additionally shows a low temperature generation of the active catalyst species from a cobalt carboxylate rather than dicobalt octacarbonyl. In this Example, the use of cobalt naphthenate at 120° C. resulted in approximately the same conversion as that of $Co_2(CO)_8$ at 110° C. in Example 41.

The four reaction mixtures of these four examples were worked up to isolate the products in a manner similar to that of Examples 29 and 30.

All the hydroformylation product mixtures were clear dark brown liquids, free from precipitates. They were readily decobalted with aqueous acetic acid plus air treatment in the usual manner. The cobalt free mixtures were lighter brown. They were worked up separately.

Fractional distillation of the cobalt free mixtures yielded almost colorless distillate fractions of unconverted components and colorless to light yellow $C_{13}$ aldehyde products. The aldehyde products were distilled using a 1½ ft column between about 70° and 80° C. under about 0.1 mm pressure with an oil bath of 130°–160° C. During the slow distillation of about 8 hours, significant additional unsaturated aldehyde dimer formation occurred. This was the major factor in determining the isolated product yields. If alcohols are the desired products, hydrogenation of the decobalted reaction mixture prior to fractional distillation is preferred.

The distillate aldehyde products of the four examples were combined to provide sufficient amounts for subsequent hydrogenation. According to capillary GC, the combined product contained 40% n-tridecanal, 14.4% 2-methyldodecanal and 17.6% of 2-alkyl substituted aldehydes plus minor amounts of alcohols in the order of 2%.

EXAMPLES 43–46

Hydroformylation of $C_{13}$ Gas Oil with Cobalt in the 130° to 170° C. Temperature Range A series of four hydroformylation experiments were carried out with a previously described, vacuum distilled combined $C_{13}$ fraction of gas oil in a manner described in Examples 29 and 30. The reaction conditions were the same as those in the previous example. The experiments were to determine the effect of increased reaction temperature up to 170° C. The results are summarized in Table XXI.

The data of the table show that the rate of the reaction increased right up to 170° C. This is in contrast to the hydroformylation behavior found in studies of the $C_8$ naphtha fraction.

TABLE XXI

Hydroformylation of $C_{13}$ Olefinic Fractions of Light Gas Oil From a Fluid Coker in the Presence of 0.1% Cobalt Catalyst Derived From $Co_2(CO)_8$ with 1/1 $H_2/CO$ at 3000 psi

| Example No. | Reaction Conditions | | | Total Mixture, % by Packed Column GC | | | n %[a] in Total Products | Capillary GC Four Key Products[b] | | |
|---|---|---|---|---|---|---|---|---|---|---|
| | °C. | °F. | Min. | Un-reacted | Aldehydes (Alcohols) | Dimers (Trimers) | | n/i Ratio | 100 n % n + i | Alcohols |
| 43 | 130 | 266 | 60 | 78.5 | 21.0 | 0.5 | | 1.91 | 65.6 | 1.0 |
| | | | 180 | 68.5 | 31.2 | 0.5 | 40.2 | 1.56 | 61.0 | 20 |
| 44 | 140 | 284 | 60 | 73.1 | 26.4 | 0.5 | | 1.70 | 61.8 | 1.3 |
| | | | 180 | 65.4 | 33.7 | 0.9 | 35.7 | 1.48 | 59.6 | 3.4 |
| 45 | 150 | 302 | 60 | 70.6 | 28.6 | 0.8 | | 1.45 | 59.3 | 1.9 |
| | | | 180 | 65.3 | 33.3 | 1.4 | 34.1 | 1.27 | 56.0 | 7.7 |
| 46 | 160 | 338 | 60 | 66.6 | 32.2 | 1.2 | | 1.14 | 53.3 | 10.3 |
| | | | 180 | 63.3 | 33.7 | 3.0 | 26.5 | 1.14 | 53.3 | 31.6 |

[a] n-Tetradecanal in total $C_{14}$ oxygenated products.
[b] n-Tetradecanal, 2-methyl-tridecanal and the two corresponding alcohols.

As it is indicated by these data, reaction temperatures below 150° C. were advantageous for the selective production of aldehydes (Examples 43 and 44). The percentage of dimer and trimer by-products increased with the temperature. At 170° C., major amounts of alcohols were formed (Example 46).

It was also observed that the percentage of the n-aldehyde component of the total aldehyde product decreased with the temperature. Thus, the data show that reduced reaction temperatures result in increased product linearity and decreased by-product formation. It should be noted, though, that the sharply decreased n-aldehyde content of the 170° C. reaction mixture is largely due to hydrogenation to n-alcohol. At 170° C., aldehyde formation is essentially complete in 60 minutes. Thereafter, the prevalent reaction is aldehyde hydrogenation to alcohols.

All the hydroformylation product mixtures were clear brown liquids, free from precipitates. They were readily decobalted with aqueous acetic acid plus air treatment in the usual manner. Some additional dimerization of the aldehyde product occurred during distillation at 0.1 mm using a 2 ft packed column and a heating bath of about 135° C. The aldehydes distilled between 75° and 85° C. at 0.1 mm.

It was interesting to observe during the distillation of the reaction mixtures, that the color of both the unconverted components and the aldehyde products were dependent on the reaction temperature. The mixture from the 130° C. reaction yielded yellow distillates of both unconverted gas oil components and aldehyde products. The mixtures of the 140° and 150° C. reactions gave colorless hydrocarbon distillates but yellow aldehyde products. The 170° C. reaction mixture yielded colorless distillates of both hydrocarbon and aldehyde fractions.

The above observations indicate that during hydroformylation, double bond hydrogenation and, probably, desulfurization via hydrogenation become increasingly significant side reactions with increasing reaction temperatures. It is felt, though, that these hydrogenations are better carried out during the subsequent hydrogenation of the reaction mixture which provides the usually desired higher alcohol product.

The distilled aldehyde products all contained tetradecanal and 2-methyltridecanal as the major components. As it was also found in the previous examples, other 2-alkyl substituted $C_{14}$ aldehydes, when combined, constituted the third group of product components. It was shown by GC/MS studies that the 2-alkyl substituents of these aldehydes ranged from $C_2$ to $C_6$ n-alkyl.

EXAMPLES 47-49

Hydroformylation of $C_{14}$ Gas Oil with Cobalt in the 110° to 130° C. Temperature Range A series of three hydroformylation experiments were carried out with a previously described, vacuum distilled combined $C_{14}$ fraction of gas oil in a manner described in Examples 29 and 30. The reaction conditions were the same as in Examples 39 to 41, however, the amount of cobalt catalyst used was increased from 0.1 to 0.3%. The results are shown in Table XXII.

The data indicate that the reaction rate was the smallest, but product linearity was the greatest, at 110° C., the low temperature of Example 47. Conversely, at 130° C., i.e., the high temperature of Example 49, the reaction rate was the greatest but product linearity was the smallest. Since the reaction temperatures were relatively low in all three examples, there was no significant aldehyde dimer and trimer formation. The amount of alcohol hydrogenation by-products also remained low, around 3% of the aldehydes.

The product linearity is best indicated by the percentage of the n-aldehyde (and n-alcohol) in the total oxygenated products. At the end of the hydroformylation, this value was 45.2% at 110° C., 42.2% at 120° C. and 40.8% at 130° C. The percentage of the 1-n-olefin derived n-aldehyde was inversely dependent on the hydroformylation of the less reactive internal and branched olefins which provide branched aldehydes. Thus, the n-aldehyde percentage was inversely proportional to the total olefin conversion.

The n/i ratio of the two main aldehyde products, n-pentadecanal to 2-methyl-tetradecanal, was more independent of olefin conversion since both of these products can be derived from the reactive 1-n-olefin component, 1-n-tetradecene. (2-Methyl-tetradecanal can be also derived from 2-tetradecene). This n/i ratio was largely dependent on the temperature. It was inversely proportional to it as it is indicated by the data of the table.

The data of these and the previous examples suggest that a preferred method of hydroformylation is carried out at variable temperatures wherein the 1-n-olefin component is substantially converted at 130° C. or below, and the other olefins are mainly reacted at temperatures exceeding 130° C. up to 170° C. Such a variable temperature operation can be carried out in reactor system comprising reactors operating at different temperatures.

All the hydroformylation product mixtures were decobalted with aqueous acetic acid plus air treatment in the usual manner, and then fractionally distilled in vacuo. The $C_{15}$ aldehyde product was obtained as a clear yellow liquid distillate boiling between 95° and 111° C. at 0.1 mm. Using a relatively low temperature bath of 120°-140° C., relatively little, about 5%, of the aldehyde was converted into dimers and trimers during distillation.

Analyses of the distilled $C_{15}$ aldehyde product showed that it was essentially free from hydrocarbon impurities. Combined GC/MS studies indicated the presence of about 47% n-pentadecanal, 15.5% 2-methyltetradecanal and 16% 2-($C_2$–$C_6$ alkyl) substituted aldehydes. A distinct dibranched $C_{16}$ aldehyde was also found in the mixture in about 7.9% concentration. Minor amounts (0.5%) of n-pentadecanol were also present.

EXAMPLE 50

Hydroformylation of $C_{15}$ Gas Oil with 0.1% Cobalt at 140° C.

The previously described, vacuum distilled combined $C_{15}$ fraction of gas oil was hydroformylated in a manner described in Examples 29 and 30 at 140° C. under the conditions of Examples 39 to 41. The results are summarized in Table XXIII.

TABLE XXII

Hydroformylation of $C_{14}$ Olefinic Fractions of Light Gas Oil From a Fluid Coker in the Presence of 0.3% Cobalt Catalyst Derived From $Co_2(CO)_8$ with 1/1 $H_2$/CO at 3000 psi

| Example No. | Reaction Conditions | | Total Mixture, % by Packed Column GC | | | Capillary GC | | | | |
|---|---|---|---|---|---|---|---|---|---|---|
| | | | | | | All Products | | Four Key Products[c] | | |
| | Temp. °C. | Time min | Un-reacted | Aldehydes (Alcohols) | Dimers (Trimers) | n %[a] | n + i[b] %[b] | n/i Ratio[d] | 100 n % n + i | Alcohol %[e] |
| 47 | 10 | 10 | 91.5 | 8.5 | 0 | | | 3.35 | | |
| | | 60 | 75.0 | 24.5 | 0.5 | 51.4 | 67.5 | 3.18 | 76.1 | ~2 |
| | | 180 | 68.5 | 29.0 | 2.5 | 45.2 | 61.1 | 2.84 | 74.0 | ~3 |
| 48 | 120 | 10 | 86.5 | 13.3 | 0.2 | | | 3.33 | | |
| | | 60 | 71.5 | 28.0 | 0.5 | 47.7 | 63.5 | 3.02 | 75.1 | ~2 |
| | | 180 | 67.2 | 29.8 | 3.0 | 42.2 | 57.7 | 2.72 | 73.1 | ~3 |
| 49 | 130 | 10 | 76.3 | 23.0 | 0.7 | | | 3.02 | | |
| | | 60 | 67.1 | 32.0 | 0.9 | 42.3 | 58.1 | 2.67 | 72.8 | ~3 |
| | | 90 | 66.9 | 32.1 | 1.0 | 40.8 | 56.5 | 2.59 | 72.2 | ~3 |

[a]The percentage of n-pentadecanal in the total $C_{15}$ aldehydes and alcohols.
[b]The percentage of n-pentadecanal and 2-methyltetradecanal in the total products.
[c]n-Pentadecanal, 2-methyltetradecanal and their alcohol hydrogenation products.
[d]The ratio of n-pentadecanal to 2-methyltetradecanal.
[e]The two main alcohols as a percentage of the four key products.

TABLE XXIII

Hydroformylation of $C_{15}$ Olefinic Fraction of Gas Oil from a Fluid Coker in the Presence of 0.1% Cobalt Catalyst Derived from $Co_2(CO)_8$ with 1/1 $H_2$/CO at 3000 psi

| | Reaction Mixture Components, % | | Two Major |
|---|---|---|---|
| Time Min | Un-reacted | Aldehydes[b] (Alcohols) | Products n/i Ratio[c] |
| 60 | 97 | 3 | 3.14 |
| 180 | 89 | 11 | 2.87 |

TABLE XXIII-continued

Hydroformylation of $C_{15}$ Olefinic Fraction of
Gas Oil from a Fluid Coker in the Presence of 0.1% Cobalt
Catalyst Derived from $Co_2(CO)_8$ with 1/1 $H_2$/CO at 3000 psi

| Time Min | Reaction Mixture Components, % | | Two Major Products n/i Ratio[c] |
|---|---|---|---|
| | Un-reacted | Aldehydes[b] (Alcohols) | |
| 360 | 71 | 29 | 2.76 |

[a]Determined on packed column GC.
[b]Mostly aldehydes.
[c]n-Hexadecanal to 2-methylpentadecanal The data of the table show that at the low concentration of catalyst used, there was a long induction period. After 1 hour reaction time, less than 3% of aldehydes were formed. In three hours, product formation was still minimal. The maximum rate of hydroformylation was reached after 4 hours as indicated by the rate of synthesis gas consumption. A complete conversion of the 1-n-pentadecene feed component was obtained in 5 hours. After 6 hours, the amount of products in the reaction mixture was 29% and gas consumption was low. Thus, the reaction was discontinued.

Analyses of the reaction products showed high selectivity to aldehydes. The amount of alcohols and dimers each was about 1% in the final reaction mixture. The main reaction products were n-hexadecanal and 2-methylpentadecanal in an n/i ratio of 2.76. These two products amounted to 73.5% of all the $C_{16}$ aldehyde products. Most of the rest were 2-alkyl substituted $C_{16}$ aldehydes.

The final reaction mixture was decobalted as usual and fractionally distilled at 0.1 mm to separate the $C_{16}$ aldehyde product. The aldehyde was obtained as a clear yellow liquid distillate, boiling between 115° and 125° C. at 0.1 mm using a heating bath of 150°-160° C. During fractional distillation, significant aldehyde dimer and trimer formation occurred. Only 70% of the $C_{16}$ aldehyde present in the reaction mixture was recovered by distillation.

EXAMPLE 51

Hydroformylation of $C_{16}$-$C_{18}$ Gas Oil with Tri-i-butyl Phosphine Rhodium Complex at 180° C. and 1000 psi A broad cut light gas oil from a Fluid coker was distilled in vacuo to provide a $C_{16}$-$C_{18}$ fraction, having a boiling range of 74°-82° C. at 0.1 mm. A capillary GC analysis of this fraction showed that it contained approximately the following percentages of 1-n-olefins ($C_n$=) and n-paraffins ($C_n°$: $C_{15}$=, 0.30; $C_{15}°$, 0.28; $C_{16}$=, 10.06; $C_{16}°$, 6.25; $C_{17}$=, 9.55; $C_{17}°$, 7.90; $C_{18}$=, 3.34; $C_{18}°$, 3.10; $C_{19}$=, 0.78; $C_{19}°$, 0.62.

About 100 g of the above distillate feed was hydroformylated using the low pressure hydroformylation procedure under 1000 psi 1/1 $H_2$/CO pressure at 180° C. in the presence of 2 mM rhodium and 140 mM triisobutyl phosphine.

The gas consumption data indicated a very fast initial reaction, apparently a very effective conversion of the 1-n-olefin components. After this initial stage, the rate was steadily declining as the less reactive olefins were being converted. At a gas consumption calculated for a 50% conversion of a $C_{17}$ feed of 50% olefin content, the reaction was discontinued.

Capillary GC analysis of the reaction mixture showed a complete conversion of the 1-n-olefins and the formation of the corresponding 1-n-aldehydes and 2-methyl subtsituted aldehydes having one carbon more than the parent olefin. The ratio of these n- and i-aldehyde products was 1.35. Together, they represented 69% of the total aldehydes formed. A comparison of the intensities of the peaks of the two major types of aldehyde products and the n-paraffins showed that the yield of these aldehydes is about 61% of the calculated value for the 1-n-olefins. Thus a significant 1-n-olefin to internal olefin isomerization occurred during hydroformylation. The linear olefins formed were converted to 2-ethyl and higher alkyl substituted aldehydes which constitute most of the minor $C_{17}$-$C_{19}$ aldehyde products.

The reaction mixture was distilled in vacuo to separate the feed from the products. About 15 g of clear yellow-greenish product was obtained as a distillate, boiling in the range of 102° to 124° C. at 0.05 mm.

EXAMPLES 52-54

Effect of Aging on the Hydroformylation of $C_{16}$-$C_{18}$ Gas Oil with Triethyl Phosphine Cobalt Complex at 180° C. and 1500 psi The broad cut light gas oil of the previous example was hydroformylated using the medium pressure procedure in the presence of 0.23M cobalt and 0.72M triethyl phosphine. The reaction was carried out at 180° C. using an initial 1/1 $H_2$/CO reactant at a pressure of 1500 psi. The pressure was maintained with a feed gas of 3/2 $H_2$/CO ratio.

In the first example (52), a rapid initial reaction took place. GC analyses indicated that, assuming 50% olefin content for the feed, about half of the olefins were hydroformylated in 12 minutes. The major reaction products were the $C_{17}$-$C_{19}$ n-aldehydes and 2-methyl aldehydes in a n/i ratio of about 5.

In the second example (53), the same feed was used under the same conditions, but after about a month's storage at room temperature, without an antioxidant. No reaction occurred. The cobalt was precipitated. Testing of the aged feed for peroxide was positive.

In the third example (54), the aged feed was distilled in vacuo prior to being used in another hydroformylation experiment under the same conditions. The results with the redistilled feed were about the same as those with the fresh feed of Example 52.

EXAMPLES 55-59

Hydrogenation of the $C_{11}$-$C_{15}$ Aldehydes Derived from Coker Distillates to Produce the Corresponding Alcohols The combined distilled $C_{11}$ to $C_{15}$ aldehyde products of Examples 30 to 32, 36 to 38, 39 to 42, 43 to 46 and 47 to 49 were hydrogenated in the presence of a sulfur insensitive cobalt/molybdenum based hydrogenation catalyst in the manner previously described in the Experimental procedures. After about 24 hours hydrogenation at 232° C. under 300 psi pressure, the reaction mixtures were analyzed by GC/MS for aldehyde conversion. (In the case of the $C_{15}$ aldehyde, the reaction time was 48 hours.) It was found that the aldehydes were completely converted. The products were mostly the corresponding alcohols. However, some conversion to paraffins also occurred, probably via the main alcohol products.

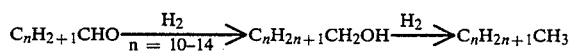

$$C_nH_{2n+1}CHO \xrightarrow[n\ =\ 10-14]{H_2} C_nH_{2n+1}CH_2OH \xrightarrow{H_2} C_nH_{2n+1}CH_3$$

The product distributions obtained in the Examples are listed in the following:

| Example Number | Carbon No. of Product | Product Distribution % Alcohol | Paraffin |
|---|---|---|---|
| 55 | 11 | 87 | 13 |
| 56 | 12 | 87 | 13 |
| 57 | 13 | 88 | 12 |
| 58 | 14 | 89 | 11 |
| 59 | 15 | 68 | 32 |

An examination of the isomer distribution of the paraffin byproducts by GC/MS showed a higher ratio of normal to iso paraffins than the n/i of the parent aldehydes. This indicated that the n-aldehydes and n-alcohols were preferably hydrogenated to paraffins. Consequently, the percentages of the n-alcohols, and the n/i ratios of n-alcohols to 2-methyl substituted alcohols, somewhat were lower than the n-aldehyde percentages and the aldehyde n/i ratios of the feeds. Since the hydrogenation to paraffins was a minor side reaction, the order of decreasing concentrations of alcohol types (normal, 2-methyl substituted, 2-ethyl and higher alkyl substituted alcohols) remained the same as that of the aldehyde feeds.

The reaction mixtures of the hydrogenations were fractionally distilled to separate the alcohol products from the paraffin by-products. Both were obtained as colorless liquid distillates of the following approximate boiling ranges.

| Carbon Number | Boiling Range, °C./mm | |
|---|---|---|
| | Alcohol Product | Paraffin By-Product |
| 11 | 135–146/20 | 97–132/20 |
| 12 | 148–158/20 | 94–135/20 |
| 13 | 145–149/10 | 96–144/10 |
| 14 | 147–163/10 | 114–145/10 |
| 15 | 163–172/10 | 117–157/10 |

GC/MS studies indicated that the alcohols had qualitatively the same isomer distribution as the parent aldehydes. The n-alcohols and the 2-methyl branched alcohols were the main components. GC/MS showed that the paraffins were derived from the aldehyde feed without structural isomerization. The paraffin forming side reaction occurred at the highest rate in case of the linear aldehyde component of the feed as indicated by the predominant formation of the n-paraffin.

This invention has been described and illustrated by means of specific embodiments and examples; however, it must be understood that numerous changes and modifications may be made within the invention without departing from its spirit and scope as defined in the claims which follow.

We claim as our invention:

1. A hydroformylation process comprising
   reacting an olefinic cracked petroleum distillate feed produced from petroleum residua by high temperature thermal cracking, and containing 1-n-olefins as the major type of olefin components and organic sulfur compounds in concentrations exceeding 0.1 percent sulfur with carbon monoxide and hydrogen
   at temperatures between about 50° and 250° C. and pressures in the range of 50 and 6000 psi
   in the presence of a Group VIII transition metal carbonyl complex catalyst in effective amounts
   to produce aldehydes and/or alcohols of semilinear character having an average of less than one alkyl branch per molecule.

2. The process of claim 1 wherein the feed is produced from vacuum residua.

3. The process of claim 2 wherein a vacuum residuum is cracked in a Fluid-coker or Flexicoker unit to produce the distillate feed for hydroformylation.

4. The process of claim 1 wherein the feed is a narrow boiling distillate fraction and the product aldehyde and/or alcohol is separated from the unreacted feed components by fractional distillation.

5. The process of claim 1 wherein the linear olefin components of the feed are selectively reacted.

6. The process of claim 1 wherein the catalyst is a homogeneous Group VIII transition metal carbonyl complex.

7. The process of claim 1 wherein the complex catalyst is modified by a trivalent phosphorus ligand.

8. The process of claim 7 wherein the catalyst is a complex of rhodium.

9. The process of claim 7, wherein the catalyst is a complex of cobalt.

10. The process of claim 1, wherein the catalyst is cobalt complex modified by a trialkyl phosphine.

11. The process of claim 1 additionally including the step of aldolizing the aldehyde product.

12. A hydroformylation process comprising reacting an olefinic cracked petroleum distillate feed containing organic sulfur compounds in concentrations exceeding 0.1% sulfur with carbon monoxide and hydrogen
   at temperatures between about 50° C. and 250° C. and pressures in the range of 50 and 4500 psi
   in the presence of a Group VIII transition metal carbonyl complex catalyst modified by a trivalent phosphorus ligand in effective amounts
   to produce aldehydes and/or alcohols.

13. The process of claim 12 wherein said olefinic feed is produced by high temperature thermal cracking and contains 1-n-olefins as the major type of olefin components and
   wherein said aldehyde and/or alcohol product has an average of less than one alkyl branch per molecule.

14. The process of claim 12 wherein said distillate is in the gas oil range.

15. The process of claim 12 wherein said modified complex catalyst is a homogeneous Group VIII transition metal complex.

16. The process of claim 12 wherein said modified catalysts is a rhodium complex.

17. The process of claim 12 wherein said modified catalyst is a cobalt complex.

18. The process of claim 13 wherein the phosphorus ligand modifier is a triorgano phosphine.

19. The process of claim 14 wherein the 1-n-olefin components are selectively reacted.

20. The process of claim 15 wherein the catalyst is a phosphine rhodium carbonyl complex selected from the group of triaryl phosphines, alkyl diaryl phosphines, dialkyl aryl phosphines and trialkyl phosphines.

21. The process of claim 16 wherein the catalyst is a trialkyl phosphine cobalt carbonyl complex.

22. A hydroformylation process comprising reacting an olefinic cracked petroleum distillate feed produced from vacuum residua by high temperature thermal cracking, and containing 1-n-olefins as the major type of olefin components and organic sulfur compounds in concentrations exceeding 0.1 percent sulfur with carbon monoxide and hydrogen at temperatures between about 100° and 180° C. and pressures between 2500 and 6000 psi in the presence of a cobalt carbonyl complex catalyst in effective amounts to produce aldehydes and/or alcohols of a semilinear character having an average of less than one alkyl branch per molecule.

23. The process of claim 22 wherein a vacuum residuum is cracked in a Fluid-coker or Flexicoker unit to produce a distillate feed for hydroformylation.

24. The process of claim 22 wherein the feed contains more than 20% olefin.

25. The process of claim 22 wherein more than 30% of the total olefins in the feed are type I olefins.

26. The process of claim 22 wherein the olefinic components of the feed possess from 8 to 35 carbons per molecule.

27. The process of claim 22 wherein the reaction is carried out between 120° and 145° C. and the main product is an aldehyde.

28. The process of claim 27 wherein the main products are n-aldehydes, 2-methyl branched aldehydes and 2-ethyl and higher alkyl branched aldehydes.

29. The process of claim 22 wherein the aldehyde product is selectively hydrogenated in the presence of a sulfur insensitive catalyst to the corresponding alcohol.

30. The process of claim 22 wherein the aldehyde product is reacted with an added alcohol to produce the corresponding dialkyl acetal.

31. A hydroformylation process comprising reacting an olefinic cracked petroleum distillate feed in the gas oil range produced from vacuum residua by high temperature thermal cracking in a Fluid-coker or Flexicoker unit which contains more than 20% olefins in the $C_8$ to $C_{20}$ range and more than 30% of said olefins being of Type I and additionally contains organic sulfur compounds in concentrations exceeding 0.1% sulfur with carbon monoxide and hydrogen at temperatures between 100° and 180° C. and pressures between 2500 and 6000 psi in the presence of a cobalt carbonyl complex in effective amounts to produce aldehydes and/or alcohols of a semilinear character having less than one branch per molecule wherein the major component of the monobranched products is 2-methyl branched and most of the rest is 2-ethyl or higher n-alkyl branched.

* * * * *